US012655126B2

(12) United States Patent
Ulsemer et al.

(10) Patent No.: US 12,655,126 B2
(45) Date of Patent: Jun. 16, 2026

(54) IMIDAZOLE-PYRAZOLE DERIVATIVES AS ANTIBACTERIALS

(71) Applicant: Hoffmann-La Roche Inc., Little Falls, NJ (US)

(72) Inventors: Sandra Marie Joseph Ulsemer, Village-Neuf (FR); Wolfgang Guba, Mueliheim (DE); Christian Lerner, Bottmingen (CH); Mingming Li, Shanghai (CN); Yongqiang Liu, Shanghai (CN); Markus Rudolph, Basel (CH); Sébastien Schmitt, Hagenthal-le-Bas (FR); Lorenz Urner, Basel (FR); Yongguang Wang, Shanghai (CN); Min Wang, Shanghai (CN); Jianhua Wang, Shanghai (CN); Song Yang, Shanghai (CN); Chengang Zhou, Shanghai (CN); Patrizio Mattei, Riehen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 555 days.

(21) Appl. No.: 18/114,959

(22) Filed: Feb. 27, 2023

(65) Prior Publication Data

US 2023/0234939 A1 Jul. 27, 2023

Related U.S. Application Data

(63) Continuation of application No. PCT/EP2021/073722, filed on Aug. 27, 2021.

(30) Foreign Application Priority Data

Aug. 31, 2020 (WO) ................ PCT/CN2020/112584
Jul. 30, 2021 (WO) ................ PCT/CN2021/109719

(51) Int. Cl.
*C07D 401/14* (2006.01)
*A61P 31/04* (2006.01)
*C07D 403/14* (2006.01)

(52) U.S. Cl.
CPC ............ *C07D 401/14* (2013.01); *A61P 31/04* (2018.01); *C07D 403/14* (2013.01)

(58) Field of Classification Search
CPC ............................ C07D 401/14; C07D 403/14
See application file for complete search history.

(56) References Cited

U.S. PATENT DOCUMENTS

| | | | |
|---|---|---|---|
| 11,390,604 B2 | 7/2022 | Blanc et al. |
| 2020/0290998 A1 | 9/2020 | Blanc et al. |
| 2022/0396565 A1 | 12/2022 | Cheng et al. |
| 2023/0017532 A1 | 1/2023 | Cheng et al. |

FOREIGN PATENT DOCUMENTS

| | | | |
|---|---|---|---|
| EP | 2226322 A | 9/2010 |
| WO | 2019/016782 A1 | 1/2019 |
| WO | 2020/126954 A1 | 6/2020 |
| WO | 2020/182648 A1 | 9/2020 |
| WO | 2021/148420 A1 | 7/2021 |
| WO | 2022/043486 A1 | 3/2022 |
| WO | 2022/049011 A1 | 3/2022 |

OTHER PUBLICATIONS

International Preliminary Report on Patentability for PCT/EP2020/055987, issued Aug. 25, 2021, pp. 1-6.
International Search Report for PCT/EP2020/055987, mailed Apr. 29, 2020, pp. 1-3.
International Preliminary Report on Patentability for PCT/EP2021/073821, issued Mar. 7, 2023, pp. 1-7.
International Search Report for PCT/EP2021/073821, mailed Oct. 29, 2021, pp. 1-3.

(Continued)

*Primary Examiner* — Shawquia Jackson
(74) *Attorney, Agent, or Firm* — Genentech, Inc.

(57) ABSTRACT

The invention provides novel imidazole pyrazole derivatives having the general formula (I), and pharmaceutically acceptable salts thereof, wherein A and $R^1$-$R^7$ are as described herein:

(I)

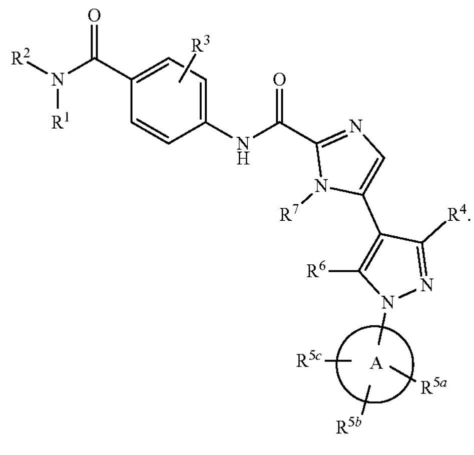

Further provided are pharmaceutical compositions including the compounds, processes of manufacturing the compounds and methods of using the compounds as medicaments, in particular methods of using the compounds as antibiotics for the treatment or prevention of bacterial infections and resulting diseases.

20 Claims, No Drawings

(56) References Cited

OTHER PUBLICATIONS

International Preliminary Report on Patentability for PCT/EP2021/073722, issued Feb. 28, 2023, pp. 1-6.
International Search Report for PCT/EP2021/073722, mailed Dec. 23, 2021, pp. 1-4.
International Search Report for PCT/EP2022/052812 (w/ Written Opinion), mailed May 3, 2022, pp. 1-8.
Knauf et al., "Exploring the Antimicrobial Action of Quaternary Amines against Acinetobacter baumannii" American Society for Microbiology 9(1):1-13 ( 2018).

IMIDAZOLE-PYRAZOLE DERIVATIVES AS ANTIBACTERIALS

CROSS-REFERENCE TO RELATED APPLICATIONS

This application is a Continuation application of International Patent Application No. PCT/EP2021/073722, filed on Aug. 27, 2021, which claims benefit of priority to International Patent Application No. PCT/CN2021/109719, filed on Jul. 30, 2021, and International Patent Application No. PCT/CN2020/112584, filed on Aug. 31, 2020, each of which is incorporated herein by reference in its entirety.

BACKGROUND

The present invention relates to novel imidazole-pyrazole derivatives which exhibit antibacterial properties. The invention also relates to methods of using the compounds for the treatment or prevention of bacterial infections and resulting diseases, in particular for the treatment or prevention of infections with *Acinetobacter baumannii* and resulting diseases.

*Acinetobacter baumannii* is a Gram-negative, aerobic, nonfermenting bacterium recognized over the last decades as an emergining pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistance that allows its survival and spread in the nosocomial setting, making this organism a frequent cause of outbreaks of infection and an endemic, health care-associated pathogen.

Due to increasing antibiotic resistance to most if not all available therapeutic options, Multi-Drug Resistant (MDR) *A. baumannii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii.*

The present invention provides novel compounds which exhibit activity against drug-susceptible as well as drug-resistant strains of *Acinetobacter baumannii.*

SUMMARY OF THE DISCLOSURE

In a first aspect, the present invention provides a compound of formula (I):

(I)

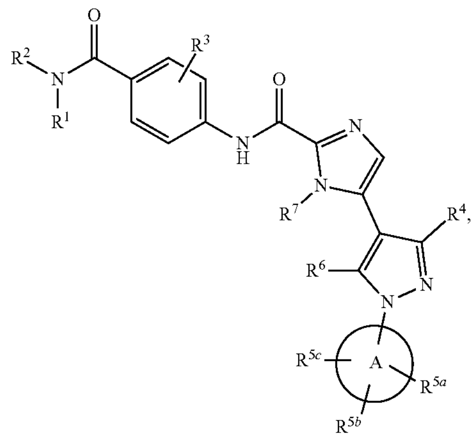

or a pharmaceutically acceptable salt thereof, wherein A and $R^1$-$R^7$ are as defined herein.

In one aspect, the present invention provides a process of manufacturing the compounds of formula (I) described herein.

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a further aspect, the present invention provides a compound of formula (I) as described herein, or a pharmaceutically acceptable salt thereof, for use in the treatment or prevention of infections and resulting diseases caused by Gram-negative bacteria.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

DETAILED DESCRIPTION OF THE DISCLOSURE

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The following definitions are provided to facilitate understanding of certain terms used frequently herein and are not meant to limit the scope of the present disclosure. All references referred to herein are incorporated by reference in their entirety.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkyldiyl" as used herein refers to a saturated linear or branched-chain divalent hydrocarbon radical of about 1 to 6 carbon atoms ($C_1$-$C_6$). Examples of alkyldiyl groups include, but are not limited to, methylene ($-CH_2-$), ethylene ($-CH_2CH_2-$), propylene ($-CH_2CH_2CH_2-$), and the like. An alkyldiyl group may also be referred to as an "alkylene" group.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "aminoalkyl" refers to an alkyl group, wherein at least one of the hydrogen atoms of the alkyl group has been replaced by an amino group. Preferably, "aminoalkyl" refers to an alkyl group wherein 1, 2 or 3 hydrogen atoms of the alkyl group have been replaced by an amino group. Preferred, yet non-limiting examples of aminoalkyl are aminomethyl and 1-aminoethyl.

The term "aminoalkoxy" refers to an alkoxy group, wherein at least one of the hydrogen atoms of the alkoxy group has been replaced by an amino group. Preferably, "aminoalkoxy" refers to an alkoxy group wherein 1, 2 or 3 hydrogen atoms of the alkoxy group have been replaced by an amino group. Preferred, yet non-limiting examples of aminoalkoxy are aminomethoxy and 1-aminoethoxy.

The term "heterocyclyl" refers to a saturated or partly unsaturated mono- or bicyclic, preferably monocyclic ring system of 3 to 10 ring atoms, preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, oxetan-3-yl, oxetan-2-yl, 1-piperidinyl, 2-piperidinyl, 3-piperidinyl, 4-piperidinyl, pyrrolidinyl (e.g. pyrrolidin-2-yl), morpholino, morpholin-2-yl, morpholin-3-yl, pyrrolidinyl (e.g., pyrrolidin-3-yl), piperazinyl (e.g., piperazin-1-yl), 3-azabicyclo[3.1.0]hexan-6-yl, or 2,5-diazabicyclo[2.2.1]heptan-2-yl. Particularly preferred, yet non-limiting examples of heterocyclyl include piperidyl, piperazinyl, pyrrolidinyl and 3-azabicyclo[3.1.0]hexan-6-yl.

The term "heteroaryl" refers to a mono- or multivalent, monocyclic or bicyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some preferred, yet non-limiting examples of heteroaryl include pyrimidinyl, pyrazolyl, pyridyl, pyrazinyl, imidazolyl, pyridazinyl, thiazolyl and 1H-pyrazolo[3,4-d]pyrimidin-6-yl. A particularly preferred, yet non-limiting examples of heteroaryl is pyridyl.

The term "hydroxy" refers to an $-OH$ group.

The term "amino" refers to an $-NH_2$ group.

The term "cyano" refers to a $-CN$ (nitrile) group.

The term "nitro" refers to a group $-NO_2$.

The term "carbamoyl" refers to a $-C(O)NH_2$ group.

The term "carbonyl" refers to a carbon radical having two of the four covalent bonds shared with an oxygen atom ($C{=}O$).

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Preferred, yet non-limiting examples of haloalkyl are trifluoromethyl, trifluoroethyl, 2-fluoroethyl, and 2,2-difluoroethyl. A particularly preferred, yet non-limiting example of haloalkyl is trifluoromethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are difluoromethoxy and trifluoromethoxy.

The term "alkoxyalkoxy" refers to an alkoxy group, wherein at least one of the hydrogen atoms of the alkoxy group has been replaced by an alkoxy group, preferably methoxy. Preferably, "alkoxyalkoxy" refers to an alkoxy group wherein 1, 2 or 3 hydrogen atoms of the alkoxy group have been replaced by an alkoxy group, most preferably methoxy. A particularly preferred, yet non-limiting example of alkoxyalkoxy is 2-methoxyethoxy.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms of the alkyl group have been replaced by an alkoxy group. A particular, yet non-limiting example of an alkoxyalkyl group is methoxymethyl.

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl, hydroxyethyl (e.g. 2-hydroxyethyl), and 3-hydroxy-3-methyl-butyl.

The term "carbamoylalkyl" refers to an alkyl group, wherein at least one of the hydrogen atoms of the alkyl group has been replaced by a carbamoyl group. Preferably, "carbamoylalkyl" refers to an alkyl group wherein 1, 2 or 3 hydrogen atoms, most preferably 1 hydrogen atom of the alkyl group have been replaced by a carbamoyl group. Preferred, yet non-limiting examples of carbamoylalkyl are 2-amino-2-oxo-ethyl, 3-amino-3-oxo-propyl and 4-amino-4-oxo-butyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "mammal" as used herein includes both humans and non-humans and includes but is not limited to humans, non-human primates, canines, felines, murines, bovines, equines, and porcines. In a particularly preferred embodiment, the term "mammal" refers to humans.

The term "nosocomial infection" refers to a hospital-acquired infection (HAI), which is an infection that is acquired in a hospital or other health care facility. To emphasize both hospital and nonhospital settings, it is sometimes instead called a health care-associated infection (HAI or HCAI). Such an infection can be acquired in hospitals, nursing homes, rehabilitation facilities, outpatient clinics, or other clinical settings.

Compounds of the Invention

In a first aspect, the present invention provides a compound of formula (I):

(I)

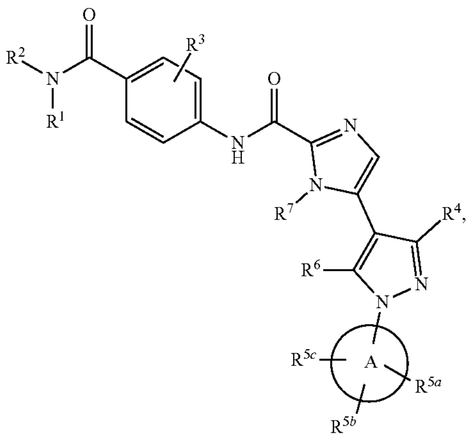

or a pharmaceutically acceptable salt thereof, wherein:

$R^1$ and $R^2$, taken together with the nitrogen atom to which they are attached, form a group of formula (II), (III) or (IV):

(II)

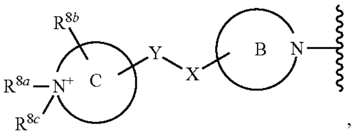

, (III)

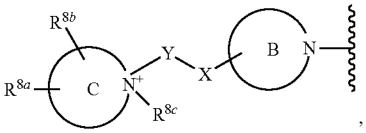

, (IV)

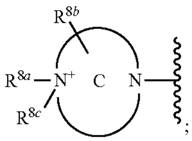

;

or $R^1$ is a group

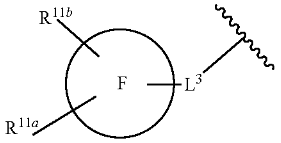

and $R^2$ is selected from hydrogen and $C_1$-$C_6$-alkyl;

$R^3$ is selected from hydrogen, halogen, $C_1$-$C_6$-alkyl and $C_1$-$C_6$-alkoxy;

$R^4$ and $R^6$ are each independently selected from hydrogen, $C_1$-$C_6$-alkyl, $C_1$-$C_6$-alkoxy, cyano, halo-$C_1$-$C_6$-alkyl and halo-$C_1$-$C_6$-alkoxy;

$R^{5a}$, $R^{5b}$ and $R^{5c}$ are each independently selected from hydrogen, halogen, hydroxy, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, $C_1$-$C_6$-alkyl-NH—C(O)—$C_1$-$C_6$-alkyl-NH—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, carbamoyl and nitro;

$R^7$ is selected from hydrogen, $C_1$-$C_6$-alkyl and halo-$C_1$-$C_6$-alkyl;

in formula (II), $R^{8a}$ is selected from $C_1$-$C_6$-alkyl, carbamoyl-$C_1$-$C_6$-alkyl and a group

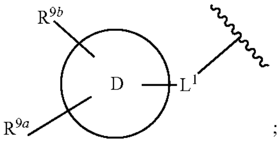

;

in formula (III), $R^{8a}$ is selected from hydrogen, $C_1$-$C_6$-alkyl, carbamoyl-$C_1$-$C_6$-alkyl and a group

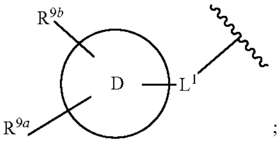

;

$R^{8b}$ is selected from hydrogen, hydroxy, hydroxy-$C_1$-$C_6$-alkyl, a group

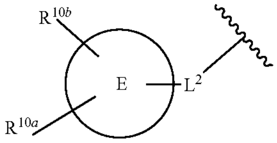

$R^{8c}$, $R^{12a}$ and $R^{12c}$ are independently $C_1$-$C_6$-alkyl;

$R^{9a}$, $R^{9b}$, $R^{10a}$, $R^{10b}$ and $R^{12b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro and hydroxy;

$R^{11a}$ and $R^{11b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro, hydroxy and a group

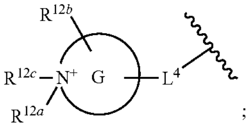

;

X is carbonyl and Y is a covalent bond, —NH—, —N($C_1$-$C_6$-alkyl)-, or $C_1$-$C_6$-alkyldiyl; or X is $C_1$-$C_6$-alkyldiyl and Y is a covalent bond;

$L^1$ and $L^3$ are each independently selected from a covalent bond, carbonyl and $C_1$-$C_6$-alkyldiyl;

$L^2$ and $L^4$ are each independently selected from a covalent bond, carbonyl, —O—, —NH—C(O)—, —C(O)—NH— and $C_1$-$C_6$-alkyldiyl;

A and E are each independently 5- to 14-membered heteroaryl;

B, C, D, F and G are each independently 3- to 14-membered heterocyclyl.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II) or (III):

(II)

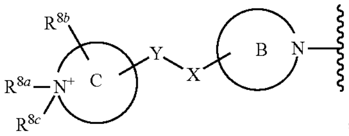

,

-continued (III)

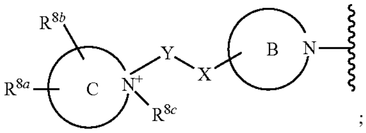

;

or $R^1$ is a group

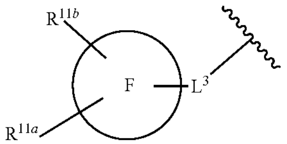

and $R^2$ is selected from hydrogen and $C_1$-$C_6$-alkyl;

$R^3$ is selected from hydrogen, halogen, $C_1$-$C_6$-alkyl and $C_1$-$C_6$-alkoxy;

$R^4$ and $R^6$ are each independently selected from hydrogen, $C_1$-$C_6$-alkyl, $C_1$-$C_6$-alkoxy, cyano, halo-$C_1$-$C_6$-alkyl and halo-$C_1$-$C_6$-alkoxy;

$R^{5a}$, $R^{5b}$ and $R^{5c}$ are each independently selected from hydrogen, halogen, hydroxy, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, carbamoyl and nitro;

$R^7$ is selected from hydrogen, $C_1$-$C_6$-alkyl and halo-$C_1$-$C_6$-alkyl;

$R^{8a}$ is selected from hydrogen, $C_1$-$C_6$-alkyl, carbamoyl-$C_1$-$C_6$-alkyl, and a group

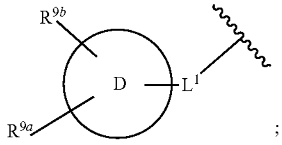

;

$R^{8b}$ is selected from hydrogen, hydroxy, hydroxy-$C_1$-$C_6$-alkyl, a group

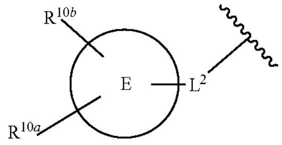

$R^{8c}$ and $R^{12c}$ are independently $C_1$-$C_6$-alkyl;

$R^{9a}$, $R^{9b}$, $R^{10a}$, $R^{10b}$, $R^{12a}$ and $R^{12b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro and hydroxy;

$R^{11a}$ and $R^{11b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro, hydroxy and a group

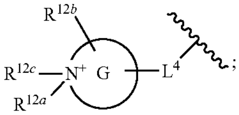

;

X is carbonyl and Y is a covalent bond or $C_1$-$C_6$-alkyldiyl; or

X is $C_1$-$C_6$-alkyldiyl and Y is a covalent bond;

$L^1$ and $L^3$ are each independently selected from a covalent bond, carbonyl and $C_1$-$C_6$-alkyldiyl;

$L^2$ and $L^4$ are each independently selected from a covalent bond, carbonyl, —O—, —NH—C(O)—, —C(O)—NH— and $C_1$-$C_6$-alkyldiyl;

A and E are each independently 5- to 14-membered heteroaryl;

B, C, D, F and G are each independently 3- to 14-membered heterocyclyl.

In one embodiment, said compound of formula (I) is a compound of formula (I-I), or a pharmaceutically acceptable salt thereof, (I-I)

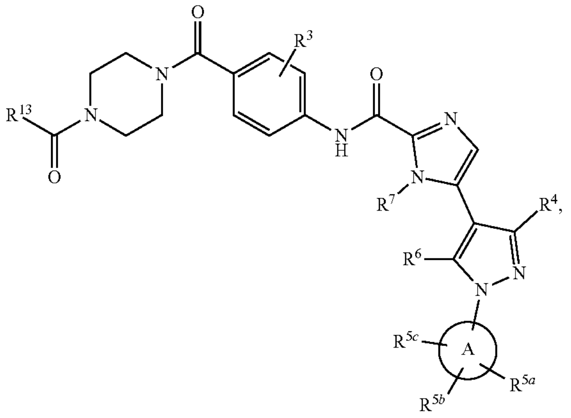

wherein:

$R^{13}$ is a group

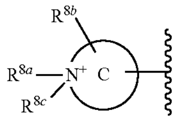

or a group

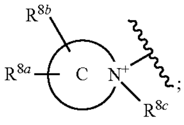

;

and $R^3$, $R^4$, $R^{5a}$, $R^{5b}$, $R^{5c}$, $R^6$, $R^7$, $R^{8a}$ and $R^{8b}$ are as defined herein.

In one embodiment, said compound of formula (I) is a compound of formula (I-II), or a pharmaceutically acceptable salt thereof, (I-II)

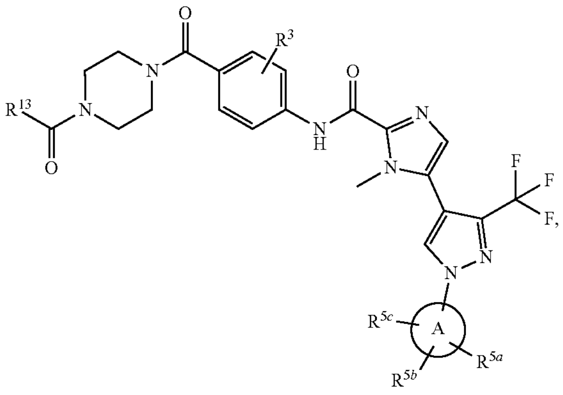

wherein:

$R^{13}$ is a group

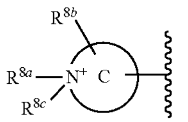

or a group R

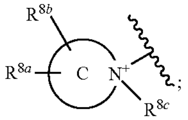

and $R^3$, $R^{5a}$, $R^{5b}$, $R^{5c}$, $R^{8a}$ and $R^{8b}$ are as defined herein.

In one embodiment, said compound of formula (I) is a compound of formula (I-III), or a pharmaceutically acceptable salt thereof, (I-III)

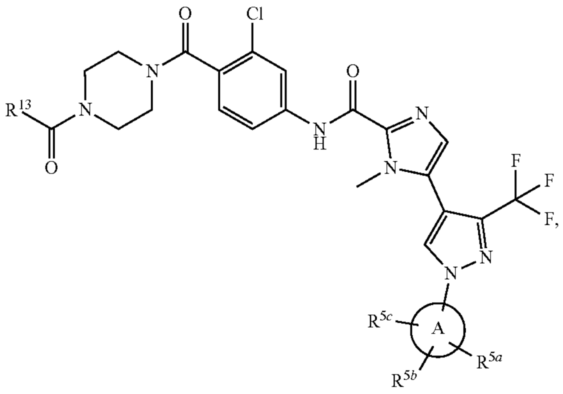

wherein:

$R^{13}$ is a group

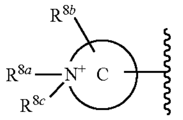

or a group

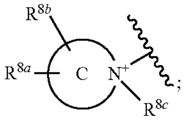

and $R^3$, $R^{5a}$, $R^{5b}$, $R^{5c}$, $R^{8a}$ and $R^{8b}$ are as defined herein.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II), (III) or (IV):

(II)

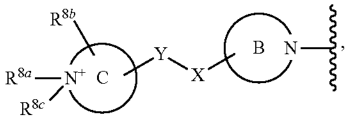

(III)

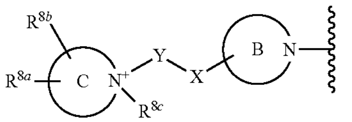

(IV)

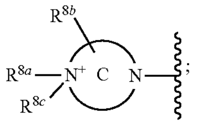

or $R^1$ is a group

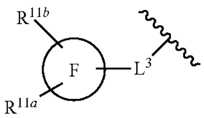

and $R^2$ is hydrogen;

$R^{9a}$, $R^{9b}$, $R^{10b}$ and $R^{11b}$ are each hydrogen;

in formula (II), $R^{8a}$ is selected from $C_1$-$C_6$-alkyl, carbamoyl-$C_1$-$C_6$-alkyl and a group

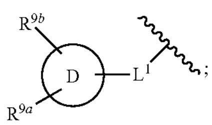

in formula (III), $R^{8a}$ is selected from hydrogen, $C_1$-$C_6$-alkyl, carbamoyl-$C_1$-$C_6$-alkyl and a group

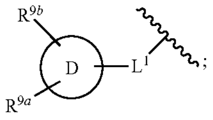

$R^{8b}$ is selected from hydrogen, hydroxy and a group

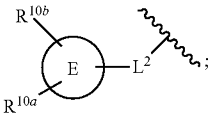

$R^{8c}$, $R^{12a}$ and $R^{12c}$ are independently $C_1$-$C_6$-alkyl;
$R^{10a}$ is selected from amino and nitro;
$R^{11a}$ is a group

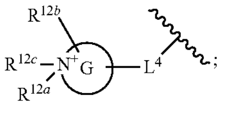

$R^{12b}$ is selected from hydrogen and hydroxy;
X is carbonyl;
Y is a covalent bond or $C_1$-$C_6$-alkyldiyl;
$L^1$ is $C_1$-$C_6$-alkyldiyl;
$L^2$ is —O—;
$L^3$ is a covalent bond;
$L^4$ is carbonyl;
B, C, D, F and G are each independently 3- to 14-membered heterocyclyl; and
E is 5- to 14-membered heteroaryl.

In one embodiment, the present invention provides a compound of formula (I) as described herein, or a pharmaceutically acceptable salt thereof, wherein $R^1$ and $R^2$, taken together with the nitrogen atom to which they are attached, form a group of formula (II) or (III):

(II)

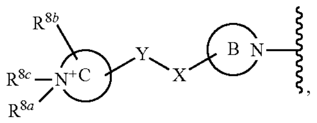

(III)

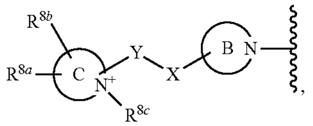

or
$R^1$ is a group

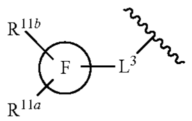

and $R^2$ is hydrogen;
$R^{9a}$, $R^{9b}$, $R^{10b}$ and $R^{11b}$ are each hydrogen;
in formula (II), $R^{8a}$ is selected from $C_1$-$C_6$-alkyl, carbamoyl-$C_1$-$C_6$-alkyl and a group

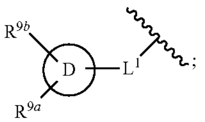

in formula (III), $R^{8a}$ is selected from hydrogen, $C_1$-$C_6$-alkyl, carbamoyl-$C_1$-$C_6$-alkyl and a group

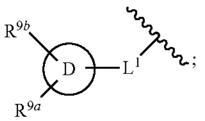

$R^{8b}$ is selected from hydrogen, hydroxy and a group

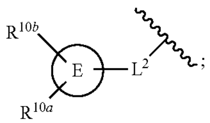

$R^{8c}$, $R^{12a}$ and $R^{12c}$ are independently $C_1$-$C_6$-alkyl;
$R^{10a}$ is selected from amino and nitro;
$R^{11a}$ is a group

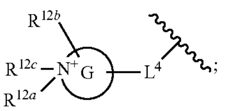

$R^{12b}$ is selected from hydrogen and hydroxy;
X is carbonyl;
Y is a covalent bond or $C_1$-$C_6$-alkyldiyl;
$L^1$ is $C_1$-$C_6$-alkyldiyl;
$L^2$ is —O—;
$L^3$ is a covalent bond;
$L^4$ is carbonyl;
B, C, D, F and G are each independently 3- to 14-membered heterocyclyl; and
E is 5- to 14-membered heteroaryl.

In a preferred embodiment, the present invention provides a compound of formula (I) as described herein, or a pharmaceutically acceptable salt thereof, wherein $R^1$ and $R^2$, taken together with the nitrogen atom to which they are attached, form a group of formula (II):

(II)

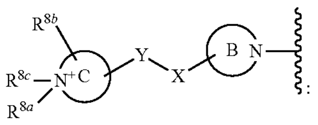

$R^{8a}$ and $R^{8c}$ are both independently $C_1$-$C_6$-alkyl;

$R^{8b}$ is selected from hydrogen and hydroxy;

X is carbonyl;

Y is a covalent bond; and

B and C are each independently 3- to 14-membered heterocyclyl.

In a particularly preferred embodiment, the present invention provides a compound of formula (I) as described herein, or a pharmaceutically acceptable salt thereof, wherein $R^1$ and $R^2$, taken together with the nitrogen atom to which they are attached, form a group of formula (II):

(II)

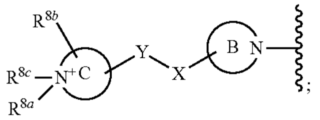

$R^{8a}$ and $R^{8c}$ are both methyl;

$R^{8b}$ is selected from hydrogen and hydroxy;

X is carbonyl;

Y is a covalent bond;

B is piperazinyl; and

C is selected from piperidyl and pyrrolidinyl.

In one embodiment, the present invention provides a compound of formula (I) as described herein, or a pharmaceutically acceptable salt thereof, wherein $R^3$ is selected from halogen and $C_1$-$C_6$-alkyl.

In a preferred embodiment, the present invention provides a compound of formula (I) as described herein, or a pharmaceutically acceptable salt thereof, wherein $R^3$ is halogen.

In a particularly preferred embodiment, the present invention provides a compound of formula (I) as described herein, or a pharmaceutically acceptable salt thereof, wherein $R^3$ is chloro.

In one embodiment, the present invention provides a compound of formula (I) as described herein, or a pharmaceutically acceptable salt thereof, wherein $R^4$ is selected from $C_1$-$C_6$-alkyl, $C_1$-$C_6$-alkoxy, cyano and halo-$C_1$-$C_6$-alkyl; and $R^6$ is selected from hydrogen and halo-$C_1$-$C_6$-alkyl.

In a preferred embodiment, the present invention provides a compound of formula (I) as described herein, or a pharmaceutically acceptable salt thereof, wherein $R^4$ is halo-$C_1$-$C_6$-alkyl; and $R^6$ is hydrogen.

In a particularly preferred embodiment, the present invention provides a compound of formula (I) as described herein, or a pharmaceutically acceptable salt thereof, wherein $R^4$ is $CF_3$; and $R^6$ is hydrogen.

In a preferred embodiment, the present invention provides a compound of formula (I) as described herein, or a pharmaceutically acceptable salt thereof, wherein A is a 5- to 9-membered heteroaryl and the other substituents of formula (I) are as defined in any of the other embodiments herein.

In a further preferred embodiment, the present invention provides a compound of formula (I) as described herein, or a pharmaceutically acceptable salt thereof, wherein A is a 5- to 9-membered heteroaryl selected from pyrimidinyl, pyrazolyl, pyridyl, pyrazinyl, imidazolyl, pyridazinyl, thiazolyl and 1H-pyrazolo[3,4-d]pyrimidin-6-yl and the other substituents of formula (I) are as defined in any of the other embodiments herein.

In one embodiment, the present invention provides a compound of formula (I) as described herein, or a pharmaceutically acceptable salt thereof, wherein A is 5- to 14-membered heteroaryl;

$R^5$, is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, $C_1$-$C_6$-alkyl-NH—C(O)—$C_1$-$C_6$-alkyl-NH—, amino-$C_1$-$C_6$-alkyl-NH—, $C_1$-$C_6$-alkoxy-$C_1$-$C_6$-alkyl-NH—, carbamoyl and nitro; and $R^{5b}$ is hydrogen or $C_1$-$C_6$-alkyl; and $R^{5c}$ is hydrogen.

In a preferred embodiment, the present invention provides a compound of formula (I) as described herein, or a pharmaceutically acceptable salt thereof, wherein A is 5- to 14-membered heteroaryl;

$R^{5a}$ is selected from $C_1$-$C_6$-alkoxy, hydroxy-$C_1$-$C_6$-alkyl, $C_1$-$C_6$-alkyl-NH—, amino-$C_1$-$C_6$-alkyl-NH— and amino;

$R^{5b}$ is hydrogen or $C_1$-$C_6$-alkyl; and $R^{5c}$ is hydrogen.

In a particularly preferred embodiment, the present invention provides a compound of formula (I) as described herein, or a pharmaceutically acceptable salt thereof, wherein A is pyridyl;

$R^{5a}$ is selected from methoxy, hydroxymethyl, methylamino, 2-aminoethylamino and amino;

$R^{5b}$ is hydrogen or methyl; and $R^{5c}$ is hydrogen.

In one embodiment, the present invention provides a compound of formula (I) as described herein, or a pharmaceutically acceptable salt thereof, wherein A is 5- to 14-membered heteroaryl;

$R^{5a}$ is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl and nitro; and $R^{5b}$ and $R^{5c}$ are both hydrogen.

In a preferred embodiment, the present invention provides a compound of formula (I) as described herein, or a pharmaceutically acceptable salt thereof, wherein A is 5- to 14-membered heteroaryl;

$R^{5a}$ is selected from $C_1$-$C_6$-alkoxy, hydroxy-$C_1$-$C_6$-alkyl, $C_1$-$C_6$-alkyl-NH—, and amino; and $R^{5b}$ and $R^{5c}$ are both hydrogen.

In a particularly preferred embodiment, the present invention provides a compound of formula (I) as described herein, or a pharmaceutically acceptable salt thereof, wherein A is pyridyl;

$R^{5a}$ is selected from methoxy, hydroxymethyl, methylamino and amino; and $R^{5b}$ and $R^{5c}$ are both hydrogen.

In a preferred embodiment, the present invention provides a compound of formula (I) as described herein, or a pharmaceutically acceptable salt thereof, wherein $R^7$ is $C_1$-$C_6$-alkyl.

In a particularly preferred embodiment, the present invention provides a compound of formula (I) as described herein, or a pharmaceutically acceptable salt thereof, wherein $R^7$ is methyl.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II), (III) or (IV):

(II)

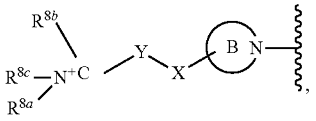

(III)

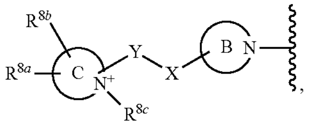

(IV)

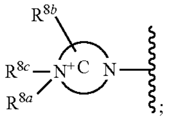

or $R^1$ is a group

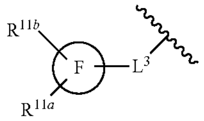

and $R^2$ is hydrogen;

$R^3$ is selected from halogen and $C_1$-$C_6$-alkyl;

$R^4$ is selected from $C_1$-$C_6$-alkyl, $C_1$-$C_6$-alkoxy, cyano and halo-$C_1$-$C_6$-alkyl;

$R^{5a}$ is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, $C_1$-$C_6$-alkyl-NH—C(O)—$C_1$-$C_6$-alkyl-NH—, amino-$C_1$-$C_6$-alkyl-NH—, $C_1$-$C_6$-alkoxy-$C_1$-$C_6$-alkyl-NH—, carbamoyl and nitro;

$R^{5b}$ is hydrogen or $C_1$-$C_6$-alkyl;

$R^{5c}$, $R^{9a}$, $R^{9b}$, $R^{10b}$, $R^{11b}$ and $R^{12b}$ are each hydrogen;

$R^6$ is selected from hydrogen and halo-$C_1$-$C_6$-alkyl;

$R^7$ is $C_1$-$C_6$-alkyl;

in formula (II), $R^{8a}$ is selected from $C_1$-$C_6$-alkyl, carbamoyl-$C_1$-$C_6$-alkyl and a group

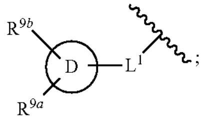

in formula (III), $R^{8a}$ is selected from hydrogen, $C_1$-$C_6$-alkyl, carbamoyl-$C_1$-$C_6$-alkyl and a group

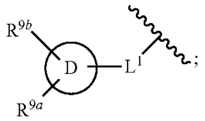

$R^{8b}$ is selected from hydrogen, hydroxy and a group

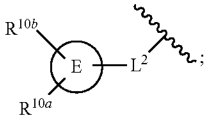

$R^{8c}$, $R^{12a}$ and $R^{12c}$ are independently $C_1$-$C_6$-alkyl;

$R^{10a}$ is selected from amino and nitro;

$R^{11a}$ is a group

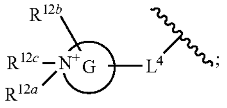

$R^{12b}$ is selected from hydrogen and hydroxy;

X is carbonyl;

Y is a covalent bond or $C_1$-$C_6$-alkyldiyl;

$L^1$ is $C_1$-$C_6$-alkyldiyl;

$L^2$ is —O—;

$L^3$ is a covalent bond;

$L^4$ is carbonyl;

A and E are each independently 5- to 14-membered heteroaryl; and

B, C, D, F and G are each independently 3- to 14-membered heterocyclyl.

In a preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II):

(II)

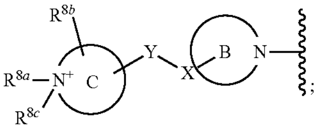

$R^3$ is halogen;

$R^4$ is halo-$C_1$-$C_6$-alkyl;

$R^{5a}$ is selected from $C_1$-$C_6$-alkoxy, hydroxy-$C_1$-$C_6$-alkyl, $C_1$-$C_6$-alkyl-NH— and amino;

$R^{5b}$ is hydrogen or $C_1$-$C_6$-alkyl;

$R^{5c}$ and $R^6$ are each hydrogen;

$R^7$ is $C_1$-$C_6$-alkyl;

$R^{8a}$ and $R^{8c}$ are both independently $C_1$-$C_6$-alkyl;

$R^{8b}$ is selected from hydrogen and hydroxy;

X is carbonyl;

Y is a covalent bond;

A is 5- to 14-membered heteroaryl; and

B and C are each independently 3- to 14-membered heterocyclyl.

In a particularly preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II):

(II)

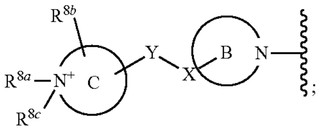

$R^3$ is chloro;

$R^4$ is $CF_3$;

$R^{5a}$ is selected from methoxy, hydroxymethyl, methylamino and amino;

$R^{5b}$ is hydrogen or methyl;

$R^{5c}$ and $R^6$ are each hydrogen;

$R^7$ is methyl;

$R^{8a}$ and $R^{8c}$ are both methyl;

$R^{8b}$ is selected from hydrogen and hydroxy;

X is carbonyl;

Y is a covalent bond;

A is pyridyl;

B is piperazinyl; and

C is selected from piperidyl and pyrrolidinyl.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II) or (III):

(II)

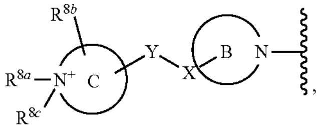

(III)

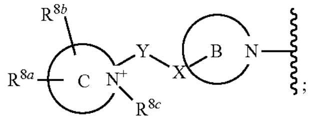

or $R^1$ is a group

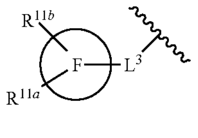

and $R^2$ is hydrogen;

$R^3$ is selected from halogen and $C_1$-$C_6$-alkyl;

$R^4$ is selected from $C_1$-$C_6$-alkyl, $C_1$-$C_6$-alkoxy, cyano and halo-$C_1$-$C_6$-alkyl;

$R^{5a}$ is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl and nitro;

$R^{5b}$, $R^{5c}$, $R^{9a}$, $R^{9b}$, $R^{10b}$, $R^{11b}$ and $R^{12b}$ are each hydrogen;

$R^6$ is selected from hydrogen and halo-$C_1$-$C_6$-alkyl;

$R^7$ is $C_1$-$C_6$-alkyl;

in formula (II), $R^{8a}$ is selected from $C_1$-$C_6$-alkyl, carbamoyl-$C_1$-$C_6$-alkyl and a group

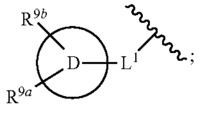

in formula (III), $R^{8a}$ is selected from hydrogen, $C_1$-$C_6$-alkyl, carbamoyl-$C_1$-$C_6$-alkyl and a group

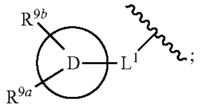

$R^{8b}$ is selected from hydrogen, hydroxy and a group

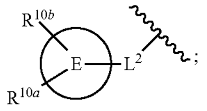

$R^{8c}$, $R^{12a}$ and $R^{12c}$ are independently $C_1$-$C_6$-alkyl;

$R^{10a}$ is selected from amino and nitro;

$R^{11a}$ is a group

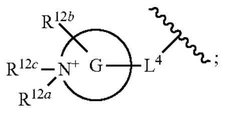

$R^{12b}$ is selected from hydrogen and hydroxy;

X is carbonyl;

Y is a covalent bond or $C_1$-$C_6$-alkyldiyl;

$L^1$ is $C_1$-$C_6$-alkyldiyl;

$L^2$ is —O—;

$L^3$ is a covalent bond;

$L^4$ is carbonyl;

A and E are each independently 5- to 14-membered heteroaryl; and

B, C, D, F and G are each independently 3- to 14-membered heterocyclyl.

In a preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II):

(II)

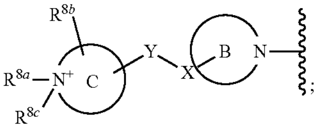

$R^3$ is halogen;

$R^4$ is halo-$C_1$-$C_6$-alkyl;

$R^{5a}$ is selected from $C_1$-$C_6$-alkoxy, hydroxy-$C_1$-$C_6$-alkyl, $C_1$-$C_6$-alkyl-NH— and amino;

$R^{5b}$, $R^{5c}$ and $R^6$ are each hydrogen;

$R^7$ is $C_1$-$C_6$-alkyl;

$R^{8a}$ and $R^{8c}$ are both independently $C_1$-$C_6$-alkyl;

$R^{8b}$ is selected from hydrogen and hydroxy;

X is carbonyl;

Y is a covalent bond;

A is 5- to 14-membered heteroaryl; and

B and C are each independently 3- to 14-membered heterocyclyl.

In a particularly preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II):

(II)

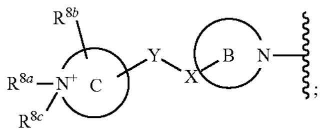

;

$R^3$ is chloro;

$R^4$ is $CF_3$;

$R^{5a}$ is selected from methoxy, hydroxymethyl, methylamino and amino;

$R^{5b}$, $R^{5c}$ and $R^6$ are each hydrogen;

$R^7$ is methyl;

$R^{8a}$ and $R^{8c}$ are both methyl;

$R^{8b}$ is selected from hydrogen and hydroxy;

X is carbonyl;

Y is a covalent bond;

A is pyridyl;

B is piperazinyl; and

C is selected from piperidyl and pyrrolidinyl.

In one embodiment, the present invention provides a compound of formula (I) as described herein, or a pharmaceutically acceptable salt thereof, wherein said compound of formula (I) is selected from:

N-[3-Chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide;

6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]pyridine-3-carboxamide;

6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]-N-methyl-pyridine-3-carboxamide;

N-[3-chloro-4-[4-(1,1-dimethylpiperidin-1-ium-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide;

5-[1-(5-amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-Chloro-4-[4-(1,1-dimethylpiperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-(3-hydroxy-1,1-dimethyl-piperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[(3S,4R)-3-hydroxy-1,1-dimethyl-piperidin-1-ium-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

N-[4-[4-[1-(Azetidin-3-ylmethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

5-[1-(5-Amino-2-pyridyl)-3-(trifluoromethyl)pyrazol-4-yl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(2S,3S)-3-hydroxy-1,1-dimethyl-pyrrolidin-1-ium-2-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(3-hydroxy-1,1-dimethyl-piperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3R,4R)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S,4R)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S,4S)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3R,4S)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(4-hydroxy-1,1-dimethyl-piperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[2-(3-hydroxy-1-methyl-pyrrolidin-1-ium-1-yl)acetyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[[1-(1,1-dimethylpiperidin-1-ium-4-carbonyl)-4-piperidyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S)-4,4-dimethylmorpholin-4-ium-3-carbonyl]piperazine-1-carbonyl]phenyl]-1-methyl-imidazole-2-carboxamide;

N-[4-[4-[(2S,3S)-3-[(5-amino-2-pyridyl)oxy]-1,1-dimethyl-pyrrolidin-1-ium-2-carbonyl]piperazine-1-carbonyl]-3-chloro-phenyl]-5-[1-(5-amino-2-pyridyl)-3-(trifluoromethyl)pyrazol-4-yl]-1-methyl-imidazole-2-carboxamide;

5-[1-(5-Amino-2-pyridyl)-3-(trifluoromethyl)pyrazol-4-yl]-N-[3-chloro-4-[4-[(2S)-4-hydroxy-1,1-dimethyl-piperidin-1-ium-2-carbonyl]piperazine-1-carbonyl]phenyl]-1-methyl-imidazole-2-carboxamide;

N-[3-Chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-(1,1-dimethylpiperidin-1-ium-4-carbonyl)piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide;

N-[3-chloro-4-[4-(1,1-dimethylpiperidin-1-ium-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide;

N-[3-chloro-4-[4-(4-hydroxy-1,1-dimethyl-piperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[2-(3-hydroxy-1-methyl-pyrrolidin-1-ium-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[4-[4-(1,1-dimethylpiperidin-1-ium-4-carbonyl)piperazine-1-carbonyl]-3-methyl-phenyl]-1-methyl-5-[1-[5-(methylamino)-2-pyridyl]-3-(trifluoromethyl)pyrazol-4-yl]imidazole-2-carboxamide;

N-[3-chloro-4-[4-[(3S,4R)-3-hydroxy-1,1-dimethyl-piperidin-1-ium-4-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-Chloro-4-[4-(1,1-dimethylpiperidin-1-ium-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide;

N-[3-Chloro-4-[4-(1,1-dimethylpiperidin-1-ium-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide;

5-[1-(5-Amino-2-pyridyl)-3-(trifluoromethyl)pyrazol-4-yl]-N-[3-chloro-4-[4-(4,4-dimethylpiperazin-4-ium-1-carbonyl)piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[3-(hydroxymethyl)-4,4-dimethyl-piperazin-4-ium-1-carbonyl]piperidine-1-carbonyl]phenyl]-1-methyl-imidazole-2-carboxamide;

5-[1-(5-Amino-2-pyridyl)-3-(trifluoromethyl)pyrazol-4-yl]-N-[3-chloro-4-[4-[(4,4-dimethyl-2-oxo-piperazin-4-ium-1-yl)methyl]piperidine-1-carbonyl]phenyl]-1-methyl-imidazole-2-carboxamide;

5-[1-(5-Amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-cyano-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-methyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-ethyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(6-Aminopyridazin-3-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide;

5-[1-[5-[(3-Amino-3-oxo-propyl)amino]-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

4-(2-chloro-4-(1-methyl-5-(1-(pyrimidin-2-yl)-3-(trifluoromethyl)-1H-pyrazol-4-yl)-1H-imidazole-2-carboxamido)benzoyl)-1,1-dimethylpiperazin-1-ium;

rac-(2R,4S)-2-((1R,5S,6S)-6-(2-chloro-4-(1-methyl-5-(1-(pyrimidin-2-yl)-3-(trifluoromethyl)-1H-pyrazol-4-yl)-1H-imidazole-2-carboxamido)benzamido)-3-azabicyclo[3.1.0]hexane-3-carbonyl)-4-hydroxy-1,1-dimethylpyrrolidin-1-ium;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

(exo)-6-[[4-[[5-[1-(5-aminopyridin-2-yl)-3-(trifluoromethyl)pyrazol-4-yl]-1-methylimidazole-2-carbonyl]amino]-2-chlorobenzoyl]amino]-[(trans)-4-hydroxy-1,1-dimethylpyrrolidin-1-ium-3-yl]-3-azabicyclo[3.1.0]hexane-3-carboxamide;

N-[3-chloro-4-[4-(1,1-dimethylpiperidin-1-ium-4-carbonyl)piperazine-1-carbonyl]phenyl]-5-[1-[5-[[3-keto-3-(methylamino)propyl]amino]-2-pyridyl]-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[[(exo)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-1-methyl-imidazole-2-carboxamide;

5-[1-(5-aminopyrazin-2-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide;

5-[1-(5-amino-3-fluoro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-4-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-6-fluoro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-6-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-4-chloro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; and 5-[1-[5-(2-aminoethylamino)-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide.

In a preferred embodiment, the present invention provides a compound of formula (I) as described herein, or a pharmaceutically acceptable salt thereof, wherein said compound of formula (I) is selected from:

N-[3-Chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[4-[(2S,3S)-3-hydroxy-1,1-dimethyl-pyrrolidin-1-ium-2-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(3-hydroxy-1,1-dimethyl-piperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3R,4R)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S,4R)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3R,4S)-3-hydroxy-1,1-dimethyl-piperidin-1-ium-4-carbonyl]piperazine-1-carbonyl]phenyl]-1-methyl-imidazole-2-carboxamide;

N-[3-Chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

5-[1-[5-(2-aminoethylamino)-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; and 5-[1-(5-amino-6-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide.

In one embodiment, the present invention provides a compound of formula (I) as described herein, wherein said compound of formula (I) is selected from:

Example A1

N-[3-Chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide; formate Example A2

6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]pyridine-3-carboxamide; formate Example A3

6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]-N-methyl-pyridine-3-carboxamide; formate Example A4

N-[3-chloro-4-[4-(1,1-dimethylpiperidin-1-ium-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide; formate Example A5

5-[1-(5-amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate Example A6

N-[3-chloro-4-[4-[2-[(3R)-3-hydroxy-1-methyl-pyrrolidin-1-ium-1-yl]acetyl]piperazine-1-carbonyl]phenyl]-1- methyl-5-[1-pyrimidin-2-yl-3-(trifluoromethyl)pyrazol-4-yl]imidazole-2-carboxamide; formate Example A7

N-[3-chloro-4-[4-[2-[(3R)-3-hydroxy-1-methyl-pyrrolidin-1-ium-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide; formate Example B1

N-[3-Chloro-4-[4-(1,1-dimethylpiperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide; formate Example B2

N-[3-chloro-4-[4-[(2S,4R)-4-hydroxy-1,1-dimethyl-pyrrolidin-1-ium-2-carbonyl]piperazine-1-carbonyl]phenyl]-1-methyl-5-[1-pyrimidin-2-yl-3-(trifluoromethyl)pyrazol-4-yl]imidazole-2-carboxamide; formate Example B3

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-pyrimidin-2-yl-3-(trifluoromethyl)pyrazol-4-yl]imidazole-2-carboxamide; formate Example B4

N-[3-chloro-4-[4-(3-hydroxy-1,1-dimethyl-piperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide; formate Example B5

N-[3-chloro-4-[4-[(3S,4R)-3-hydroxy-1,1-dimethyl-piperidin-1-ium-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide Example B6

N-[3-chloro-4-[4-[(2S,4R)-4-hydroxy-1,1-dimethyl-pyrrolidin-1-ium-2-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide; formate Example B7

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide; formate Example C1

N-[4-[4-[1-(Azetidin-3-ylmethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;formate Example C2

N-[4-[4-[1-(2-amino-2-oxo-ethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formate Example D1

5-[1-(5-Amino-2-pyridyl)-3-(trifluoromethyl)pyrazol-4-yl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide; formate Example D2

5-[1-(5-amino-2-pyridyl)-3-(trifluoromethyl)pyrazol-4-yl]-N-[3-chloro-4-[4-[(2S,3S)-3-hydroxy-1,1-dimethyl-pyrrolidin-1-ium-2-carbonyl]piperazine-1-carbonyl]phenyl]-1-methyl-imidazole-2-carboxamide; formate Example D3

5-[1-(5-amino-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate Example D4

5-[1-(5-amino-2-pyridyl)-3-(trifluoromethyl)pyrazol-4-yl]-N-[3-chloro-4-[4-(3-hydroxy-1,1-dimethyl-piperidin-1-ium-4-carbonyl)piperazine-1-carbonyl]phenyl]-1-methyl-imidazole-2-carboxamide; formate Example D5

5-[1-(5-amino-2-pyridyl)-3-(trifluoromethyl)pyrazol-4-yl]-N-[3-chloro-4-[4-[(3R,4R)-3-hydroxy-1,1-dimethyl-piperidin-1-ium-4-carbonyl]piperazine-1-carbonyl]phenyl]-1-methyl-imidazole-2-carboxamide; formate Example D6

5-[1-(5-amino-2-pyridyl)-3-(trifluoromethyl)pyrazol-4-yl]-N-[3-chloro-4-[4-[(3S,4R)-3-hydroxy-1,1-dimethyl-piperidin-1-ium-4-carbonyl]piperazine-1-carbonyl]phenyl]-1-methyl-imidazole-2-carboxamide; formate Example D7

5-[1-(5-amino-2-pyridyl)-3-(trifluoromethyl)pyrazol-4-yl]-N-[3-chloro-4-[4-[(3S,4S)-3-hydroxy-1,1-dimethyl-piperidin-1-ium-4-carbonyl]piperazine-1-carbonyl]phenyl]-1-methyl-imidazole-2-carboxamide; formate Example D8

5-[1-(5-amino-2-pyridyl)-3-(trifluoromethyl)pyrazol-4-yl]-N-[3-chloro-4-[4-[(3R,4S)-3-hydroxy-1,1-dimethyl-piperidin-1-ium-4-carbonyl]piperazine-1-carbonyl]phenyl]-1-methyl-imidazole-2-carboxamide; formate Example D10

5-[1-(5-amino-2-pyridyl)-3-(trifluoromethyl)pyrazol-4-yl]-N-[3-chloro-4-[4-(4-hydroxy-1,1-dimethyl-piperidin-1-ium-4-carbonyl)piperazine-1-carbonyl]phenyl]-1-methyl-imidazole-2-carboxamide; formate Example D11

5-[1-(5-amino-2-pyridyl)-3-(trifluoromethyl)pyrazol-4-yl]-N-[3-chloro-4-[4-[2-(3-hydroxy-1-methyl-pyrrolidin-1- ium-1-yl)acetyl]piperazine-1-carbonyl]phenyl]-1-methyl-imidazole-2-carboxamide; formate Example D12

5-[1-(5-amino-2-pyridyl)-3-(trifluoromethyl)pyrazol-4-yl]-N-[3-chloro-4-[[1-(1,1-dimethylpiperidin-1-ium-4-carbonyl)-4-piperidyl]methylcarbamoyl]phenyl]-1-methyl-imidazole-2-carboxamide; formate Example D13

5-[1-(5-amino-2-pyridyl)-3-(trifluoromethyl)pyrazol-4-yl]-N-[3-chloro-4-[4-[(3S)-4,4-dimethylmorpholin-4-ium-3-carbonyl]piperazine-1-carbonyl]phenyl]-1-methyl-imidazole-2-carboxamide; formate Example D14

N-[4-[4-[(2S,3S)-3-[(5-amino-2-pyridyl)oxy]-1,1-dimethyl-pyrrolidin-1-ium-2-carbonyl]piperazine-1-carbonyl]-3-chloro-phenyl]-5-[1-(5-amino-2-pyridyl)-3-(trifluoromethyl)pyrazol-4-yl]-1-methyl-imidazole-2-carboxamide; formate Example D15

5-[1-(5-Amino-2-pyridyl)-3-(trifluoromethyl)pyrazol-4-yl]-N-[3-chloro-4-[4-[(2S)-4-hydroxy-1,1-dimethyl-piperidin-1-ium-2-carbonyl]piperazine-1-carbonyl]phenyl]-1-methyl-imidazole-2-carboxamide;formate Example E1

N-[3-Chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate Example E2

N-[3-chloro-4-[4-(1,1-dimethylpiperidin-1-ium-4-carbonyl) piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide; formate Example E3

N-[3-chloro-4-[4-(1,1-dimethylpiperidin-1-ium-4-carbonyl) piperazine-1-carbonyl]phenyl]-5-[1-[5-(ethylamino)-2-pyridyl]-3-(trifluoromethyl)pyrazol-4-yl]-1-methyl-imidazole-2-carboxamide; formate Example E4

N-[3-chloro-4-[4-(4-hydroxy-1,1-dimethyl-piperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate Example E5

N-[3-chloro-4-[4-[2-(3-hydroxy-1-methyl-pyrrolidin-1-ium-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate Example E6

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate Example E7

N-[4-[4-(1,1-dimethylpiperidin-1-ium-4-carbonyl)piperazine-1-carbonyl]-3-methyl-phenyl]-1-methyl-5-[1-[5-(methylamino)-2-pyridyl]-3-(trifluoromethyl)pyrazol-4-yl]imidazole-2-carboxamide; formate Example E8

N-[3-chloro-4-[4-[(3S,4R)-3-hydroxy-1,1-dimethyl-piperidin-1-ium-4-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate Example F1

N-[3-Chloro-4-[4-(1,1-dimethylpiperidin-1-ium-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide; formate Example G1

N-[3-Chloro-4-[4-(1,1-dimethylpiperidin-1-ium-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formate Example H1

5-[1-(5-Amino-2-pyridyl)-3-(trifluoromethyl)pyrazol-4-yl]-N-[3-chloro-4-[4-(4,4-dimethylpiperazin-4-ium-1-carbonyl)piperidine-1-carbonyl]phenyl]-1-methyl-imidazole-2-carboxamide; formate Example H2

5-[1-(5-amino-2-pyridyl)-3-(trifluoromethyl)pyrazol-4-yl]-N-[3-chloro-4-[4-[3-(hydroxymethyl)-4,4-dimethyl-piperazin-4-ium-1-carbonyl]piperidine-1-carbonyl]phenyl]-1-methyl-imidazole-2-carboxamide; formate Example I1

5-[1-(5-Amino-2-pyridyl)-3-(trifluoromethyl)pyrazol-4-yl]-N-[3-chloro-4-[4-[(4,4-dimethyl-2-oxo-piperazin-4-ium-1-yl)methyl]piperidine-1-carbonyl]phenyl]-1-methyl-imidazole-2-carboxamide; formate Example J1

5-[1-(5-Amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate Example J2

5-[1-(5-amino-2-pyridyl)-3-cyano-pyrazol-4-yl]-N-[3-chloro-4-[4-(1,1-dimethylpiperidin-1-ium-4-carbonyl)

piperazine-1-carbonyl]phenyl]-1-methyl-imidazole-2-carboxamide; 2,2,2-trifluoroacetate Example J3

5-[1-(5-amino-2-pyridyl)-3-methyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate Example J4

5-[1-(5-amino-2-pyridyl)-3-ethyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate Example K1

5-[1-(6-Aminopyridazin-3-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate Example K2

N-[3-chloro-4-[4-(1,1-dimethylpiperidin-1-ium-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide; 2,2,2-trifluoroacetate; and Example L1

5-[1-[5-[(3-Amino-3-oxo-propyl)amino]-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;formate.

In a preferred embodiment, the present invention provides a compound of formula (I) as described herein, wherein said compound of formula (I) is selected from:

Example A1

N-[3-Chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide; formate Example A7

N-[3-chloro-4-[4-[2-[(3R)-3-hydroxy-1-methyl-pyrrolidin-1-ium-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide; formate Example B6

N-[3-chloro-4-[4-[(2S,4R)-4-hydroxy-1,1-dimethyl-pyrrolidin-1-ium-2-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide; formate Example D2

5-[1-(5-amino-2-pyridyl)-3-(trifluoromethyl)pyrazol-4-yl]-N-[3-chloro-4-[4-[(2S,3S)-3-hydroxy-1,1-dimethyl-pyrrolidin-1-ium-2-carbonyl]piperazine-1-carbonyl]phenyl]-1-methyl-imidazole-2-carboxamide; formate Example D3

5-[1-(5-amino-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate Example D4

5-[1-(5-amino-2-pyridyl)-3-(trifluoromethyl)pyrazol-4-yl]-N-[3-chloro-4-[4-(3-hydroxy-1,1-dimethyl-piperidin-1-ium-4-carbonyl)piperazine-1-carbonyl]phenyl]-1-methyl-imidazole-2-carboxamide; formate Example D5

5-[1-(5-amino-2-pyridyl)-3-(trifluoromethyl)pyrazol-4-yl]-N-[3-chloro-4-[4-[(3R,4R)-3-hydroxy-1,1-dimethyl-piperidin-1-ium-4-carbonyl]piperazine-1-carbonyl]phenyl]-1-methyl-imidazole-2-carboxamide; formate Example D6

5-[1-(5-amino-2-pyridyl)-3-(trifluoromethyl)pyrazol-4-yl]-N-[3-chloro-4-[4-[(3S,4R)-3-hydroxy-1,1-dimethyl-piperidin-1-ium-4-carbonyl]piperazine-1-carbonyl]phenyl]-1-methyl-imidazole-2-carboxamide; formate Example D8

5-[1-(5-amino-2-pyridyl)-3-(trifluoromethyl)pyrazol-4-yl]-N-[3-chloro-4-[4-[(3R,4S)-3-hydroxy-1,1-dimethyl-piperidin-1-ium-4-carbonyl]piperazine-1-carbonyl]phenyl]-1-methyl-imidazole-2-carboxamide; formate Example E1

N-[3-Chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate; and Example E6

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate.

In one embodiment, the present invention provides pharmaceutically acceptable salts of the compounds of formula (I) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides compounds according to formula (I) as described herein (i.e., as “free bases” or “free acids”, respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

In one aspect, the present invention provides a process of manufacturing the compounds of formula (I) described herein.

In a further aspect, the present invention provides a compound of formula (I) as described herein, or a pharmaceutically acceptable salt thereof, when manufactured according to the processes described herein.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 3rd Edition, Richard C. Larock. John Wiley & Sons, New York, NY 2018). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered.

Starting materials are either commercially available or can be prepared by methods analogous to the methods given below, by methods described in references cited in the description or in the examples, or by methods known in the art.

The following abbreviations are used in the present text:

ACN or MeCN Acetonitrile
BINAP 2,2'-Bis(diphenylphosphino)-1,1'-binaphthalene
Boc t-Butyloxycarbonyl
CFU colony-forming unit
d day
DCM dichloromethane
DIPEA N,N-diisopropylethylamine
EtOAc or EA Ethyl acetate
FA Formic acid
h(s) or hr(s) hour
HATU: 1-[Bis(dimethylamino)methylene]-1H-1,2,3-triazolo[4,5-b]pyridinium 3-oxid hexafluorophosphate
HPLC: high performance liquid chromatography
HPLC-UV: high performance liquid chromatography with ultraviolet detector
IC50 half maximal inhibitory concentration
IC90 90% inhibitory concentration
NaBH3CN Sodium cyanoborohydride
PE petroleum ether
PdCl2(DPPF) [1,1'-Bis(diphenylphosphino)ferrocene]dichloropalladium(II)
Pd2(dba)3 Tris(dibenzylideneacetone)dipalladium(0)
PG protective group
Precat precatalyst
prep-HPLC preparative high performance liquid chromatography
rt room temperature
sat saturated
SEM 2-methoxyethyl(trimethyl)silane
FA Formic acid
TEMPO (2,2,6,6-Tetramethylpiperidin-1-yl)oxyl
TFA Trifluoroacetic Acid
wt weight
X—PHOS 2-Dicyclohexylphosphino-2',4',6'-triisopropylbiphenyl.

Scheme 1

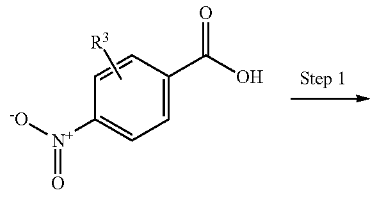

A

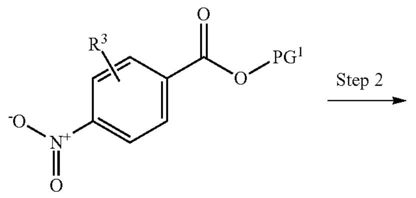

B

-continued

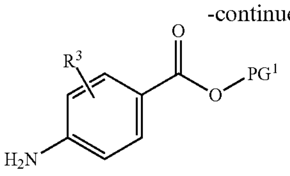

C

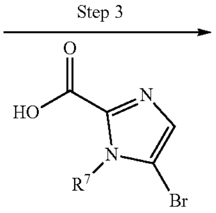

D

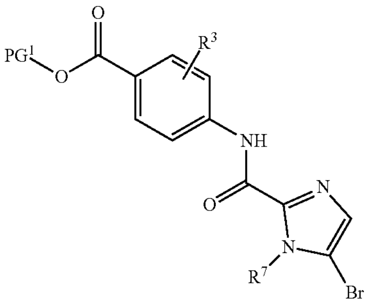

Intermediate B1

Wherein $PG^1$ is a protective group, e.g. a Boc protective group and $R^3$ and $R^7$ are as defined herein;

Compound of formula Intermediate B1 can be prepared according to the synthetic route outlined in Scheme 1. Protection of $R^3$-substituted 4-nitrobenzoic acid A with $(Boc)_2O$ gives compound B. Reduction of the nitro group of compound B can be achieved for example using an ammonium chloride/iron system at room temperature to give amine C. Coupling of D and amine C with a condensing agent, such as HATU/DIPEA in DMSO, affords the compound of formula Intermediate B1.

Scheme 2

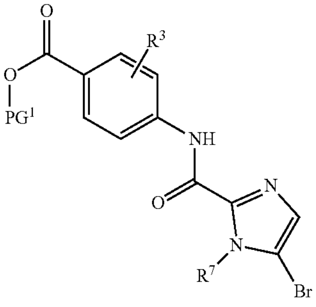

Intermediate B1

-continued

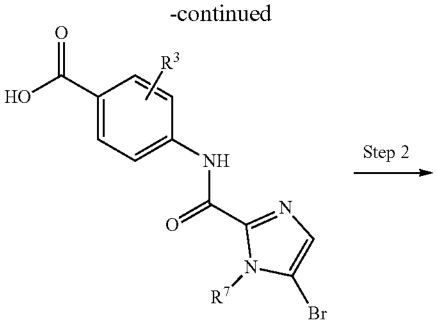

E

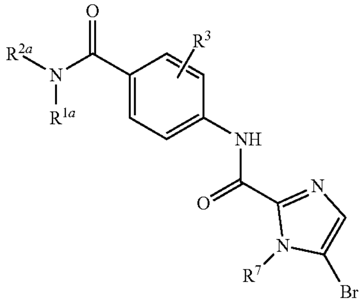

Intermediate B

Wherein $PG^1$, $PG^2$ and $PG^3$ are protective groups, in particular Boc protective groups;

$R^{1a}$ and $R^{2a}$, taken together with the nitrogen atom to which they are attached, form a group of formula (IV), (V) or (VI):

(IV)

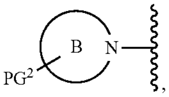

, (V)

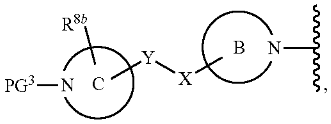

, (VI)

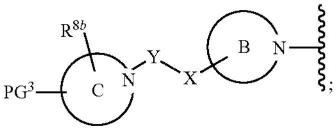

;

or $R^{1a}$ is a group

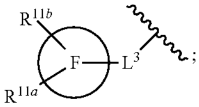

;

and $R^{2a}$ is selected from hydrogen and $C_1$-$C_6$-alkyl; and $R^3$, $R^7$, $R^{8a}$, $R^{8b}$, $R^{11a}$, $R^{11b}$, B, C, F, X, Y and $L^3$ are as defined herein.

Compound of formula Intermediate B can be prepared according to Scheme 2. Hydrolysis of Intermediate B1 gives acid E, which can be couple with diverse amines in the presence of a condensing agent, such as HATU/DIPEA in DMSO, to afford Intermediate B.

Scheme 3

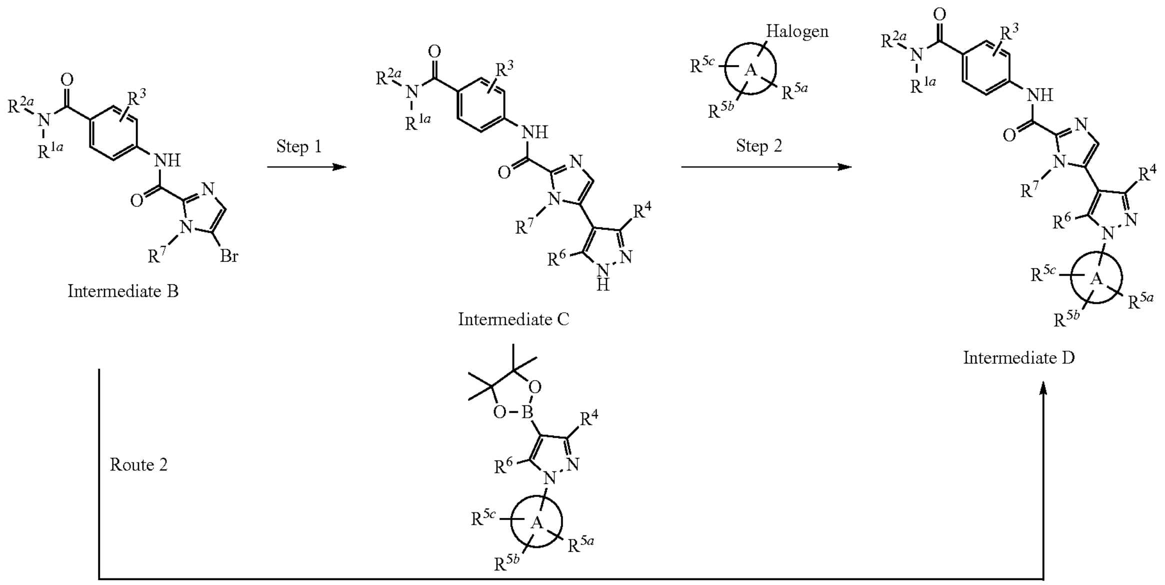

Wherein $PG^1$, $PG^2$ and $PG^3$ are protective groups, e.g. Boc protective groups;

$R^{1a}$ and $R^{2a}$, taken together with the nitrogen atom to which they are attached, form a group of formula (IV), (V) or (VI):

(IV)

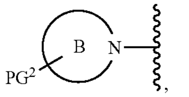

(V)

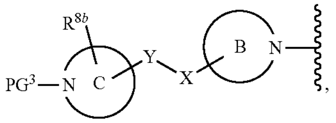

(VI)

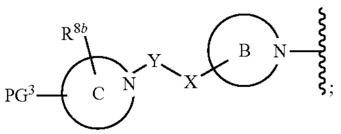

or $R^{1a}$ is a group

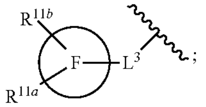

and $R^{2a}$ is selected from hydrogen and $C_1$-$C_6$-alkyl; and $R^3$, $R^4$, $R^{5a}$, $R^{5b}$, $R^{5c}$, $R^6$, $R^7$, $R^{8a}$, $R^{8b}$, $R^{11a}$, $R^{11b}$, A, B, C, F, X, Y and $L^3$ are as defined herein.

Compound of formula Intermediate C and D can be prepared according to Scheme 3. Suzuki coupling of Intermediate B with pyrazole boronic esters can be achieved using palladium catalysts and phosphine ligands to give Intermediate C. This compound can be coupled further with halogen substituted heteroaryls under conditions known in the art, for example 100° C. (microwave) for 2 h in the presence of a base like $K_2CO_3$ in a solvent like MeCN to give Intermediate D (Route 1 in Scheme 3). Intermediate D can also be prepared through a Suzuki coupling reaction of Intermediate B with a heteroaryl substituted pyrazole bronic esters (Route 2 in Scheme 3).

In some case, the order of Suzuki coupling in Scheme 3 and amidation reaction in Scheme 2 could be reversed.

Scheme 4

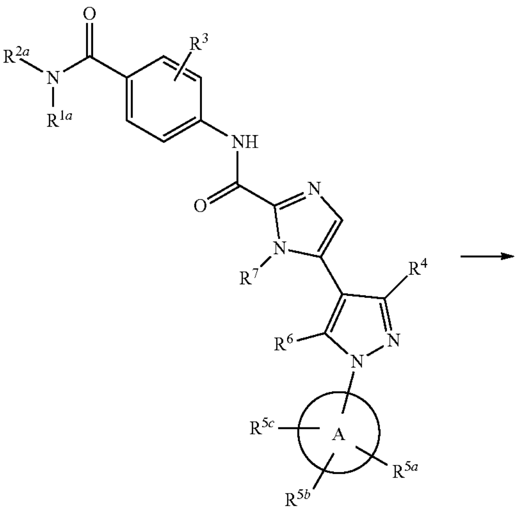

Intermediate D

-continued

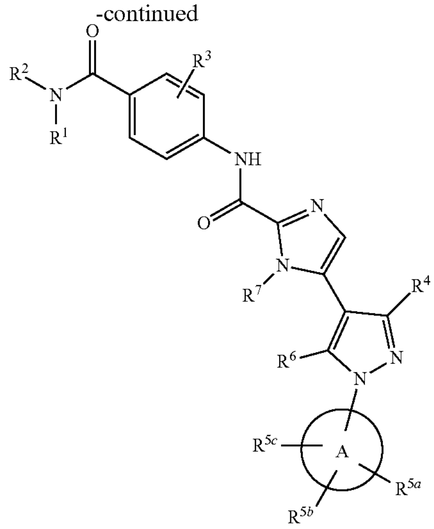

Example A to M

Wherein $PG^1$, $PG^2$ and $PG^3$ are protective groups, such as Boc groups;

$R^{1a}$ and $R^{2a}$, taken together with the nitrogen atom to which they are attached, form a group of formula (IV), (V) or (VI):

(IV)

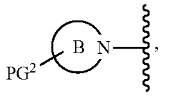

(V)

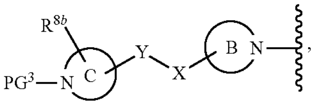

(VI)

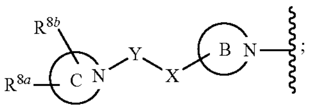

or $R^{1a}$ is a group

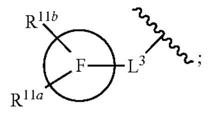

and $R^{2a}$ is selected from hydrogen and $C_1$-$C_6$-alkyl; and $R^1$, $R^2$, $R^3$, $R^4$, $R^{5a}$, $R^{5b}$, $R^{5c}$, $R^6$, $R^7$, $R^{8a}$, $R^{8b}$, $R^{11a}$, $R^{11b}$, A, B, C, F, X, Y and $L^3$ are as defined herein.

Compound of formula Example A to L can be prepared according to Scheme 4. The methylation of Intermediate D can be achieved at conditions like MeI with DIPEA in acetonitrile at room temperature to give Example A to L. The removal of the protective group (if there is one) can be before or after the methylation step, based on different substitution.

Using the Compounds of the Invention

As illustrated in the experimental section, the compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii*.

The compounds of formula (I) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii*.

The compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii*.

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In one aspect, the present invention provides compounds of formula (I) or their pharmaceutically acceptable salts as described herein for use as therapeutically active substances.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a particular embodiment, said nosocomial infections and resulting diseases are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by Gram-negative bacteria.

In a particular embodiment, said infections and resulting diseases caused by Gram-negative bacteria are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present invention provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, which method comprises administering a compound of formula (I) as described herein, or a pharmaceutically acceptable salt thereof, to a mammal.

In a further aspect, the present invention provides the use of a compound of formula (I) as described herein, or a pharmaceutically acceptable salt thereof, as an antibiotic.

In a further aspect, the present invention provides the use of a compound of formula (I) as described herein, or a pharmaceutically acceptable salt thereof, for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present invention provides the use of a compound of formula (I) as described herein, or a pharmaceutically acceptable salt thereof, for the preparation of medicaments useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a particular embodiment, said infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, are selected from bacteremia, pneumonia, meningitis, urinary tract infection and wound infection, or a combination thereof.

In a further aspect, the present invention provides compounds of formula (I) or their pharmaceutically acceptable salts as defined above for use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In a further aspect, the present invention provides a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering a compound of formula (I) or a pharmaceutically acceptable salt thereof as defined above to a mammal.

In a further aspect, the present invention provides the use of compounds of formula (I) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In a further aspect, the present invention provides the use of compounds of formula (I) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (I) or their pharmaceutically acceptable salts as defined above.

Pharmaceutical Compositions and Administration

In one aspect, the present invention provides pharmaceutical compositions comprising compounds of formula (I) or their pharmaceutically acceptable salts as defined above and one or more pharmaceutically acceptable excipients. Exemplary pharmaceutical compositions are described in Examples 1 to 4.

In a further aspect, the present invention relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

Co-Administration of Compounds of Formula (I) and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with an antibiotic, in particular with an antibiotic for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including antibiotic agents. If the administration is not simultaneous, the compounds are administered in a close time proximity to each other. Furthermore, it does not matter if the compounds are administered in the same dosage form, e.g. one compound may be administered intravenously and another compound may be administered orally.

Typically, any agent that has antimicrobial activity may be co-administered. Particular examples of such agents are Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified e.g. in WO 2017072062 A1, WO 2019185572 A1 and WO 2019206853 A1, and Macrolides (erythromycin).

In one aspect, the present invention provides a pharmaceutical composition described herein, further comprising an additional therapeutic agent.

In one aspect, the present invention provides a pharmaceutical combination comprising a compound of formula (I) described herein and an additional therapeutic agent.

In one embodiment, said additional therapeutic agent is an antibiotic agent.

In one embodiment, said additional therapeutic agent is an antibiotic agent that is useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In one embodiment, said additional therapeutic agent is an antibiotic agent selected from Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified in WO 2017072062 A1, WO 2019185572 A1 and WO 2019206853 A1, and Macrolides (erythromycin).

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Intermediate A1

2-Bromo-5-(2-methoxyethoxy)pyridine

In a 50 mL round-bottomed flask, 6-bromopyridin-3-ol (310 mg, 1.8 mmol), 1-bromo-2-methoxyethane (369 mg, 2.65 mmol) and $K_2CO_3$ (367 mg, 2.65 mmol) were refluxed in acetonitrile (5 mL) for 5 h. The crude reaction mixture was concentrated in vacuum. The reaction mixture was poured into 25 mL $H_2O$ and extracted with EtOAc (3×25 mL). The organic layers were combined, washed with sat. NaCl (1×25 mL). The organic layers were dried over anhydrous $Na_2SO_4$ and concentrated in vacuum. The crude material was purified by flash chromatography to afford the title product as light yellow oil (283 mg). MS $[M+H]^+$: 232.2.

Intermediate A2

Benzyl 3-oxo-4-(4-piperidylmethyl)piperazine-1-carboxylate

Step 1: benzyl 4-[(1-tert-butoxycarbonyl-4-piperidyl)methyl]-3-oxo-piperazine-1-carboxylate 3-ketopiperazine-1-carboxylic acid benzyl ester (1.0 g, 4.3 mmol) was dissolved in N,N-dimethylformamide, extra dry (28.5 mL). The solution was cooled to 0° C. To this solution was added portionwise NaH (204.9 mg, 5.1 mmol). The mixture was stirred for 1 h at the same temperature after addition. Then the ice bath was removed and the stirring was continued at rt for 1 h. Then 4-(iodomethyl)piperidine-1-carboxylic acid tert-butyl ester (1.7 g, 5.1 mmol) was added in one time. The stirring was continued for 18 h at rt. The mixture was poured into 100 mL water and extracted with EtOAc (50 mL×3). The extracts were combined, washed with 50 mL brine, dried over sodium sulfate and concentrated in vacuum. The residue was purified by flash chromatography to yield the title compound as light yellow oil, 854 mg. MS $[M+H]^+$: 454.2.

Step 2: benzyl 3-oxo-4-(4-piperidylmethyl)piperazine-1-carboxylate

4-[(1-tert-butoxycarbonyl-4-piperidyl)methyl]-3-keto-piperazine-1-carboxylic acid benzyl ester (850 mg, 2.0 mmol) was dissolved in dichloromethane (4 mL) and 1 mL TFA. The solvent was stirred at rt for 3 h. The solvent was removed in vacuum and the residue was used in the coming step without further purification, light yellow oil, 600 mg. MS $[M+H]^+$: 332.4.

Intermediate A3

9H-Fluoren-9-ylmethyl N-(6-bromo-3-pyridyl)-N-(2-methoxyethyl)carbamate

Step 1: 6-bromo-N-(2-methoxyethyl)pyridin-3-amine

6-Bromopyridin-3-amine (500 mg, 2.89 mmol), sodium iodide (216.6 mg, 1.45 mmol) and 1-Bromo-2-methoxyethane (482.02 mg, 325.91 uL) was dissolved in anhydrous tetrahydrofuran (28.9 mL). The solution was cooled to 0° C.

To this solution was added NaH (138.72 mg, 3.47 mmol) portionwise. The mixture was stirred at 0° C. for 4 h. Then another portion of NaH (138.72 mg, 3.47 mmol) was added, and the mixture was refluxed at 70° C. for 2 h. Then the mixture was cooled to rt and concentrated in vacuum. The residue was purified by flash chromatography to afford 6-bromo-N-(2-methoxyethyl)pyridin-3-amine (373 mg). MS $[M+H]^+$: 231.1.

Step 2: 9H-fluoren-9-ylmethyl N-(6-bromo-3-pyridyl)-N-(2-methoxyethyl)carbamate

A mixture of 6-bromo-N-(2-methoxyethyl)pyridin-3-amine (3.7 g, 16.01 mmol), 9H-fluoren-9-ylmethyl carbonochloridate (4.56 g, 17.61 mmol) and $NaHCO_3$ (2.02 g, 24.02 mmol) were stirred in 1,4-dioxane (80.06 mL) at 0° C. for 18 h. The solvent was removed in vacuum, and the residue was purified by flash chromatography to afford 9H-fluoren-9-ylmethyl N-(6-bromo-3-pyridyl)-N-(2-methoxyethyl)carbamate (6.2 g) as a yellow oil. MS($[M+H]^+$): 453.2.

Intermediate A4

5-Nitro-2-[4-(4,4,5,5-tetramethyl-1,3,2-dioxaborolan-2-yl)-3-(trifluoromethyl)pyrazol-1-yl]pyridine To a solution of 4-(4,4,5,5-tetramethyl-1,3,2-dioxaborolan-2-yl)-3-(trifluoromethyl)-1H-pyrazole (7.8 g, 30 mmol) in dimethy sulfoxide (100 ml) and triethyl amine (3.0 ml) was added 2-chloro-5-nitro-pyridine (4.8 g, 30 mmol). Then the mixture was stirred for 3 h at 130° C. The mixture was poured into water and the aqueous solution was extracted with DCM. The combined organic layers were washed with water and brine, dried over anhydrous $Na_2SO_4$. The organic layer was concentrated in vacuum and the residue was purified by flash column to afford 5-nitro-2-[4-(4,4,5,5-tetramethyl-1,3,2-dioxaborolan-2-yl)-3-(trifluoromethyl)pyrazol-1-yl]pyridine (10 g) as a yellow solid. MS $[M+H]^+$: 385.1.

Intermediate A5

6-[3-(Difluoromethyl)-4-(4,4,5,5-tetramethyl-1,3,2-dioxaborolan-2-yl)pyrazol-1-yl]pyridin-3-amine Step 1: 2-[4-bromo-3-(difluoromethyl)pyrazol-1-yl]-5-nitro-pyridine To a solution of 4-bromo-3-(difluoromethyl)-1H-pyrazole (800.0 mg, 4.06 mmol) in DMF (20.0 mL) was added sodium hydride (243.7 mg, 6.09 mmol) at 0° C. The mixture was stirred at 0° C. for 30 min. Then 2-chloro-5-nitro-pyridine (772.7 mg, 4.87 mmol) was added and the mixture was stirred at 0° C. for 1 h. The mixture was poured into water (50.0 mL) and filtered, the filter cake was washed with water (20.0 mL×3), dried in depressed pressure to give 2-[4-bromo-3-(difluoromethyl)pyrazol-1-yl]-5-nitro-pyridine (1.0 g, 3.13 mmol, 77% yield) as a brown solid. MS($[M+H]^+$): 320.9.

Step 2: 6-[4-bromo-3-(difluoromethyl)pyrazol-1-yl]pyridin-3-amine

To a solution of 2-[4-bromo-3-(difluoromethyl)pyrazol-1-yl]-5-nitro-pyridine (1.0 g, 3.13 mmol) in Acetic acid (50.0 mL) was added iron (1.7 g, 31.34 mmol). The mixture was stirred at 20° C. for 3 h. The reaction mixture was filtered and the filter cake was washed with DCM (20.0 mL). The filtrate was concentrated in vacuum to give a residue, which was purified by silica gel column to give 6-[4-bromo-3-(difluoromethyl)pyrazol-1-yl]pyridin-3-amine (700.0 mg, 2.42 mmol) as a brown solid. MS($[M+2+H]^+$): 290.9.

Step 3: 6-[3-(difluoromethyl)-4-(4,4,5,5-tetramethyl-1,3,2-dioxaborolan-2-yl)pyrazol-1-yl]pyridin-3-amine To a solution of 6-[4-bromo-3-(difluoromethyl)pyrazol-1-yl]pyridin-3-amine (300.0 mg, 1.04 mmol) and bis(pinacolato)diboron (289.9 mg, 1.14 mmol) in 1,4-dioxane (10.0 mL) was added potassium acetate (203.7 mg, 2.08 mmol) and $Pd(dppf)Cl_2$ (113.8 mg, 0.17 mmol) under argon in glove box. The mixture was stirred at 100° C. for 16 h. The reaction mixture was filtered and the filtrate was concentrated in vacuum to give a residue, which was purified by flash column (0.1% FA as additive) and dried by lyophilization to give 6-[3-(difluoromethyl)-4-(4,4,5,5-tetramethyl-1,3,2-dioxaborolan-2-yl)pyrazol-1-yl]pyridin-3-amine (150.0 mg, 0.45 mmol) as a yellow solid MS $[M+H]^+$: 337.1.

Intermediate A6 tert-Butyl N-[6-[3-methoxy-4-(4,4,5,5-tetramethyl-1,3,2-dioxaborolan-2-yl)pyrazol-1-yl]-3-pyridyl]carbamate Step 1: 2-(3-methoxypyrazol-1-yl)-5-nitro-pyridine To a solution of 3-methoxy-1H-pyrazole (0.9 g, 9.17 mmol) in DMF (20.0 mL) was added sodium hydride (550.5 mg, 13.76 mmol) at 0° C. The mixture was stirred at 0° C. for 30 min. 2-chloro-5-nitro-pyridine (1.7 g, 11.01 mmol) was added and the mixture was stirred at 0° C. for 1 h. The reaction mixture was poured into water (50.0 mL) and filtered, The filter cake was washed with water (20.0 mL) and then dried in depressed pressure to give 2-(3-methoxy-pyrazol-1-yl)-5-nitro-pyridine (1.8 g, 8.18 mmol) as a yellow solid. MS $[M+H]^+$: 220.9.

Step 2: 2-(4-bromo-3-methoxy-pyrazol-1-yl)-5-nitro-pyridine

To a solution of 2-(3-methoxypyrazol-1-yl)-5-nitro-pyridine (0.8 g, 3.63 mmol) in DCM (1.0 mL) was added N-bromosuccinimide (0.8 g, 4.49 mmol). The mixture was stirred at 20° C. for 12 h. The reaction mixture was poured into aq. $Na_2S_2O_3$ (10.0 mL) and extracted with EA (100.0 mL×3). The organics was washed with water (50.0 mL×2) then saturated brine solution (50.0 mL). The organics were then separated and dried ($MgSO_4$) before concentration to dryness to give 2-(4-bromo-3-methoxy-pyrazol-1-yl)-5-nitro-pyridine (1.0 g, 3.34 mmol) as a yellow solid. MS([M+2+H]+): 300.9.

Step 3: 6-(4-bromo-3-methoxy-pyrazol-1-yl)pyridin-3-amine

To a solution of 2-(4-bromo-3-methoxy-pyrazol-1-yl)-5-nitro-pyridine (1.0 g, 3.34 mmol) in Acetic acid (30.0 mL) was added iron (1.9 g, 33.44 mmol). The mixture was stirred at 20° C. for 12 h. The reaction mixture was filtered, the filter cake was washed with DCM (20 mL×3) and then the filtrate was concentrated in vacuum and purified by silica gel to give 6-(4-bromo-3-methoxy-pyrazol-1-yl)pyridin-3-amine (800.0 mg, 2.97 mmol) as a brown solid. MS([M+H]$^+$): 268.9.

Step 4: tert-butyl N-[6-(4-bromo-3-methoxy-pyrazol-1-yl)-3-pyridyl]carbamate

To a solution of give 6-(4-bromo-3-methoxy-pyrazol-1-yl)pyridin-3-amine (350.0 mg, 1.30 mmol) in methanol (30.0 mL) was added di-t-butyldicarbonate (567.7 mg, 2.60 mmol). The mixture was stirred at 20° C. for 12 h. The reaction mixture was filtered, the filter cake was washed with DCM (20 mL×3) and then the filtrate was concentrated in vacuum and purified by silica gel column to give tert-butyl N-[6-(4-bromo-3-methoxy-pyrazol-1-yl)-3-pyridyl] carbamate (450 mg, 1.22 mmol) as a brown solid. MS[M+H]$^+$: 369.2.

Step 5: tert-butyl N-[6-[3-methoxy-4-(4,4,5,5-tetramethyl-1,3,2-dioxaborolan-2-yl)pyrazol-1-yl]-3-pyridyl]carbamate To a solution of tert-butyl N-[6-(4-bromo-3-methoxy-pyrazol-1-yl)-3-pyridyl]carbamate (450.0 mg, 1.22 mmol) and 4,4,5,5-tetramethyl-2-(4,4,5,5-tetramethyl-1,3,2-dioxaborolan-2-yl)-1,3,2-dioxaborolane (340.4 mg, 1.34 mmol) in 1,4-dioxane (10.0 mL) was added potassium acetate (239.2 mg, 2.44 mmol) and Pd(dppf)$Cl_2$ (133.6 mg, 0.18 mmol) under argon in glove box. The mixture was stirred at 100° C. for 16 h. The reaction mixture was filtered and the filtrate was concentrated in vacuum to give a residue, which was purified by flash column (0.1% FA as additive) and dried by lyophilization to give tert-butyl N-[6-[3-methoxy-4-(4,4,5,5-tetramethyl-1,3,2-dioxaborolan-2-yl)pyrazol-1-yl]-3-pyridyl]carbamate (150.0 mg, 0.36 mmol) as a yellow solid. MS[M+H]$^+$: 417.3.

Intermediate A7 tert-Butyl N-[6-[3-cyano-4-(4,4,5,5-tetramethyl-1,3,2-dioxaborolan-2-yl)pyrazol-1-yl]-3-pyridyl]carbamate Step 1: 4-bromo-1-(5-nitro-2-pyridyl)pyrazole-3-carbonitrile To a solution of compound 4-bromo-1H-pyrazole-3-carbonitrile (1.0 g, 5.81 mmol) in DMF (8.0 mL) was added N,N-diisopropylethylamine (2.0 mL, 11.63 mmol) and 2-chloro-5-nitro-pyridine (0.7 mL, 6.40 mmol). The mixture was stirred at 80° C. for 12 h under $N_2$. The reaction mixture was quenched by water (10 mL), the residue was filtrated and concentrated under reduced pressure to give 4-bromo-1-(5-nitro-2-pyridyl)pyrazole-3-carbonitrile (1.2 g, 4.08 mmol) as brown solid.

Step 2: 1-(5-amino-2-pyridyl)-4-bromo-pyrazole-3-carbonitrile

To a solution of 4-bromo-1-(5-nitro-2-pyridyl)pyrazole-3-carbonitrile (1.5 g, 5.10 mmol) in acetic acid (20.0 mL) was added Fe (1.4 g, 25.50 mmol). The mixture was stirred at 25° C. for 6 h under $N_2$. The reaction mixture was filtered and the filtrate was concentrated under reduced pressure to remove the solvent, and the crude was purified by chromatography column flash and concentrated to give 1-(5-amino-2-pyridyl)-4-bromo-pyrazole-3-carbonitrile (0.5 g, 1.89 mmol 0) as a white solid. MS[M+H]$^+$: 263.9.

Step 3: tert-butyl N-[6-(4-bromo-3-cyano-pyrazol-1-yl)-3-pyridyl]carbamate

To a solution of 1-(5-amino-2-pyridyl)-4-bromo-pyrazole-3-carbonitrile (0.5 g, 1.89 mmol,) in DMF (5.0 mL) was added di-t-butyldicarbonate (619.8 mg, 2.80 mmol). The mixture was stirred at 25° C. for 12 h under $N_2$, The reaction mixture was added water (25 mL), extracted with EtOAc (20 mL×3). The combined organic layers were washed brine (10 mL), dried over $Na_2SO_4$ and concentrated under reduced pressure to remove the solvent. The crude was then purified by chromatography column flash and concentrated to give tert-butyl N-[6-(4-bromo-3-cyano-pyrazol-1-yl)-3-pyridyl]carbamate (0.5 g, 1.37 mmol) as yellow oil. MS[M+H]$^+$: 366.2.

Step 4: [1-[5-(tert-butoxycarbonylamino)-2-pyridyl]-3-cyano-pyrazol-4-yl]boronic acid A mixture of compound tert-butyl N-[6-(4-bromo-3-cyano-pyrazol-1-yl)-3-pyridyl]carbamate (0.5 g, 1.37 mmol), 4,4,5,5-tetramethyl-2-(4,4,5,5-tetramethyl-1,3,2-dioxaborolan-2-yl)-1,3,2-dioxaborolane (418.4 mg, 1.65 mmol), potassium acetate (0.2 mL, 2.75 mmol) and 1,1'-bis(diphenylphosphino)ferrocene-palladium(II)dichloride dichloromethane complex (112.0 mg, 0.14 mmol) in a flask. 1,4-dioxane (5.0 mL) was added by injector to the mixture. The flask was degassed and purged with $N_2$ gas for four times. The mixture was stirred at 90° C. for 2 h under $N_2$. The reaction mixture was filtered and the filtrate was concentrated under reduced pressure to remove the solvent, then the product was purified by reversed-phase chromatography (0.1% FA as additive) and dried by lyophilization to give [1-[5-(tert-butoxycarbonylamino)-2-pyridyl]-3-cyano-pyrazol-4-yl]boronic acid (268.0 mg, 0.81 mmol,) as a white solid. MS[M+H]$^+$: 330.1.

Intermediate A8 tert-Butyl N-[6-[3-methyl-4-(4,4,5,5-tetramethyl-1,3,2-dioxaborolan-2-yl)pyrazol-1-yl]-3-pyridyl]carbamate Step 1: 2-(4-bromo-3-methyl-pyrazol-1-yl)-5-nitro-pyridine To a solution of 4-bromo-3-methyl-1H-pyrazole (1.0 g, 6.21 mmol) in DMF (8.0 mL) was added NaH (871.3 mg, 9.32 mmol) and 2-chloro-5-nitro-pyridine (0.7 mL, 6.83 mmol) at 0° C. The mixture was stirred at 25° C. for 3 h under $N_2$. The reaction mixture was quenched by water (10 mL), filtered on celite and the filtrate was washed with water and concentrated to give crude product 2-(3-bromopyrazol-1-yl)-5-nitro-pyridine (1.5 g, 5.58 mmol) as yellow solid. MS[M+H]$^+$: 282.9.

Step 2: 6-(4-bromo-3-methyl-pyrazol-1-yl)pyridin-3-amine

To a solution of 2-(3-bromopyrazol-1-yl)-5-nitro-pyridine (1.6 g, 5.83 mmol) in acetic acid (20.0 mL) was added Fe (2.6 g, 46.63 mmol). The mixture was stirred at 25° C. for 12 h under $N_2$. The reaction mixture was filtered and the filtrate was concentrated under reduced pressure to remove the solvent, and the crude was purified by chromatography column flash and concentrated to give 6-(4-bromo-3-methyl-pyrazol-1-yl)pyridin-3-amine (0.6 g, 2.37 mmol) as yellow solid. MS[M+H]$^+$: 254.9.

Step 3: tert-butyl N-[6-(4-bromo-3-methyl-pyrazol-1-yl)-3-pyridyl]carbamate

To a solution of give 6-(4-bromo-3-methyl-pyrazol-1-yl) pyridin-3-amine (250.0 mg, 0.99 mmol) in methanol (0.5 mL) was added di-t-butyldicarbonate (0.3 mL, 1.48 mmol). The mixture was stirred at 25° C. for 12 h under $N_2$. The reaction mixture was concentrated under reduced pressure to remove the solvent to give crude product tert-butyl N-[6-(4-bromo-3-methyl-pyrazol-1-yl)-3-pyridyl]carbamate (280.0 mg, 0.79 mmol). MS[M+H]$^+$: 353.0.

Step 4: tert-butyl N-[6-[3-methyl-4-(4,4,5,5-tetramethyl-1,3,2-dioxaborolan-2-yl)pyrazol-1-yl]-3-pyridyl]carbamate A mixture of tert-butyl N-[6-(4-bromo-3-methyl-pyrazol-1-yl)-3-pyridyl]carbamate (250.0 mg, 0.71 mmol), bis(pinacolato)diboron (179.7 mg, 0.71 mmol), potassium acetate (0.09 mL, 1.42 mmol) and 1,1'-bis(diphenylphosphino)ferrocene-palladium(II)dichloride dichloromethane complex (57.8 mg, 0.07 mmol) in a flask. 1,4-dioxane (5.0 mL) was added by injector to the mixture. The flask was degassed and purged with $N_2$ gas for four times. The mixture was stirred at 90° C. for 2 h under $N_2$. The reaction mixture was filtered and the filtrate was concentrated under reduced pressure to remove the solvent, then the product was purified by reversed-phase chromatography (0.1% FA as additive) and dried by lyophilization to give tert-butyl N-[6-[3-methyl-4-(4,4,5,5-tetramethyl-1,3,2-dioxaborolan-2-yl)pyrazol-1-yl]-3-pyridyl]carbamate (120.0 mg, 0.30 mmol) as white solid. MS[M+H]$^+$: 317.1.

Intermediate A9 tert-Butyl N-[6-[3-ethyl-4-(4,4,5,5-tetramethyl-1,3,2-dioxaborolan-2-yl)pyrazol-1-yl]-3-pyridyl]carbamate Step 1: 2-(3-bromopyrazol-1-yl)-5-nitro-pyridine To a solution of 3-bromo-1H-pyrazole (1.0 g, 6.8 mmol) in THF (20.0 mL) was added sodium hydride, 60% in oil (299.3 mg, 7.48 mmol) slowly at 0° C. After addition, this reaction mixture was stirred at 0° C. for 0.5 h. 2-chloro-5-nitro-pyridine (1.2 g, 7.48 mmol) was added into this mixture at 0° C. The reaction mixture was stirred at 25° C. for 2.5 h. This reaction was quenched by saturated aqueous $NH_4Cl$ (50.0 mL) and was extracted by EtOAc (30.0 mL×3). The combined organic layers were dried over $Na_2SO_4$ and concentrated to get the crude product. This crude product was purified by silica gel chromatography (PE:EtOAc=20:1) to get 2-(3-bromopyrazol-1-yl)-5-nitro-pyridine (1.5 g, 5.58 mmol) as yellow solid. MS[M+H]$^+$: 268.8.

Step 2: 5-nitro-2-(3-vinylpyrazol-1-yl)pyridine

To a solution of 2-(3-bromopyrazol-1-yl)-5-nitro-pyridine (900.0 mg, 3.35 mmol), 4,4,5,5-tetramethyl-2-vinyl-1,3,2-dioxaborolane (772.7 mg, 5.02 mmol) and potassium carbonate (924.6 mg, 6.69 mmol) in 1,4-dioxane (25.0 mL) and water (2.5 mL) was added [1,1'-bis(diphenylphosphino)ferrocene]dichloropalladium(II) (244.7 mg, 0.33 mmol) in one portion under $N_2$. This reaction mixture was stirred at 100° C. for 16 h. This reaction mixture was filtered, and the filtrate was concentrated to get the residue. This residue was diluted with EtOAc (100.0 mL) and was washed by brine (20.0 mL×2). The organic layer was dried over $Na_2SO_4$ and concentrated to get the crude product. This crude product was purified by silica gel chromatography to get 5-nitro-2-(3-vinylpyrazol-1-yl)pyridine (1.1 g, 5.09 mmol) as yellow solid. MS[M+H]$^+$: 217.1.

Step 3: 6-(3-ethylpyrazol-1-yl)pyridin-3-amine

To a solution of 5-nitro-2-(3-vinylpyrazol-1-yl)pyridine (900.0 mg, 4.16 mmol, 1.0 eq) in methanol (5.0 mL) was added palladium on carbon (10%) (443.0 mg, 0.42 mmol, 0.1 eq) in one portion under $N_2$. $H_2$ was introduced into this system. This reaction mixture was stirred at 25° C. for 4 h. This reaction mixture was filtered, and the filtrate was concentrated to get 6-(3-ethylpyrazol-1-yl)pyridin-3-amine (740.0 mg, 3.93 mmol) as colorless oil, which would be used in the next step directly without further purification. MS[M+H]$^+$: 189.2.

Step 4: tert-butyl N-[6-(3-ethylpyrazol-1-yl)-3-pyridyl]carbamate

To a solution of 6-(3-ethylpyrazol-1-yl)pyridin-3-amine (900.0 mg, 4.78 mmol) and triethylamine (1.33 mL, 9.56 mmol) in ACN (20.0 mL) was added di-t-butyldicarbonate (1.32 mL, 5.74 mmol) in one portion. This reaction mixture was stirred at 60° C. for 2 h. This reaction mixture was concentrated to get the crude product. This crude product was purified by silica gel chromatography to get tert-butyl N-[6-(3-ethylpyrazol-1-yl)-3-pyridyl]carbamate (800.0 mg, 2.77 mmol) as yellow oil. MS[M+H]$^+$: 289.2.

Step 5: tert-butyl N-[6-(4-bromo-3-ethyl-pyrazol-1-yl)-3-pyridyl]carbamate

To a solution of tert-butyl N-[6-(3-ethylpyrazol-1-yl)-3-pyridyl]carbamate (700.0 mg, 2.43 mmol) in ACN (20.0 mL) was added N-bromosuccinimide (432.0 mg, 2.43 mmol) in one portion. This reaction mixture was stirred at 25° C. for 2 h. This reaction was quenched by saturated aqueous $Na_2SO_3$ (20.0 mL) and extracted by EtOAc (30.0 mL×2). The combined organic layers were dried over $Na_2SO_4$ and concentrated to get the crude product. This crude product was purified by Prep-HPLC (neutral) to get tert-butyl N-[6-(4-bromo-3-ethyl-pyrazol-1-yl)-3-pyridyl]carbamate (220.0 mg, 0.6 mmol) as red solid. MS[M+H]$^+$: 367.2.

Step 6: tert-butyl N-[6-[3-ethyl-4-(4,4,5,5-tetramethyl-1,3,2-dioxaborolan-2-yl)pyrazol-1-yl]-3-pyridyl]carbamate To a solution of bis(pinacolato)diboron (138.3 mg, 0.54 mmol), tert-butyl N-[6-(4-bromo-3-ethyl-pyrazol-1-yl)-3-pyridyl]carbamate (100.0 mg, 0.270 mmol) and potassium acetate (66.8 mg, 0.68 mmol) in 1,4-dioxane (2.0 mL) was added [1,1'-bis(diphenylphosphino)ferrocene]dichloropalladium(II) (19.9 mg, 0.03 mmol) in one portion under $N_2$. This reaction mixture was stirred at 100° C. for 2 h. This reaction mixture was filtered, and the filtrate was concentrate to get the crude product. This crude product was purified by Prep-TLC (PE:EtOAc=1:1) to get tert-butyl N-[6-[3-ethyl- 4-(4,4,5,5-tetramethyl-1,3,2-dioxaborolan-2-yl)pyrazol-1-yl]-3-pyridyl]carbamate (120.0 mg, 0.29 mmol, 38% yield) as yellow oil. MS obsd. MS[M+H]$^+$: 415.2.

Intermediate A10 tert-Butyl N-[6-[4-(4,4,5,5-tetramethyl-1,3,2-dioxaborolan-2-yl)-3-(trifluoromethyl)pyrazol-1-yl]pyridazin-3-yl]carbamate Step 1: tert-butyl N-(6-chloropyridazin-3-yl)carbamate To a solution of 6-chloropyridazin-3-amine (6.0 g, 46.31 mmol), triethylamine (9.68 mL, 69.47 mmol) and 4-dimethylaminopyridine (2.8 g, 23.16 mmol) in ACN (20.0 mL) was added di-t-butyldicarbonate (15.1 g, 69.47 mmol) in one portion. This reaction mixture was stirred at 80° C. for 16 h. This reaction was quenched by saturated aqueous $Na_2CO_3$ (50.0 mL) and was extracted by EtOAc (100.0 mL×2). The combined organic layers were dried over $Na_2SO_4$ and concentrated to get the crude product. This crude product was purified silica gel chromatography to get tert-butyl N-(6-chloropyridazin-3-yl)carbamate (5.6 g, 24.38 mmol) as light yellow solid. MS([M+H—$C_4H_8$]$^+$:174.1.

Step 2: 6-[4-bromo-3-(trifluoromethyl)pyrazol-1-yl]pyridazin-3-amine

To a solution of tert-butyl N-(6-chloropyridazin-3-yl)carbamate (2.2 g, 9.3 mmol) and potassium carbonate (1.9 g, 13.96 mmol) in DMF (40.0 mL) was added compound 3 (2.0 g, 9.3 mmol) and cesium fluoride (141.3 mg, 0.930 mmol) in one portion. This reaction mixture was stirred at 120° C. for 48 h. This reaction mixture was diluted with EtOAc (200.0 mL) and was washed by brine (50.0 mL×3). The organic layer was dried over $Na_2SO_4$ and concentrated to get the crude product. This crude product was purified by Prep-HPLC (TFA) to get 6-[4-bromo-3-(trifluoromethyl)pyrazol-1-yl]pyridazin-3-amine (350.0 mg, 1.14 mmol) as yellow solid. MS([M+H]$^+$: 308.0.

Step 3: tert-butyl N-[6-[4-bromo-3-(trifluoromethyl)pyrazol-1-yl]pyridazin-3-yl]carbamate To a solution of 6-[4-bromo-3-(trifluoromethyl)pyrazol-1-yl]pyridazin-3-amine (350.0 mg, 1.14 mmol), triethylamine (0.48 mL, 3.41 mmol) and 4-dimethylaminopyridine (138.8 mg, 1.14 mmol) in DMF (10.0 mL) was added di-t-butyldicarbonate (297.5 mg, 1.36 mmol) in one portion. This reaction mixture was stirred at 80° C. for 16 h. This reaction mixture was diluted with brine (20.0 mL) and extracted by EtOAc (10.0 mL×3). The combined organic layers were dried over $Na_2SO_4$ and concentrated to get the crude product. This crude product was purified by Prep-HPLC (FA) to get tert-butyl N-[6-[4-bromo-3-(trifluoromethyl)pyrazol-1-yl]pyridazin-3-yl]carbamate (90.0 mg, 0.22 mmol) as yellow solid. MS([M+2+H]$^+$: 410.0.

Step 4: tert-butyl N-[6-[4-(4,4,5,5-tetramethyl-1,3,2-dioxaborolan-2-yl)-3-(trifluoromethyl)pyrazol-1-yl]pyridazin-3-yl]carbamate To a solution of tert-butyl N-[6-[4-bromo-3-(trifluoromethyl)pyrazol-1-yl]pyridazin-3-yl]carbamate (90.0 mg, 0.220 mmol), bis(pinacolato)diboron (83.9 mg, 0.33 mmol) and potassium acetate (43.2 mg, 0.44 mmol) in 1,4-dioxane (2.0 mL) was added [1,1'-bis(diphenylphosphino)ferrocene]dichloropalladium(II) (16.1 mg, 0.02 mmol) in one portion under $N_2$. This reaction mixture was stirred at 100° C. for 4 h. This reaction mixture was filtered, and the filtrate was concentrated to get the crude product. This crude product was purified by Prep-TLC (PE:EtOAc=4:1) to get tert-butyl N-[6-[4-(4,4,5,5-tetramethyl-1,3,2-dioxaborolan-2-yl)-3-(trifluoromethyl)pyrazol-1-yl]pyridazin-3-yl]carbamate (100.0 mg, 0.22 mmol, 42% yield) as yellow solid. MS([M+H]$^+$: 456.2.

Intermediate A11

Trimethyl-[2-[[4-methyl-3-[4-(4,4,5,5-tetramethyl-1,3,2-dioxaborolan-2-yl)-3-(trifluoromethyl)pyrazol-1-yl]pyrazol-1-yl]methoxy]ethyl]silane Step 1: trimethyl-[2-[(4-methylpyrazol-1-yl)methoxy]ethyl]silane A solution of 4-methyl-1H-pyrazole (5.0 g, 60.9 mmol) in THF (50.0 mL) was degassed and purged with $N_2$ for 3 times. Then sodium hydride (60%) (3.65 g, 91.35 mmol) was added into the mixture at 0° C. This mixture was stirred at 0° C. for 0.5 h. Then 2-(trimethylsilyl)ethoxymethyl chloride (12.9 mL, 73.08 mmol) was added into the mixture at 0° C. The reaction mixture was stirred at 20° C. for 2 h under $N_2$ atmosphere. This reaction was quenched by saturates aqueous $NH_4Cl$ (100.0 mL) and extracted with EtOAc (100.0 mL×3). The combined organic layers were washed with brine (100.0 mL), dried over $Na_2SO_4$, and concentrated under reduced pressure affording the crude product trimethyl-[2-[(4-methylpyrazol-1-yl)methoxy]ethyl]silane (15.0 g, 70.63 mmol) as a yellow solid, which would be used in the next step directly. MS([M+H]$^+$: 213.3.

Step 2: 2-[(3-bromo-4-methyl-pyrazol-1-yl)methoxy]ethyl-trimethyl-silane

A solution of trimethyl-[2-[(4-methylpyrazol-1-yl)methoxy]ethyl]silane (5.0 g, 23.54 mmol) in ACN (50.0 mL) was degassed and purged with $N_2$ for 3 times. Then N-bromosuccinimide (5.0 g, 28.25 mmol) was added into the mixture. The reaction mixture was stirred at 20° C. for 16 h under $N_2$ atmosphere. The mixture was extracted with EtOAc (100.0 mL×3). The combined organic layers were washed with brine (100.0 mL), dried over $Na_2SO_4$, and concentrated under reduced pressure affording the crude product. The crude product was purified by silica gel chromatography (PE:EtOAc=50/1~20/1) to get 2-[(3-bromo-4-methyl-pyrazol-1-yl)methoxy]ethyl-trimethyl-silane (4.4 g, 15.11 mmol) as a yellow oil. MS([M+H]$^+$: 293.0.

Step 3: [4-methyl-1-(2-trimethylsilylethoxymethyl)pyrazol-3-yl]boronic acid

A mixture of 2-[(3-bromo-4-methyl-pyrazol-1-yl)methoxy]ethyl-trimethyl-silane (2.5 g, 8.58 mmol), bis(pinacolato)diboron (5.4 g, 21.46 mmol), potassium acetate (1.61 mL, 25.75 mmol) and X—PHOS (409.1 mg, 0.86 mmol) in 1,4-dioxane (40.0 mL) was degassed and purged with $N_2$ for 3 times. Then tris(dibenzylideneacetone)dipalladium (0) (393.0 mg, 0.43 mmol) was added into the mixture. The reaction mixture was stirred at 100° C. for 16 h under $N_2$ atmosphere. The mixture was filtered and concentrated under reduced pressure affording the crude product. The crude product was purified by Prep-HPLC (TFA) to get [4-methyl-1-(2-trimethylsilylethoxymethyl)pyrazol-3-yl]boronic acid (970.0 mg, 3.79 mmol) as a yellow solid. MS([M+H]$^+$: 257.2.

Step 4: 2-[[3-[4-bromo-3-(trifluoromethyl)pyrazol-1-yl]-4-methyl-pyrazol-1-yl]methoxy]ethyl-trimethyl-silane To a solution of 4-bromo-3-(trifluoromethyl)-1H-pyrazole (400.0 mg, 1.86 mmol), [4-methyl-1-(2-trimethylsilylethoxymethyl)pyrazol-3-yl]boronic acid (572.0 mg, 2.23 mmol), Molecularsieves, 4A (400.0 mg) and pyridine (0.3 mL, 3.72 mmol) in 1,2-dichloroethane (20.0 mL) was added copper(II) acetate monohydrate (74.3 mg, 0.37 mmol) in one portion. Then $O_2$ (15 psi) was introduced into this system. The reaction mixture was stirred at 60° C. for 6 h. This reaction mixture was filtered, and the filtrate was concentrated to get the crude product. This crude product was purified by silica gel chromatography (PE:EtOAc=100:1~50:1) to get 2-[[3-[4-bromo-3-(trifluoromethyl)pyrazol-1-yl]-4-methyl-pyrazol-1-yl]methoxy]ethyl-trimethyl-silane (360.0 mg, 0.85 mmol, 39% yield) as yellow oil. MS([M+H]$^+$: 425.0.

Step 5: trimethyl-[2-[[4-methyl-3-[4-(4,4,5,5-tetramethyl-1,3,2-dioxaborolan-2-yl)-3-(trifluoromethyl)pyrazol-1-yl]pyrazol-1-yl]methoxy]ethyl]silane To a solution of bis(pinacolato)diboron (322.4 mg, 1.27 mmol), 2-[[3-[4-bromo-3-(trifluoromethyl)pyrazol-1-yl]-4-methyl-pyrazol-1-yl]methoxy]ethyl-trimethyl-silane (360.0 mg, 0.85 mmol) and potassium acetate (166.1 mg, 1.69 mmol) in 1,4-dioxane (10.0 mL) was added [1,1'-bis(diphenylphosphino)ferrocene]dichloropalladium(II) (61.9 mg, 0.08 mmol) in one portion under $N_2$. This reaction mixture was stirred at 100° C. for 16 h. This reaction mixture was filtered, and the filtrate was concentrated to get the crude product. This crude product was purified by Prep-TLC (PE:EtOAc=20:1) to get trimethyl-[2-[[4-methyl-3-[4-(4,4,5,5-tetramethyl-1,3,2-dioxaborolan-2-yl)-3-(trifluoromethyl)pyrazol-1-yl]pyrazol-1-yl]methoxy]ethyl]silane (300.0 mg, 0.64 mmol, 40% yield) as yellow oil. MS([M+H]$^+$: 473.0.

Intermediate A12

9H-Fluoren-9-ylmethyl N-(3-amino-3-oxo-propyl)-N-(6-bromo-3-pyridyl)carbamate

Step 1: 6-bromo-N-[3-[tert-butyl(dimethyl)silyl]oxypropyl]pyridin-3-amine (6-bromo-3-pyridyl)amine (2.4 g, 14.2 mmol), 3-[tert-butyl(dimethyl)silyl]oxypropionaldehyde (2.7 g, 14.2 mol) and acetic acid (170.1 mg, 162.1 uL, 2.8 mmol) were dissolved in dichloromethane (50 mL). To this solution was added sodium triacetoxyborohydride (3.6 g, 17.0 mmol) portionwise. The mixture was stirred at rt for 1 h after addition. The mixture was poured into 100 mL water and extracted with DCM (50 mL×2). The extracts were combined, washed with brine and dried over sodium sulfate. The solvent was removed in vacuum and the residue was purified by flash chromatography to give the title compound as light yellow solid, 3.0 g. MS [M+H]$^+$: 345.6.

Step 2: 9H-fluoren-9-ylmethyl N-(6-bromo-3-pyridyl)-N-(3-hydroxypropyl)carbamate (6-bromo-3-pyridyl)-[3-[tert-butyl(dimethyl)silyl]oxypropyl]amine (3.0 g, 8.7 mmol) was dissolved in 5 mL toluene and this solution was added dropwise to a solution of chlorocarbonic acid 9H-fluoren-9-ylmethyl ester (2.2 g, 8.7 mmol) in anhydrous toluene, extra dry (20 mL) at 0° C. After addition, the mixture was stirred at 0° C. for 1 h and then at rt for another 1 h, yellow precipitate formed. The mixture was left overnight. The solvent was removed in vacuum, and the residue was purified by flash chromatography to give the title compound as light yellow oil, 2.0 g. MS [M+H]$^+$: 453.1.

Step 3: 3-[(6-bromo-3-pyridyl)-(9H-fluoren-9-ylmethoxycarbonyl)amino]propanoic acid Iodobenzene diacetate (703.4 mg, 2.2 mmol), TEMPO (62.4 mg, 0.4 mmol) and N-(6-bromo-3-pyridyl)-N-(3-hydroxypropyl)carbamic acid 9H-fluoren-9-ylmethyl ester (900 mg, 2.0 mmol) were combined in a reaction vessel, and to this mixture was added acetonitrile (11 mL) and water (6 mL). The reaction mixtures were stirred for 3 h before another batch of iodobenzene diacetate (703.4 mg, 2.2 mmol) was added. The stirring was continued overnight (~18 h). The solvent was removed in vacuum and the residue was purified by flash chromatography to give the title compound as light yellow foam, 778 mg. MS [M+H]$^+$: 467.1.

Step 4: 9H-fluoren-9-ylmethyl N-(3-amino-3-oxo-propyl)-N-(6-bromo-3-pyridyl)carbamate 3-[(6-bromo-3-pyridyl)-(9H-fluoren-9-ylmethoxycarbonyl)amino]propionic acid (142 mg, 0.3 mmol), ammonium chloride (32.5 mg, 0.6 mmol) and DIEA (196.4 mg, 265.4 uL, 1.5 mmol) were stirred in N,N-dimethylacetamide (5 mL) for 1 min. HATU (138.6 mg, 0.4 mmol) was added to the mixture, and the resulting solution was stirred at 25° C. for 1 h. The mixture was poured into 100 mL water and extracted with EtOAc (50 mL×3). The extracts were combined, washed with 50 mL brine, dried over sodium sulfate and concentrated in vacuum. The residue was purified by flash chromatography to give the title compound as light yellow oil, 114 mg. MS [M+H]$^+$: 466.1.

Intermediate A13

2-[[4-(Methoxymethyl)-3-[4-(4,4,5,5-tetramethyl-1,3,2-dioxaborolan-2-yl)-3-(trifluoromethyl)pyrazol-1-yl]pyrazol-1-yl]methoxy]ethyl-trimethyl-silane Step 1: methyl 1-(2-trimethylsilylethoxymethyl)pyrazole-4-carboxylate To a solution of methyl 1H-pyrazole-4-carboxylate (5.0 g, 39.65 mmol, 1 eq) in THF (100 mL) was added sodium hydride, 60% in oil (1.9 g, 47.58 mmol, 1.2 eq) slowly at 0° C. After addition, the reaction mixture was stirred at 0° C. for 1 h. Then 2-(trimethylsilyl)ethoxymethyl chloride (7.72 mL, 43.61 mmol, 1.1 eq) was added into this mixture at 0° C. The reaction mixture was warmed to 25° C. and was stirred for 15 h. This reaction was quenched by sat. aq. $NH_4Cl$ (100 mL) and was extracted by EtOAc (3×50 mL). The combined organic layers were dried over $Na_2SO_4$ and concentrated. Purification by silica gel chromatography (PE/EtOAc 10:1) gave the title compound (10 g, 39.01 mmol, 79.65% yield) as light yellow oil. MS [M+H]$^+$: 257.0.

Step 2: [1-(2-trimethylsilylethoxymethyl)pyrazol-4-yl]methanol

To a solution of methyl 1-(2-trimethylsilylethoxymethyl)pyrazole-4-carboxylate (5.0 g, 19.5 mmol, 1 eq) in THF (100 mL) was added lithium aluminum hydride (1.11 g, 29.25 mmol, 1.5 eq) slowly at 0° C. After addition, this reaction mixture was stirred at 0° C. for 3 h. This reaction mixture was quenched by $H_2O$ (1 mL) and NaOH (10%, 1 mL) at 0° C. Then $Na_2SO_4$ (5.0 g) was added into this mixture. The mixture was stirred at 25° C. for 1 h. This mixture was filtered, and the filtrate was concentrated to get the crude title compound (5 g, 21.9 mmol, 112% yield) as light yellow oil, which was directly used in the next step without further purification. MS $[M+H]^+$: 229.1.

Step 3: 2-[[4-(methoxymethyl)pyrazol-1-yl]methoxy]ethyl-trimethyl-silane

To a solution of [1-(2-trimethylsilylethoxymethyl)pyrazol-4-yl]methanol (5.0 g, 21.9 mmol, 1 eq) in THE (100 mL) was added sodium hydride, 60% in oil (1.31 g, 32.84 mmol, 1.5 eq) slowly at 0° C. After addition, this reaction mixture was stirred at 0° C. for 1 h. Then iodomethane (1.64 mL, 26.27 mmol, 1.2 eq) was added into this mixture at 0° C. This reaction mixture was stirred at 25° C. for 2 h. This reaction was quenched by $NH_4Cl$ (20 mL) and was extracted by EtOAc (2×30 mL). The combined organic layers were dried over $Na_2SO_4$ and concentrated. Purification by silica gel chromatography (PE/EtOAc 10:1) gave the title compound (3.2 g, 13.2 mmol, 51.93% yield) as light yellow oil. MS $[M+H]^+$: 243.1.

Step 4: 2-[[3-bromo-4-(methoxymethyl)pyrazol-1-yl]methoxy]ethyl-trimethyl-silane To a solution of 2-[[4-(methoxymethyl)pyrazol-1-yl]methoxy]ethyl-trimethyl-silane (1.0 g, 4.13 mmol, 1 eq) in THE (15 mL) was added LDA (4.13 mL, 8.25 mmol, 2 eq) at −78° C. under nitrogen. The mixture was stirred at −78° C. for 1 h. Then 1,2-dibromotetrachloroethane (2.0 g, 6.14 mmol, 1.49 eq) in THE (15 mL) was added at −78° C. The mixture was stirred for 2 h at −78° C. The reaction mixture was poured into aq. HCl (0.5 M, 100 mL) and extracted with EA (3×50 mL). The organics was washed with brine, and dried over $Na_2SO_4$ before concentration to dryness. The crude was then purified by flash column (0.1% FA as additive), and dried by lyophilization to give the title compound (700 mg, 2.18 mmol, 44.2% yield) as light brown oil. MS $[M-CH_2CH_2SiMe_3+H]^+$: 219.0.

Step 5: [4-(methoxymethyl)-1-(2-trimethylsilylethoxymethyl)pyrazol-3-yl]boronic acid A mixture of 2-[[3-bromo-4-(methoxymethyl)pyrazol-1-yl]methoxy]ethyl-trimethyl-silane (3 g, 9.3 mmol, 1 eq), bis(pinacolato)diboron (2.61 g, 10.27 mmol, 1.1 eq), potassium acetate (0.88 mL, 14.01 mmol, 1.5 eq) and X-Phos (890.27 mg, 1.87 mmol, 0.200 eq) in 1,4-dioxane (20 mL) was degassed and purged with $N_2$ for 3 times. Then tris(dibenzylideneacetone)dipalladium (855.04 mg, 0.930 mmol, 0.100 eq) was added to the mixture. The reaction mixture was stirred at 100° C. for 16 h under $N_2$ atmosphere. The mixture was filtered and concentrated. Purification by preparative HPLC (0.1% FA as additive) afforded the title compound (1.7 g, 64%) as a yellow oil. MS $[M+H]^+$: 287.1.

Step 6: 2-[[3-[4-bromo-3-(trifluoromethyl)pyrazol-1-yl]-4-(methoxymethyl)pyrazol-1-yl]methoxy]ethyl-trimethyl-silane A mixture of [4-(methoxymethyl)-1-(2-trimethylsilylethoxymethyl)pyrazol-3-yl]boronic acid (1.2 g, 4.19 mmol, 1 eq), 4-bromo-3-(trifluoromethyl)-1H-pyrazole (1.2 g, 5.58 mmol, 1.33 eq), copper(II) acetate monohydrate (0.84 g, 4.19 mmol, 1 eq), and molecular sieves 4 Å (1.0 g) were added to a flask. The flask was degassed and purged with $N_2$ gas for four times. DMF (14 mL) and pyridine (1.7 mL, 20.96 mmol, 5 eq) were added. The mixture was stirred under oxygen at 80° C. for 16 h. The reaction mixture was filtered, and the filtrate was concentrated in vacuum. The residue was purified by flash column (0.1% FA as additive), and dried by lyophilization to give the title compound (1 g, 2.2 mmol, 52.38% yield) as green oil. MS $[M-30+H]^+$: 425.2.

Step 7: 2-[[4-(methoxymethyl)-3-[4-(4,4,5,5-tetramethyl-1,3,2-dioxaborolan-2-yl)-3-(trifluoromethyl)pyrazol-1-yl]pyrazol-1-yl]methoxy]ethyl-trimethyl-silane To a mixture of 2-[[3-[4-bromo-3-(trifluoromethyl)pyrazol-1-yl]-4-(methoxymethyl)pyrazol-1-yl]methoxy]ethyl-trimethyl-silane (900.0 mg, 1.98 mmol, 1 eq) in THE (9 mL) was added iPrMgCl·LiCl (3.6 mL, 4.68 mmol, 2.37 eq) under nitrogen at 0° C. The mixture was stirred at 20° C. for 2 h. Then 2-isopropoxy-4,4,5,5-tetramethyl-1,3,2-dioxaborolane (489.62 mg, 2.63 mmol, 1.33 eq) was added to the mixture at 0° C. The mixture was stirred at 20° C. for 2 h. The reaction was poured into 0.5 M HCl (50 mL) and extracted with EtOAc (2×50 mL). The combined organics were washed with water (2×50 mL), brine (50 mL), and dried ($MgSO_4$), filtered, and concentrated to give the crude title compound (1500 mg, 2.99 mmol, 99.7% yield) as yellow oil, which was used directly in the next step without further purification. MS $[M-30+H]^+$: 471.4.

Intermediate B1.1 tert-Butyl 4-[(5-bromo-1-methyl-imidazole-2-carbonyl)amino]-2-chloro-benzoate

Step 1: tert-butyl 2-chloro-4-nitro-benzoate

To a mixture of 2-chloro-4-nitro-benzoic acid (15.0 g, 74.42 mmol), N,N-dimethylpyridin-4-amine (2.73 g, 22.33 mmol) and N,N-diethylethanamine (31.12 mL, 223.26 mmol) in THE (80 mL) was added a solution of tert-butoxycarbonyl tert-butyl carbonate (24.36 g, 111.63 mmol) in THE (20 mL) at −10° C. The resulting mixture was warmed to 25° C. and stirred for another 14 h. The mixture was concentrated. The residue was treated with EA (50 mL) and $H_2O$ (50 mL). The mixture was extracted with EA. The combined organic layers were concentrated. The crude was then purified by flash column chromatography to afford tert-butyl 2-chloro-4-nitro-benzoate (18.8 g) as a colorless solid.

Step 2: tert-butyl 4-amino-2-chloro-benzoate

To a mixture of tert-butyl 2-chloro-4-nitro-benzoate (18.8 g, 72.96 mmol) and Ammonium chloride (19.51 g, 364.81 mmol) in ethanol (200 mL) and water (200 mL) was added Iron (20.37 g, 364.81 mmol). The mixture was stirred at 25° C. for 14 h. The mixture was filtered by Celite. The filtrate was concentrated to remove ethanol. The mixture was extracted with EA. The combined organic layers were dried over anhydrous $Na_2SO_4$ and concentrated to afford tert-butyl 4-amino-2-chloro-benzoate (16.31 g) as a light yellow solid. MS $[M+H]^+$: 228.1.

Step 3: tert-butyl 4-[(5-bromo-1-methyl-imidazole-2-carbonyl)amino]-2-chloro-benzoate A mixture of 5-bromo-1-methyl-imidazole-2-carboxylic acid hydrochloride (7.0 g, 28.99 mmol), tert-butyl 4-amino-2-chloro-benzoate (6.0 g, 26.35 mmol), HATU (13.23 g, 34.79 mmol) and DIPEA (16.16 mL, 92.77 mmol) in DMF (15 mL) was stirred at 25° C. for 3 h. The mixture was added water (10 mL) and extracted with EA. The combined organic layers were concentrated. The crude was purified by FCC to afford tert-butyl 4-[(5-bromo-1-methyl-imidazole-2-carbonyl)amino]-2-chloro-benzoate (8 g, 19.29 mmol) as a white solid. MS $[M+H]^+$: 414.0.

The following intermediate was prepared in analogy of intermediate B1.1.

| Ex# | Name | MS ESI $[M + H]^+$ | Starting Material |
|---|---|---|---|
| Intermediate B1.2 | tert-butyl 4-[(5-bromo-1-methyl-imidazole-2-carbonyl)amino]-2-methyl-benzoate | 394.0 | 2-methyl-4-nitro-benzoic acid and 5-bromo-1-methyl-imidazole-2-carboxylic acid |

Intermediate B2.1

5-Bromo-N-[3-chloro-4-(piperazine-1-carbonyl)phenyl]-1-methyl-imidazole-2-carboxamide Step 1: 4-(5-bromo-1-methyl-imidazole-2-carboxamido)-2-chlorobenzoic acid In a 250 mL round-bottomed flask, tert-butyl 4-(5-bromo-1-methyl-imidazole-2-carboxamido)-2-chlorobenzoate (5 g, 12.1 mmol) was combined with $CH_2Cl_2$ (30 mL) to give a light brown solution. TFA (41.2 g, 27.9 mL, 362 mmol) was added. The reaction was stirred at room temperature for 1 h. The crude reaction mixture was concentrated in vacuum to afford 4-(5-bromo-1-methyl-imidazole-2-carboxamido)-2-chlorobenzoic acid (4.32 g). MS $[M+H]^+$: 359.8.

Step 2: tert-butyl 4-(4-(5-bromo-1-methyl-imidazole-2-carboxamido)-2-chlorobenzoyl)piperazine-1-carboxylate In a 100 mL round-bottomed flask, 4-(5-bromo-1-methyl-imidazole-2-carboxamido)-2-chlorobenzoic acid (2 g, 5.58 mmol), tert-butyl piperazine-1-carboxylate (1.19 g, 6.41 mmol,) and DIEA (2.16 g, 2.92 mL, 16.7 mmol) were combined with DMF (15 mL) to give a colorless solution. HATU (2.76 g, 7.25 mmol) was added. The reaction was stirred at room temperature for 1 h. The reaction mixture was poured into 150 mL $H_2O$ and extracted with EtOAc (75 mL×3). The organic layers were combined, washed with sat. NaCl (75 mL×1), The organic layers were dried over $Na_2SO_4$ and concentrated in vacuum to afford tert-butyl 4-(4-(5-bromo-1-methyl-imidazole-2-carboxamido)-2-chlorobenzoyl)piperazine-1-carboxylate (2.94 g,). MS $[M+H]^+$: 527.9.

The following intermediate was prepared in analogy of intermediate B2.1.

| Ex# | Name | MS ESI $[M + H]^+$ | Starting Material |
|---|---|---|---|
| Intermediate B2.2 | tert-butyl 4-[4-[(5-bromo-1-methyl-imidazole-2-carbonyl)amino]-2-methyl-benzoyl]piperazine-1-carboxylate | 506.4 | Intermediate B1.2 and TFA and tert-butyl piperazine-1-carboxylate |
| Intermediate B2.3 | tert-butyl 4-[[[4-[(5-bromo-1-methyl-imidazole-2-carbonyl)amino]-2-chloro-benzoyl]amino]methyl]piperidine-1-carboxylate | 554.8 | Intermediate B1.1 and TFA and tert-butyl 4-(aminomethyl)piperidine-1-carboxylate |

Intermediate B3.1

5-Bromo-N-(3-chloro-4-(piperazine-1-carbonyl) phenyl)-1-methyl-imidazole-2-carboxamide In a 100 mL round-bottomed flask, tert-butyl 4-(4-(5-bromo-1-methyl-imidazole-2-carboxamido)-2-chlorobenzoyl)piperazine-1-carboxylate (2.94 g, 5.58 mmol) was combined with THE (20 mL) to give a light brown solution. HCl (in water) (11.6 mL, 140 mmol) was added. The reaction was stirred at room temperature for 1 h. The crude reaction mixture was concentrated in vacuum. The crude product was directly used to the next step, to afford 5-bromo-N-(3-chloro-4-(piperazine-1-carbonyl)phenyl)-1-methyl-imidazole-2-carboxamide (2.38 g). MS $[M+H]^+$: 427.8.

The following intermediate was prepared in analogy of intermediate B2.1.

| Ex# | Name | MS ESI $[M + H]^+$ | Starting Material |
|---|---|---|---|
| Intermediate B3.2 | 5-bromo-1-methyl-N-[3-methyl-4-(piperazine-1-carbonyl)phenyl]imidazole-2-carboxamide | 406.2 | Intermediate B2.2 and HCl |
| Intermediate B3.3 | 5-bromo-N-[3-chloro-4-(4-piperidylmethylcarbamoyl)phenyl]-1-methyl-imidazole-2-carboxamide | 454.7 | Intermediate B2.3 and HCl |

Intermediate B4 tert-Butyl 4-(4-(4-(5-bromo-1-methyl-imidazole-2-carboxamido)-2-chlorobenzoyl)piperazine-1-carbonyl)piperidine-1-carboxylate In a 100 mL round-bottomed flask, 5-bromo-N-(3-chloro-4-(piperazine-1-carbonyl)phenyl)-1-methyl-imidazole-2-carboxamide (2.38 g, 5.58 mmol), 1-(tert-butoxycarbonyl) piperidine-4-carboxylic acid (2.05 g, 8.92 mmol) and DIEA (2.16 g, 2.92 mL, 16.7 mmol) were combined with DMF (15 mL) to give a light brown solution. HATU (3.39 g, 8.92 mmol) was added. The reaction was stirred at room temperature for 1 h. The reaction mixture was poured into 150 mL $H_2O$ and extracted with EtOAc (50 mL×3). The organic layers were combined, washed with sat NaCl (75 mL×1), The organic layers were dried over $Na_2SO_4$ and concentrated in vacuum. tert-butyl 4-(4-(4-(5-bromo-1-methyl-imidazole-2-carboxamido)-2-chlorobenzoyl)piperazine-1-carbonyl)piperidine-1-carboxylate (3.56 g). MS $[M+H]^+$: 638.9.

The following intermediates were prepared in analogy of intermediate B4.

| Ex# | Name | MS ESI $[M + H]^+$ | Starting Material |
|---|---|---|---|
| Intermediate B5 | tert-butyl 4-[4-[4-[(5-bromo-1-methyl-imidazole-2-carbonyl)amino]-2-chloro-benzoyl]piperazine-1-carbonyl]-4-hydroxy-piperidine-1-carboxylate | 653.2 | Intermediate B3.1 and 1-tert-butoxycarbonyl-4-hydroxy-piperidine-4-carboxylic acid |
| Intermediate D27 | tert-butyl (2S,3S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-3-hydroxy-pyrrolidine-1-carboxylate | 817.2 | Intermediate E1 and (2S,3S)-1-tert-butoxycarbonyl-3-hydroxy-pyrrolidine-2-carboxylic acid |
| Intermediate B7 | 5-bromo-N-[3-chloro-4-[4-(1-methylpiperidine-4-carbonyl)piperazine-1-carbonyl]phenyl]-1-methyl-imidazole-2-carboxamide | 553.1 | Intermediate B3.1 and 1-methylpiperidine-4-carboxylic acid |
| Intermediate B8 | tert-butyl 4-[4-[4-[(5-bromo-1-methyl-imidazole-2-carbonyl)amino]-2-methyl-benzoyl]piperazine-1-carbonyl]piperidine-1-carboxylate | 617.1 | Intermediate B3.2 and 1-(tert-butoxycarbonyl) piperidine-4-carboxylic acid |
| Intermediate B9 | tert-butyl 4-[4-[[[4-[(5-bromo-1-methyl-imidazole-2-carbonyl)amino]-2-chloro-benzoyl]amino]methyl]piperidine-1- | 665.2 | Intermediate B3.3 and 1-(tert-butoxycarbonyl) piperidine-4-carboxylic acid |

-continued

| Ex# | Name | MS ESI $[M + H]^+$ | Starting Material |
| --- | --- | --- | --- |
| Intermediate B10 | tert-butyl (3S)-3-[4-[4-[(5-bromo-1-methyl-imidazole-2-carbonyl)amino]-2-chloro-benzoyl]piperazine-1-carbonyl]morpholine-4-carboxylate | 639.1 | Intermediate B3.1 and (3S)-4-tert-butoxycarbonylmorpholine-3-carboxylic acid |
| Intermediate B11 | tert-butyl (2S,3S)-2-[4-[4-[(5-bromo-1-methyl-imidazole-2-carbonyl)amino]-2-chloro-benzoyl]piperazine-1-carbonyl]-3-hydroxy-pyrrolidine-1-carboxylate | 641.0 | Intermediate B3.1 and (2S,3S)-1-tert-butoxycarbonyl-3-hydroxy-pyrrolidine-2-carboxylic acid |
| Intermediate D28 | tert-butyl (3S,4R)-4-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-3-hydroxy-piperidine-1-carboxylate | 831.2 | Intermediate E1 and rac-(3S,4R)-1-tert-butoxycarbonyl-3-hydroxy-piperidine-4-carboxylic acid |

Intermediate B12 tert-Butyl 1-[4-[(5-bromo-1-methyl-imidazole-2-carbonyl)amino]-2-chloro-benzoyl]piperidine-4-carboxylate Intermediate B 1.1 (1200 mg, 3.2 mmol) was stirred in 20% TFA/DCM solution at rt for 4 h. The solvent was then removed in vacuum. The residue was dissolved in acetonitrile (17 mL). To this solution were added isonipecotic acid tert-butyl ester (744.0 mg, 4.0 mmol), HATU (1.4 g, 3.7 mmol) and DIEA (1.3 g, 1.8 mL, 10.0 mmol). The mixture was stirred at rt for 1 h. The solvent was removed in vacuum, and the residue was purified by flash chromatography to give the title compound as off white solid, 1.65 g. MS $[M+H]^+$: 527.1.

Intermediate C1 tert-Butyl 2-chloro-4-[[1-methyl-5-[3-(trifluoromethyl)-H-pyrazol-4-yl]imidazole-2-carbonyl]amino] benzoate In a 100 mL round-bottomed flask, tert-butyl 4-(5-bromo-1-methyl-imidazole-2-carboxamido)-2-chlorobenzoate (2 g, 4.82 mmol), 4-(4,4,5,5-tetramethyl-1,3,2-dioxaborolan-2-yl)-3-(trifluoromethyl)-1H-pyrazole (1.64 g, 6.27 mmol), 1,1'-bis(di-tert-butylphosphino)ferrocene palladium dichloride (314 mg, 482 μmol) and $Na_2CO_3$ (1.53 g, 14.5 mmol) were combined with 1,4-Dioxane (30 mL) Water (3 mL) and stirred at 100° C. for 15 h under $N_2$. The filtrate was concentrated in vacuum. The crude material was purified by flash chromatography (silica gel, 20 g, 0% to 10% MeOH in DCM) to afford tert-butyl 2-chloro-4-(1-methyl-5-(3-(trifluoromethyl)-1H-pyrazol-4-yl)-imidazole-2-carboxamido) benzoate (2 g). MS $[M+H]^+$: 470.7.

The following intermediates were prepared in analogy of intermediate C1.

| Ex# | Name | MS ESI $[M + H]^+$ | Starting Material |
| --- | --- | --- | --- |
| Intermediate C2 | tert-butyl 4-(2-chloro-4-(1-methyl-5-(3-(trifluoromethyl)-1H-pyrazol-4-yl)-imidazole-2-carboxamido)benzoyl)piperazine-1-carboxylate | 582.2 | Intermediate B2.1 and 4-(4,4,5,5-tetramethyl-1,3,2-dioxaborolan-2-yl)-3-(trifluoromethyl)-1H-pyrazole |
| Intermediate C3 | tert-butyl 4-(4-(2-chloro-4-(1-methyl-5-(3-(trifluoromethyl)-1H-pyrazol-4-yl)-imidazole-2-carboxamido)benzoyl)piperazine-1-carbonyl)piperidine-1-carboxylate | 693.3 | Intermediate B4 and 4-(4,4,5,5-tetramethyl-1,3,2-dioxaborolan-2-yl)-3-(trifluoromethyl)-1H-pyrazole |

-continued

| Ex# | Name | MS ESI [M + H]$^+$ | Starting Material |
|---|---|---|---|
| Intermediate C4 | tert-butyl (2S,3S)-2-[4-[2-chloro-4-[[1-methyl-5-[3-(trifluoromethyl)-1H-pyrazol-4-yl]imidazole-2-carbonyl]amino]benzoyl]piperazine-1-carbonyl]-3-hydroxy-pyrrolidine-1-carboxylate | 595.3 | Intermediate B12 and 4-(4,4,5,5-tetramethyl-1,3,2-dioxaborolan-2-yl)-3-(trifluoromethyl)-1h-pyrazole |
| Intermediate D14 | tert-butyl 1-[2-chloro-4-[[1-methyl-5-[1-(5-nitro-2-pyridyl)-3-(trifluoromethyl)pyrazol-4-yl]imidazole-2-carbonyl]amino]benzoyl]piperidine-4-carboxylate | 703.1 | Intermediate B12 and Intermediate A4 |
| Intermediate D15 | tert-butyl 2-chloro-4-[[1-methyl-5-[1-(5-nitro-2-pyridyl)-3-(trifluoromethyl)pyrazol-4-yl]imidazole-2-carbonyl]amino]benzoate | 592.2 | Intermediate B1.1 and Intermediate A4 |
| Intermediate D16 | tert-butyl 4-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-4-hydroxy-piperidine-1-carboxylate | 831.2 | Intermediate B5 and Intermediate A4 |
| Intermediate D17 | 5-[1-(5-amino-2-pyridyl)-3-(difluoromethyl)pyrazol-4-yl]-N-[3-chloro-4-[4-(1-methylpiperidine-4-carbonyl)piperazine-1-carbonyl]phenyl]-1-methyl-imidazole-2-carboxamide | 681.2 | Intermediate B7 and Intermediate A5 |
| Intermediate D18 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-methoxy-pyrazol-1-yl]-3-pyridyl]carbamate | 761.4 | Intermediate B7 and Intermediate A6 |
| Intermediate D19 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-cyano-pyrazol-1-yl]-3-pyridyl]carbamate | 756.2 | Intermediate B7 and Intermediate A7 |
| Intermediate D20 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-methyl-pyrazol-1-yl]-3-pyridyl]carbamate | 745.3 | Intermediate B7 and Intermediate A8 |
| Intermediate D21 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-ethyl-pyrazol-1-yl]-3-pyridyl]carbamate | 759.0 | Intermediate B7 and Intermediate A9 |
| Intermediate D22 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-(trifluoromethyl)pyrazol-1-yl]pyridazin-3-yl]carbamate | 800.2 | Intermediate B7 and Intermediate A10 |
| Intermediate D23 | N-[3-chloro-4-[4-(1-methylpiperidine-4-carbonyl)piperazine-1-carbonyl]phenyl]-1-methyl-5-[1-[4-methyl-1-(2-trimethylsilylethoxymethyl)pyrazol-3-yl]-3-(trifluoromethyl)pyrazol-4-yl]imidazole-2-carboxamide | 817.3 | Intermediate B7 and Intermediate A11 |
| Intermediate D24 | tert-butyl 4-[4-[2-methyl-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]piperidine-1-carboxylate | 795.3 | Intermediate B8 and Intermediate A4 |
| Intermediate D25 | tert-butyl 4-[4-[[[2-chloro-4-[[1-methyl-5-[1-(5-nitro-2-pyridyl)-3-(trifluoromethyl)pyrazol-4-yl]imidazole-2-carbonyl]amino]benzoyl]amino]methyl]piperidine-1-carbonyl]piperidine-1-carboxylate | 843.2 | Intermediate B9 and Intermediate A4 |
| Intermediate D26 | tert-butyl (3S)-3-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]morpholine-4-carboxylate | 817.3 | Intermediate B10 and Intermediate A4 |
| Intermediate D35 | N-[3-chloro-4-[4-(1-methylpiperidine-4-carbonyl)piperazine-1-carbonyl]phenyl]-5-[1-[4-(methoxymethyl)-1-(2-trimethylsilylethoxymethyl)pyrazol-3-yl]-3-(trifluoromethyl)pyrazol-4-yl]-1-methyl-imidazole-2-carboxamide | 847.6 | Intermediate B7 and Intermediate A13 |

Intermediate C5

(exo)-6-[[2-chloro-4-[[1-methyl-5-[3-(trifluoromethyl)-1H-pyrazol-4-yl]imidazole-2-carbonyl]amino]benzoyl]amino]-3-azabicyclo[3.1.0]hexane-3-carboxylic acid tert-butyl ester Step 1: 2,2,2-trifluoroacetic acid compound with 2-chloro-4-(1-methyl-5-(3-(trifluoromethyl)-1H-pyrazol-4-yl)-1H-imidazole-2-carboxamido)benzoic acid In a 50 ml flask tert-butyl 2-chloro-4-(1-methyl-5-(3-(trifluoromethyl)-1H-pyrazol-4-yl)-1H-imidazole-2-carboxamido)benzoate (1.3 g, 2.77 mmol, Eq: 1) was dissolved in DCM (15 ml). TFA (6.31 g, 4.26 ml, 55.3 mmol, Eq: 20) was added. The reaction was stirred at RT. After 2 h, the crude reaction mixture was concentrated in vacuo. The residue was taken up in ~20 mL water. The precipitate was filtered off, washed with water, and dried under HV to afford the title compound (1.23 g, 84%) as an off-white solid. MS $[M-H]^-$: 412.2.

Step 2: (exo)-6-[[2-chloro-4-[[1-methyl-5-[3-(trifluoromethyl)-1H-pyrazol-4-yl]imidazole-2-carbonyl]amino]benzoyl]amino]-3-azabicyclo[3.1.0]hexane-3-carboxylic acid tert-butyl ester A mixture of 2-chloro-4-[[1-methyl-5-[3-(trifluoromethyl)-1H-pyrazol-4-yl]imidazole-2-carbonyl]amino]benzoic acid (550 mg, 1.33 mmol, 1 eq), rac-(exo)-6-amino-3-azabicyclo[3.1.0]hexane-3-carboxylic acid tert-butyl ester (395.33 mg, 1.99 mmol, 1.5 eq) and HATU (758.18 mg, 1.99 mmol, 1.5 eq) were combined with N,N-dimethylformamide, extra dry (10 mL). DIPEA (515.41 mg, 696.5 uL, 3.99 mmol, 3 eq) was added and the reaction mixture was stirred at RT for 2 h. Under cooling with an ice bath, water was added to the reaction mixture. As no product precipitated, the mixture was extracted with ethyl acetate (3×10 mL). The combined organic layers were washed with LiCl solution 5%, and brine. Sodium sulfate was added, and the mixture was filtered, and evaporated to dryness. Purification by flash chromatography (12 g, MeOH/DCM 1:9 in DCM, 0-80%) afforded the title compound (769 mg, 95%) as a white solid. MS $[M-H]^-$: 592.2.

Intermediate C6

(2S,4R)-2-[(exo)-6-[[2-chloro-4-[[1-methyl-5-[3-(trifluoromethyl)-1H-pyrazol-4-yl]imidazole-2-carbonyl]amino]benzoyl]amino]-3-azabicyclo[3.1.0]hexane-3-carbonyl]-4-hydroxy-pyrrolidine-1-carboxylic acid tert-butyl ester Step 1: N-[3-chloro-4-[[rac-(1S,5R)-3-azabicyclo[3.1.0]hexan-6-yl]carbamoyl]phenyl]-1-methyl-5-[3-(trifluoromethyl)-1H-pyrazol-4-yl]imidazole-2-carboxamide; hydrochloride To a solution of tert-butyl rac-(1S,5R)-6-[[2-chloro-4-[[1-methyl-5-[3-(trifluoromethyl)-1H-pyrazol-4-yl]imidazole-2-carbonyl]amino]benzoyl]amino]-3-azabicyclo[3.1.0]hexane-3-carboxylate (730.0 mg, 1.23 mmol, 1 eq) in 1,4-dioxane (10 mL) was added hydrochloric acid in dioxane (14.6 mL, 58.4 mmol, 47.52 eq). The mixture was stirred at 20° C. for 2 h. The mixture was concentrated under vacuum to give the title compound (652 mg, 1.23 mmol, 100.04% yield) as a light yellow solid. MS $[M+H]^+$: 494.1.

Step 2: (2S,4R)-2-[(exo)-6-[[2-chloro-4-[[1-methyl-5-[3-(trifluoromethyl)-1H-pyrazol-4-yl]imidazole-2-carbonyl]amino]benzoyl]amino]-3-azabicyclo[3.1.0]hexane-3-carbonyl]-4-hydroxy-pyrrolidine-1-carboxylic acid tert-butyl ester In a 25 ml round-bottomed flask, N-[3-chloro-4-[[(exo)-3-azabicyclo[3.1.0]hexan-6-yl]carbamoyl]phenyl]-1-methyl-5-[3-(trifluoromethyl)-1H-pyrazol-4-yl]imidazole-2-carboxamide;hydrochloride (135 mg, 0.234 mmol, 1 eq) and (2S,4R)-1-tert-butoxycarbonyl-4-hydroxy-proline (81.24 mg, 0.351 mmol, 1.5 eq) were combined with N,N-dimethylformamide (3 mL) to give a light brown solution. N,N-diisopropylethylamine (46.81 mg, 63.09 uL, 0.362 mmol, 1.55 eq) and HATU (133.57 mg, 0.351 mmol, 1.5 eq) were added, and the reaction mixture was stirred at RT. After 2 h, 1 equiv of each reagent was added, and stirring was continued at RT. After 4 h, water was added, and the mixture was extracted with DCM. The combined organic layers were washed twice with a 5% LiCl solution, brine, and dried over $Na_2SO_4$. After filtration and evaporation of the volatiles, the residue was purified by column chromatography on silica gel (4 g $SiO_2$, 0% to 100% (DCM:MeOH;9:1) in DCM) to give the title compound (156.8 mg, 91.85%) as off-white solid. MS $[M+H]^+$: 707.2.

Intermediate D1 tert-Butyl 4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carboxylate To a 25 mL microwave vial was added tert-butyl 4-(2-chloro-4-(1-methyl-5-(3-(trifluoromethyl)-1H-pyrazol-4-yl)-imidazole-2-carboxamido)benzoyl)piperazine-1-carboxylate (1.5 g, 2.58 mmol), 2-chloro-5-nitropyridine (531 mg, 3.35 mmol) and $K_2CO_3$ (712 mg, 5.15 mmol) in MeCN (18 mL). The vial was capped and heated under microwave at 100° C. for 2 h. The crude reaction mixture was concentrated in vacuum. The reaction mixture was filtered through glass fiber paper. The filtrate was concentrated in vacuum. The crude material was purified by flash chromatography (silica gel, 40 g, 0% to 10% MeOH in DCM) to afford tert-butyl 4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carboxylate (1.4 g). MS $[M+H]^+$: 704.2.

The following intermediates were prepared in analogy of intermediate D1.

| Ex# | Name | MS ESI $[M + H]^+$ | Starting Material |
|---|---|---|---|
| Intermediate D2 | tert-butyl 2-chloro-4-[[1-methyl-5-[1-pyrimidin-2-yl-3-(trifluoromethyl)pyrazol-4-yl]imidazole-2-carbonyl]amino]benzoate | 548.2 | Intermediate C1 and 2-chloropyrimidine |

-continued

| Ex# | Name | MS ESI [M + H]+ | Starting Material |
|---|---|---|---|
| Intermediate D3 | tert-butyl 4-(2-chloro-4-(1-methyl-5-(1-(pyrimidin-2-yl)-3-(trifluoromethyl)-pyrazol-4-yl)-imidazole-2-carboxamido)benzoyl)piperazine-1-carboxylate | 660.4 | Intermediate C2 and 2-chloropyrimidine |
| Intermediate D4 | tert-butyl 4-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)piperidine-1-carboxylate | 815.5 | Intermediate C3 and 2-chloro-5-nitropyridine |
| Intermediate D5 | tert-butyl 4-[4-[4-[[5-[1-(5-carbamoyl-2-pyridyl)-3-(trifluoromethyl) pyrazol-4-yl]-1-methyl-imidazole-2-carbonyl]amino]-2-chloro-benzoyl]piperazine-1-carbonyl]piperidine-1-carboxylate | 813.4 | Intermediate C3 and 6-chloropyridine-3-carboxamide midine |
| Intermediate D6 | tert-butyl 4-[4-[2-chloro-4-[[1-methyl-5-[1-[5-(methylcarbamoyl)-2-pyridyl]-3-(trifluoromethyl)pyrazol-4-yl]imidazole-2-carbonyl]amino]benzoyl]piperazine-1-carbonyl]piperidine-1-carboxylate | 827.3 | Intermediate C3 and 6-chloro-N-methyl-pyridine-3-carboxamide |
| Intermediate D7 | tert-butyl 4-[4-[2-chloro-4-[[5-[1-(5-formyl-2-pyridyl)-3-(trifluoromethyl)pyrazol-4-yl]-1-methyl-imidazole-2-carbonyl]amino]benzoyl]piperazine-1-carbonyl]piperidine-1-carboxylate | 798.3 | Intermediate C3 and 6-chloropyridine-3-carbaldehyde |
| Intermediate D8 | tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidine-1-carboxylate | 771.8 | Intermediate C3 and 2-chloropyrimidine |
| Intermediate D9 | tert-butyl 4-[4-[2-chloro-4-[[5-[1-(5-methoxy-2-pyridyl)-3-(trifluoromethyl)pyrazol-4-yl]-1-methyl-imidazole-2-carbonyl]amino]benzoyl]piperazine-1-carbonyl]piperidine-1-carboxylate | 800.2 | Intermediate C3 and 2-fluoro-5-methoxy-pyridine |
| Intermediate D29 | tert-butyl (2S,3S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-3-[(5-nitro-2-pyridyl)oxy]pyrrolidine-1-carboxylate | 939.2 | Intermediate C4 and 2-chloro-5-nitropyridine |
| Intermediate D31 | tert-butyl 4-[4-[2-chloro-4-[[1-methyl-5-[1-(4-methyl-5-nitro-2-pyridyl)-3-(trifluoromethyl)pyrazol-4-yl]imidazole-2-carbonyl]amino]benzoyl]piperazine-1-carbonyl]piperidine-1-carboxylate | 829.1 | Intermediate C3 and 2-chloro-4-methyl-5-nitropyridine |
| Intermediate D33 | tert-butyl 4-[4-[2-chloro-4-[[1-methyl-5-[1-(6-methyl-5-nitro-2-pyridyl)-3-(trifluoromethyl)pyrazol-4-yl]imidazole-2-carbonyl]amino]benzoyl]piperazine-1-carbonyl]piperidine-1-carboxylate | 829.2 | Intermediate C3 and 6-chloro-2-methyl-3-nitropyridine |
| Intermediate D34 | tert-butyl 4-[4-[4-[[5-[1-(5-amino-4-chloro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate | 719.3, [M + H—BOC]+ | Intermediate C3 and tert-butyl N-(4-chloro-6-fluoro-3-pyridyl)carbamate |
| Intermediate D36 | 4-[4-[2-chloro-4-[[1-methyl-5-[1-(5-nitropyrazin-2-yl)-3-(trifluoromethyl)pyrazol-4-yl]imidazole-2-carbonyl]amino]benzoyl]piperazine-1-carbonyl]piperidine-1-carboxylic acid tert-butyl ester | 816.3 | Intermediate C3 and 2-bromo-5-nitro-pyrazine |

-continued

| Ex# | Name | MS ESI [M + H]+ | Starting Material |
|---|---|---|---|
| Intermediate D37 | (2S,4R)-2-[(1S,5R)-6-[[2-chloro-4-[[1-methyl-5-[1-(5-nitro-2-pyridyl)-3-(trifluoromethyl)pyrazol-4-yl]imidazole-2-carbonyl]amino]benzoyl]amino]-3-azabicyclo[3.1.0]hexane-3-carbonyl]-4-hydroxy-pyrrolidine-1-carboxylic acid tert-butyl ester | 829.2 | Intermediate C6 and 2-bromo-5-nitropyridine |
| Intermediate D38 | (exo)-6-[[2-chloro-4-[[1-methyl-5-[1-(5-nitro-2-pyridyl)-3-(trifluoromethyl)pyrazol-4-yl]imidazole-2-carbonyl]amino]benzoyl]amino]-3-azabicyclo[3.1.0]hexane-3-carboxylic acid tert-butyl ester | 714.5, [M − H]− | Intermediate C5 and 2-bromo-5-nitropyridine |
| Intermediate D39 | tert-butyl 2-chloro-4-(1-methyl-5-(1-(pyrimidin-2-yl)-3-(trifluoromethyl)-1H-pyrazol-4-yl)-1H-imidazole-2-carboxamido)benzoate | 548.2 | Intermediate C1 and 2-chloropyrimidine |

Intermediate D10 tert-Butyl 4-[2-chloro-4-[[5-[1-(5-methoxy-2-pyridyl)-3-(trifluoromethyl)pyrazol-4-yl]-1-methyl-imidazole-2 carbonyl]amino]benzoyl]piperazine-1-carboxylate Under $N_2$ protection, a mixture of tert-butyl 4-[2-chloro-4-[[1-methyl-S-[3-(trifluoromethyl)-1H-pyrazol-4-yl]imidazole-2-carbonyl]amino]benzoyl]piperazine-1-carboxylate (600 mg, 1.03 mmol), 2-bromo-5-methoxy-pyri dine (581.54 mg, 3.09 mmol), CuI (196.35 mg, 1.03 mmol) and (1R,2R)—N1,N2-dimethylcyclohexane-1,2-diamine (219.97 mg, 1.55 mmol) in DMF (10 mL) was heated at 100° C. for 16 h. The mixture was concentrated and the residue was purified by flash column to afford the tert-butyl 4-[2-chloro-4-[[5-[1-(5-methoxy-2-pyridyl)-3-(trifluoromethyl)pyrazol-4-yl]-1-methyl-imidazole-2 carbonyl]amino]benzoyl]piperazine-1-carboxylate (500 mg). MS $[M+H]^+$: 689.4.

The following intermediates were prepared in analogy of intermediate D10.

| Ex# | Name | MS ESI [M + H]+ | Starting Material |
|---|---|---|---|
| Intermediate D11 | tert-butyl 4-[4-[2-chloro-4-[[5-[1-[5-(2-methoxyethylamino)-2-pyridyl]-3-(trifluoromethyl)pyrazol-4-yl]-1-methyl-imidazole-2-carbonyl]amino]benzoyl]piperazine-1-carbonyl]piperidine-1-carboxylate | 843.6 | Intermediate C3 and A3 |
| Intermediate D12 | tert-butyl 4-[4-[2-chloro-4-[[1-methyl-5-[1-(5-methyl-2-pyridyl)-3-(trifluoromethyl)pyrazol-4-yl]imidazole-2-carbonyl]amino]benzoyl]piperazine-1-carbonyl]piperidine-1-carboxylate | 784.3 | Intermediate C3 and 2-iodo-5-methyl-pyridine |
| Intermediate D13 | tert-butyl 4-[4-[4-[[5-[1-[5-[(3-amino-3-oxo-propyl)amino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylate | 856.2 | Intermediate C3 and A12 |

Intermediate D30 tert-butyl 4-[4-[4-[[5-[1-(5-amino-3-fluoro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate (300.0 mg, 0.430 mmol, 1 eq), 2-(2,6-dimethylanilino)-2-oxo-acetic acid (41.81 mg, 0.220 mmol, 0.500 eq), 6-bromo-5-fluoro-pyridin-3-amine (90.94 mg, 0.480 mmol, 1.1 eq), phosphoric acid, potassium salt (0.11 mL, 1.3 mmol, 3 eq) in DMSO (S mL) was added copper(I) iodide (0.01 mL, 0.430 mmol, 1 eq) under N2. The mixture was degassed and then stirred at 120° C. for 16 h under N2. The mixture was poured into water (30 mL) and then filtered, the cake was washed with EtOAc (4×30 mL). The organic layer was separated and then washed with brine (3×30 mL), dried over sodium sulfate, the filtrate was concentrated under vacuum. The residue was purified by prep-HPLC (FA condition) to give tert-butyl 4-[4-[4-[[5-[1-(5-amino-3-fluoro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (90 mg, 0.110 mmol, 25.89% yield) as a light yellow solid. MS $[M+H]^+$: 803.3.

The following intermediates were prepared in analogy of intermediate D30.

| Ex# | Name | MS ESI $[M + H]^+$ | Starting Material |
|---|---|---|---|
| Intermediate D32 | tert-butyl 4-[4-[4-[[5-[1-(5-amino-6-fluoro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate | 803.2 | Intermediate C3 and 6-bromo-2-fluoro-pyridin-3-amine |

Intermediate D40 tert-butyl (1R,5S,6s)-6-(2-chloro-4-(1-methyl-5-(1-(pyrimidin-2-yl)-3-(trifluoromethyl)-1H-pyrazol-4-yl)-1H-imidazole-2-carboxamido)benzamido)-3-azabicyclo[3.1.0]hexane-3-carboxylate Step 1: 2-chloro-4-(1-methyl-5-(1-(pyrimidin-2-yl)-3-(trifluoromethyl)-1H-pyrazol-4-yl)-1H-imidazole-2-carboxamido)benzoic acid In a 50 mL round-bottomed flask, tert-butyl 2-chloro-4-(1-methyl-5-(1-(pyrimidin-2-yl)-3-(trifluoromethyl)-1H-pyrazol-4-yl)-1H-imidazole-2-carboxamido)benzoate (583 mg, 1.06 mmol, Eq: 1) and TFA (6.07 g, 4.1 ml, 53.2 mmol, Eq: 50) were combined with DCM (2 ml) to give a light brown solution. TFA (6.07 g, 4.1 ml, 53.2 mmol, Eq: 50) was added. The reaction was stirred at room temperature for 1 h. The crude reaction mixture was concentrated in vacuo to afford the crude title compound (523 mg, 1.06 mmol, 99.9% yield) as, which was directly used in the next step. MS $[M]^+$: 491.9

Step 2: tert-butyl (1R,5S,6s)-6-(2-chloro-4-(1-methyl-5-(1-(pyrimidin-2-yl)-3-(trifluoromethyl)-1H-pyrazol-4-yl)-1H-imidazole-2-carboxamido)benzamido)-3-azabicyclo[3.1.0]hexane-3-carboxylate In a 50 mL round-bottomed flask, 2-chloro-4-(1-methyl-5-(1-(pyrimidin-2-yl)-3-(trifluoromethyl)-1H-pyrazol-4-yl)-1H-imidazole-2-carboxamido)benzoic acid (340 mg, 691 μmol, Eq: 1), tert-butyl (1R,5S,6s)-6-amino-3-azabicyclo[3.1.0]hexane-3-carboxylate (206 mg, 1.04 mmol, Eq: 1.5), 2-(3H-[1,2,3]triazolo[4,5-b]pyridin-3-yl)-1,1,3,3-tetramethylisouronium hexafluorophosphate(V) (394 mg, 1.04 mmol, Eq: 1.5) and DIPEA (179 mg, 241 μl, 1.38 mmol, Eq: 2) were combined with DMF (5 ml) to give a light brown solution. The reaction was stirred at room temperature for 1 h. The reaction mixture was poured into 25 mL H2O, and extracted with EtOAc (3×25 mL). The organic layers were combined, washed with sat NaCl (1×25 mL), The organic layers were dried over $Na_2SO_4$ and concentrated in vacuo. to afford the title compound (240 mg, 51.7% yield). MS $[M+H]^+$: 672.2.

Intermediate E1

N-(3-Chloro-4-(piperazine-1-carbonyl)phenyl)-1-methyl-5-(1-(5-nitropyridin-2-yl)-3-(trifluoromethyl)-pyrazol-4-yl)-imidazole-2-carboxamide In a 100 mL round-bottomed flask, tert-butyl 4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carboxylate (1.4 g, 1.99 mmol) was combined with THE (8 mL) to give a light brown solution. HCl water solution (6.63 mL, 79.5 mmol) was added. The reaction was stirred at room temperature for 1 h. The crude reaction mixture was concentrated in vacuum. The crude product was directly used to the next step, to afford N-(3-chloro-4-(piperazine-1-carbonyl)phenyl)-1-methyl-5-(1-(5-nitropyridin-2-yl)-3-(trifluoromethyl)-pyrazol-4-yl)-imidazole-2-carboxamide (1.2 g). MS $[M+H]^+$: 604.2.

The following intermediates were prepared in analogy of intermediate E1.

| Ex# | Name | MS ESI $[M + H]^+$ | Starting Material |
|---|---|---|---|
| Intermediate E2 | 2-chloro-4-[[1-methyl-5-[1-pyrimidin-2-yl-3-(trifluoromethyl)pyrazol-4-yl]imidazole-2-carbonyl]amino]benzoic acid | 419.9 | Intermediate D2 and HCl |
| Intermediate E3 | N-(3-chloro-4-(piperazine-1-carbonyl)phenyl)-1-methyl-5-(1-(pyrimidin-2-yl)-3-(trifluoromethyl)-pyrazol-4-yl)-imidazole-2-carboxamide | 560.7 | Intermediate D3 and HCl |
| Intermediate E4 | N-[3-chloro-4-[4-(piperidine-4-carbonyl)piperazine-1-carbonyl]phenyl]-1-methyl-5-[1-(5-nitro-2-pyridyl)-3-(trifluoromethyl)pyrazol-4-yl]imidazole-2-carboxamide | 715.1 | Intermediate D4 and HCl |
| Intermediate E5 | N-[3-chloro-4-[4-(piperidine-4-carbonyl)piperazine-1-carbonyl]phenyl]-1-methyl-5-[1-pyrimidin-2-yl-3-(trifluoromethyl)pyrazol-4-yl]imidazole-2-carboxamide | 641.4 | Intermediate D8 and HCl |
| Intermediate E6 | N-[3-chloro-4-[4-(piperidine-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide | 700.2 | Intermediate D9 and HCl |
| Intermediate E7 | 6-[4-[2-[[3-chloro-4-[4-(piperidine-4-carbonyl)piperazine-1-carbonyl]phenyl]carbamoyl]-3-methyl-imidazol-4-yl]-3-(trifluoromethyl)pyrazol-1-yl]pyridine-3-carboxamide | 713.4 | Intermediate D5 and HCl |
| Intermediate E8 | 6-[4-[2-[[3-chloro-4-[4-(piperidine-4-carbonyl)piperazine-1-carbonyl]phenyl]carbamoyl]-3-methyl-imidazol-4-yl]-3-(trifluoromethyl)pyrazol-1-yl]-N-methyl-pyridine-3-carboxamide | 727.3 | Intermediate D6 and HCl |
| Intermediate E9 | N-[3-chloro-4-(piperazine-1-carbonyl)phenyl]-5-[1-(5-methoxy-2-pyridyl)-3-(trifluoromethyl)pyrazol-4-yl]-1-methyl-imidazole-2-carboxamide | 589.2 | Intermediate D10 and HCl |
| Intermediate E10 | N-[3-chloro-4-[4-(piperidine-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide | 684.3 | Intermediate D12 and HCl |
| Intermediate E11 | N-[3-chloro-4-[4-(4-hydroxypiperidine-4-carbonyl)piperazine-1-carbonyl]phenyl]-1-methyl-5-[1-(5-nitro-2-pyridyl)-3-(trifluoromethyl)pyrazol-4-yl]imidazole-2-carboxamide | 731.2 | Intermediate D16 and HCl |
| Intermediate E12 | 1-methyl-N-[3-methyl-4-[4-(piperidine-4-carbonyl)piperazine-1-carbonyl]phenyl]-5-[1-(5-nitro-2-pyridyl)-3-(trifluoromethyl)pyrazol-4-yl]imidazole-2-carboxamide | 695.3 | Intermediate C14 and HCl |
| Intermediate E13 | N-[3-chloro-4-[[1-(piperidine-4-carbonyl)-4-piperidyl]methylcarbamoyl]phenyl]-1-methyl-5-[1-(5-nitro-2-pyridyl)-3-(trifluoromethyl)pyrazol-4-yl]imidazole-2-carboxamide | 743.2 | Intermediate D25 and HCl |
| Intermediate E14 | N-[3-chloro-4-[4-[(3S)-morpholine-3-carbonyl]piperazine-1-carbonyl]phenyl]-1-methyl-5-[1-(5-nitro-2-pyridyl)-3-(trifluoromethyl)pyrazol-4-yl]imidazole-2-carboxamide | 717.3 | Intermediate D26 and HCl |
| Intermediate E15 | 5-[1-(5-amino-3-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 703.1 | Intermediate D30 and HCl |
| Intermediate E16 | 5-[1-(5-amino-4-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide | 699.2 | Intermediate G7 and TFA in DCM |
| Intermediate E17 | 5-[1-(5-amino-6-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 703.3 | Intermediate D32 and HCl |
| Intermediate E18 | 5-[1-(5-amino-6-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 699.4 | Intermediate G8 and TFA in DCM |

-continued

| Ex# | Name | MS ESI [M + H]$^+$ | Starting Material |
| --- | --- | --- | --- |
| Intermediate E19 | 5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 719.2 | Intermediate D34 and TFA in DCM |
| Intermediate E20 | 5-[1-(5-amino-2-pyridyl)-3-(trifluoromethyl)pyrazol-4-yl]-N-[3-chloro-4-(piperazine-1-carbonyl)phenyl]-1-methyl-imidazole-2-carboxamide; hydrogen chloride | 572.3, [M − H]$^-$ | Intermediate G9 and HCl in dioxane, DCM |
| Intermediate E21 | N-[3-chloro-4-(4-isonipecotoylpiperazine-1-carbonyl)phenyl]-1-methyl-5-[1-(5-nitropyrazin-2-yl)-3-(trifluoromethyl)pyrazol-4-yl]imidazole-2-carboxamide; hydrogen chloride | 716.2 | Intermediate D36 and HCl in dioxane, DCM |
| Intermediate E22 | N-[3-chloro-4-[[(exo)-3-[(2S,4R)-4-hydroxyprolyl]-3-azabicyclo[3.1.0]hexan-6-yl]carbamoyl]phenyl]-1-methyl-5-[1-(5-nitro-2-pyridyl)-3-(trifluoromethyl)pyrazol-4-yl]imidazole-2-carboxamide; hydrogen chloride | 729.2 | Intermediate D37 and HCl in dioxane, DCM |
| Intermediate E23 | N-[4-[[(exo)-3-azabicyclo[3.1.0]hexan-6-yl]carbamoyl]-3-chloro-phenyl]-1-methyl-5-[1-(5-nitro-2-pyridyl)-3-(trifluoromethyl)pyrazol-4-yl]imidazole-2-carboxamide; hydrogen chloride | 616.1 | Intermediate D38 and HCl in dioxane, DCM |
| Intermediate E24 | N-(4-(((1R,5S,6s)-3-azabicyclo[3.1.0]hexan-6-yl)carbamoyl)-3-chlorophenyl)-1-methyl-5-(1-(pyrimidin-2-yl)-3-(trifluoromethyl)-1H-pyrazol-4-yl)-1H-imidazole-2-carboxamide; hydrogen chloride | 572.7 | Intermediate D40 and HCl |

Intermediate F1

N-[3-Chloro-4-[4-[2-(3-hydroxypyrrolidin-1-yl)acetyl]piperazine-1-carbonyl]phenyl]-1-methyl-5-[1-(5-nitro-2-pyridyl)-3-(trifluoromethyl)pyrazol-4-yl]imidazole-2-carboxamide

Step 1: N-[3-chloro-4-[4-(2-chloroacetyl)piperazine-1-carbonyl]phenyl]-1-methyl-5-[1-(5-nitro-2-pyridyl)-3-(trifluoromethyl)pyrazol-4-yl]imidazole-2-carboxamide To a solution of N-[3-chloro-4-(piperazine-1-carbonyl)phenyl]-1-methyl-5-[1-(5-nitro-2-pyridyl)-3-(trifluoromethyl)pyrazol-4-yl]imidazole-2-carboxamide 0.1:1 2,2,2-trifluoroacetic acid (300 mg, 0.42 mmol) in acetonitrile (5 mL) was added sodium carbonate (132.9 mg, 1.3 mmol), then chloroacetyl chloride (47.2 mg, 0.42 mmol) was added dropwise at 0° C. The reaction was stirred for 2 h and then warmed to room temperature. The reaction mixture was washed with brine and extracted in DCM. The organic layer was dried over anhydrous $Na_2SO_4$ and concentrated in vacuum. The residue was directly used for the next step without further purification. MS [M+H]$^+$: 680.2.

Step 2: N-[3-chloro-4-[4-[2-(3-hydroxypyrrolidin-1-yl)acetyl]piperazine-1-carbonyl]phenyl]-1-methyl-5-[1-(5-nitro-2-pyridyl)-3-(trifluoromethyl)pyrazol-4-yl]imidazole-2-carboxamide To a solution of N-[3-chloro-4-[4-(2-chloroacetyl)piperazine-1-carbonyl]phenyl]-1-methyl-5-[1-(5-nitro-2-pyridyl)-3-(trifluoromethyl)pyrazol-4-yl]imidazole-2-carboxamide (230 mg, 0.34 mmol) in acetonitrile (3 mL) was added 3-pyrrolidinol (29.5 mg, 0.34 mmol) and TEA (68.4 mg, 0.68 mmol), the reaction was stirred for 30 min at 70 TC. The reaction mixture was cooled to room temperature. The reaction mixture was washed with brine and extracted in DCM. The organic layer was dried over anhydrous $Na_2SO_4$ and concentrated in vacuum. The residue was directly used for the next step without further purification. MS [M+H]$^+$: 731.2.

The following intermediates were prepared in analogy of intermediate F1.

| Ex# | Name | MS ESI [M + H]$^+$ | Starting Material |
| --- | --- | --- | --- |
| Intermediate F2 | N-[3-chloro-4-[4-[2-[(3R)-3-hydroxypyrrolidin-1-yl]acetyl]piperazine-1-carbonyl]phenyl]-1-methyl-5-[1-pyrimidin-2-yl-3-(trifluoromethyl)pyrazol-4-yl]imidazole-2-carboxamide | 687.2 | Intermediate E3 and (R)-3-hydroxypyrrolidine |
| Intermediate F3 | N-[3-chloro-4-[4-[2-[(3R)-3-hydroxypyrrolidin-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide | 716.3 | Intermediate E9 and (R)-3-hydroxypyrrolidine |

Intermediate G1 tert-Butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate In a 100 mL round-bottomed flask, tert-butyl 4-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)piperidine-1-carboxylate (47 mg, 57.7 mol) was combined with EtOH (6 mL)/Water (6 mL) to give a light yellow. Zinc (75.4 mg, 1.15 mmol) and $NH_4Cl$ (61.7 mg, 1.15 mmol) were added at rt. The reaction was stirred at room temperature for 1 h. The reaction mixture was filtered through glass fiber paper. The filtrate was poured into 20 mL $H_2O$ and extracted with EtOAc (25 mL×3). The organic layers were combined, washed with sat NaCl (25 mL×1). The organic layers were dried over $Na_2SO_4$ and concentrated in vacuum to afford tert-butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate (45.3 mg). MS $[M+H]^+$: 785.0.

The following intermediates were prepared in analogy of intermediate G1.

| Ex# | Name | MS ESI $[M + H]^+$ | Starting Material |
|---|---|---|---|
| Intermediate G2 | tert-butyl 4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-4-hydroxy-piperidine-1-carboxylate | 801.2 | Intermediate D16 and Zinc |
| Intermediate G3 | 5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide | 701.2 | Intermediate F1 and Zinc |
| Intermediate G4 | tert-butyl (2S,3S)-2-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-3-hydroxy-pyrrolidine-1-carboxylate | 787.3 | Intermediate D27 and Zinc |
| Intermediate G5 | tert-butyl 4-[4-[4-[[5-[1-(5-amino-2-pyridyl)-3-(trifluoromethyl)pyrazol-4-yl]-1-methyl-imidazole-2-carbonyl]amino]-2-methyl-benzoyl]piperazine-1-carbonyl]piperidine-1-carboxylate | 765.3 | Intermediate D24 and Zinc |
| Intermediate G6 | tert-butyl (3S,4R)-4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-3-hydroxy-piperidine-1-carboxylate | 801.2 | Intermediate D28 and Zinc |

Intermediate G7 tert-butyl 4-[4-[4-[[5-[1-(5-amino-4-methyl-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[1-(4-methyl-5-nitro-2-pyridyl)-3-(trifluoromethyl)pyrazol-4-yl]imidazole-2-carbonyl]amino]benzoyl]piperazine-1-carbonyl]piperidine-1-carboxylate (60.0 mg, 0.070 mmol, 1 eq) and saturated $NH_4Cl$ in water (1.0 mL) in Methanol (2 mL) and was added iron powder (80.82 mg, 1.45 mmol, 20 eq). The mixture was stirred at 30° C. for 16 h. The mixture was diluted with water (20 mL) and EtOAc (20 mL), filtered. The filtrate was extracted with EtOAc (2×30 mL). The combined organic layers were washed with brine (30 mL), dried over sodium sulfate, filtered, the filtrate was concentrated under vacuum to give tert-butyl 4-[4-[4-[[5-[1-(5-amino-4-methyl-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (60 mg, 0.080 mmol, 98.56% yield) as a light brown solid. MS $[M+H-Boc]^+$: 699.3.

The following intermediates were prepared in analogy of intermediate G7.

| Ex# | Name | MS ESI $[M + H]^+$ | Starting Material |
|---|---|---|---|
| Intermediate G8 | tert-butyl 4-[4-[4-[[5-[1-(5-amino-6-methyl-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate | 799.3 | Intermediate D33 and iron powder |
| Intermediate G9 | 4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carboxylic acid tert-butyl ester | 672.4, $[M - H]^-$ | Intermediate D1 and iron powder |

Intermediate H1 tert-Butyl 4-[4-[2-chloro-4-[[5-[1-[5-(ethylamino)-2-pyridyl]-3-(trifluoromethyl)pyrazol-4-yl]-1-methyl-imidazole-2-carbonyl]amino]benzoyl]piperazine-1-carbonyl]piperidine-1-carboxylate At 0° C., to a solution of tert-butyl 4-[4-[4-[[5-[1-(5-amino-2-pyridyl)-3-(trifluoromethyl)pyrazol-4-yl]-1-methyl-imidazole-2-carbonyl]amino]-2-chloro-benzoyl] piperazine-1-carbonyl]piperidine-1-carboxylate (460 mg, 0.586 mmol) in methanol (30 mL) was added 5 M acetaldehyde (228.47 mg, 292.91 uL, 1.46 mmol) in THE and acetic acid (211.07 mg, 201.21 uL, 3.51 mmol). Then the solution was stirred for 30 min at 0° C. Then $NaBH_3CN$ (184.07 mg, 2.93 mmol) was added and was stirred at 0° C. for 2 h. Excess of water was added gradually, and the solution was neutralized (pH=~8) by addition of aqueous 3N sodium hydroxide. The mixture was stirred for 1 h. The water layer was extracted with DCM. The combined organic layers were concentrated and the residue was purified by flash column to afford tert-butyl 4-[4-[2-chloro-4-[[5-[1-[5-(ethylamino)-2-pyridyl]-3-(trifluoromethyl)pyrazol-4-yl]-1-methyl-imidazole-2-carbonyl]amino]benzoyl]piperazine-1-carbonyl]piperidine-1-carboxylate (410 mg) as a yellow solid. MS $[M+H]^+$: 813.6.

Intermediate I1

(2S,4R)-1-tert-butoxycarbonyl-4-hydroxy-pyrrolidine-2-carboxylic acid

To a solution of L-hydroxyproline (2.49 g, 19 mmol, 1 eq) in THE (26 mL)/water (13 mL) was added sodium hydroxide (13.67 mL, 38 mmol, 2 eq) followed the addition of di-t-butyldicarbonate (6.22 g, 28.5 mmol, 1.5 eq) at 15° C. and stirred at 30° C. for 16 h. The reaction mixture was extracted with EtOAc while pH was about 9~10. The water layer was adjusted pH to 1~2 with 2.0 N HCl aqueous and then lyophilized. 100 mL $CH_3CN$ and 50 mL EtOAc was added and stirred at room temperature. After 2 hr, the mixture was filtered and concentrated to give the title compound (3.8 g, 86.49% yield) as white solid.

Example A1

N-[3-Chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide; formate

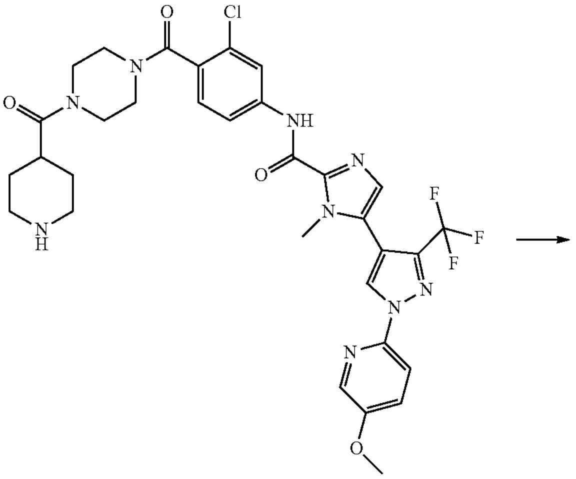

Intermediate E6

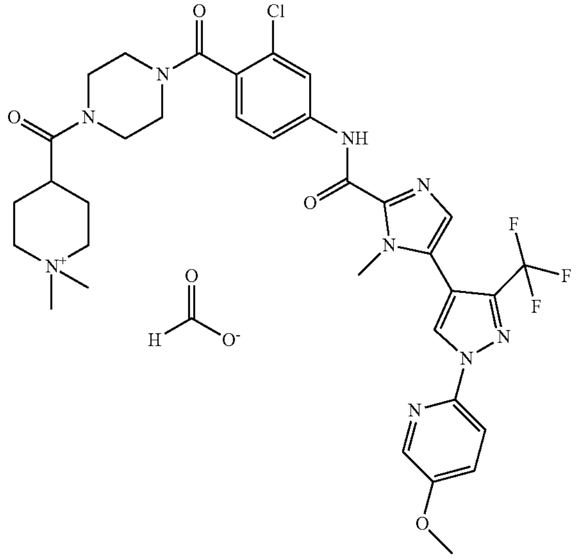

Example A1

In a 50 mL round-bottomed flask, N-(3-chloro-4-(4-(piperidine-4-carbonyl)piperazine-1-carbonyl)phenyl)-5-(1-(5-methoxypyridin-2-yl)-3-(trifluoromethyl)-pyrazol-4-yl)-1-methyl-imidazole-2-carboxamide (78 mg, 111 μmol), MeI (79.1 mg, 34.8 μl, 557 μmol) and DIPEA (72 mg, 97.3 μl, 557 μmol) were combined with MeCN (5 mL) to give a light brown solution. The reaction was stirred at room temperature for 1 h. The crude reaction mixture was concentrated in vacuum. The crude material was purified by preparative HPLC. to afford N-[3-chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide;formate (22.3 mg). MS $[M+H]^+$:728.2.

The following compounds were prepared in analogy of Example A1.

| Ex# | Name | Structure | MS ESI $[M]^+$ | Starting Material |
| --- | --- | --- | --- | --- |
| Example A2 | 6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]pyridine-3-carboxamide;formate | 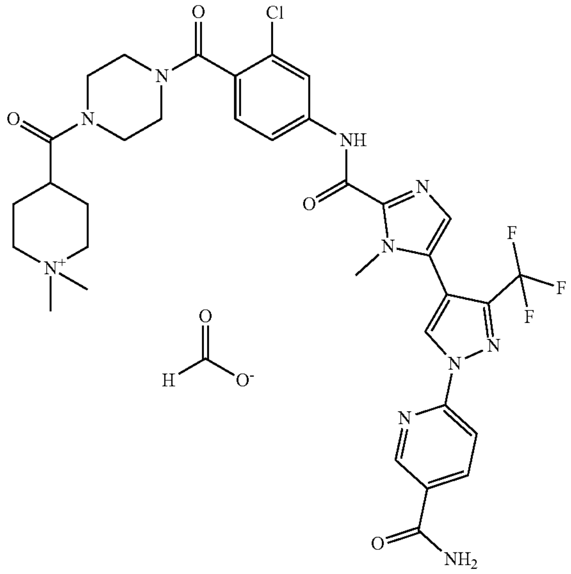 | 741.3 | Inter-medi-ate E7 and iodo-methane |
| Example A3 | 6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]-N-methyl-pyridine-3-carboxamide;formate | 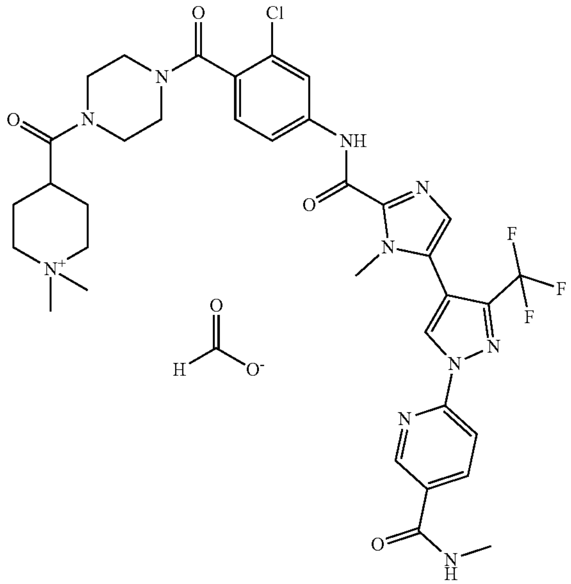 | 755.3 | Inter-mediate E8 and iodo-methane |

-continued

| Ex# | Name | Structure | MS ESI [M]+ | Starting Material |
| --- | --- | --- | --- | --- |
| Example A4 | N-[3-chloro-4-[4-(1, 1-dimethylpiperidin-1-ium-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide;formate | 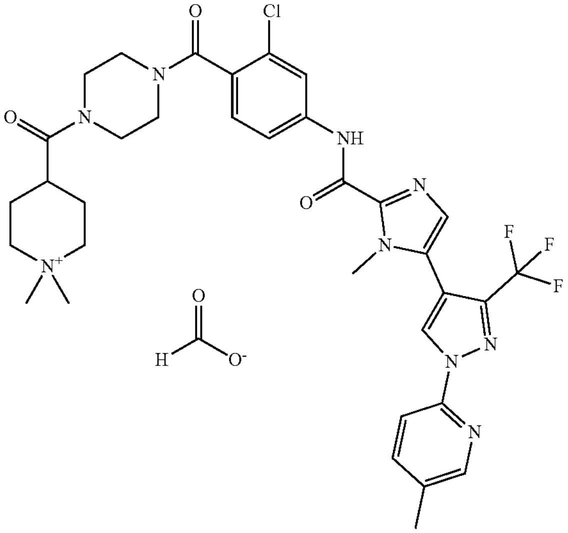 | 712.5 | Intermediate E10 and iodomethane |
| Example A5 | 5-[1-(5-amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;2,2,2-trifluoroacetate | 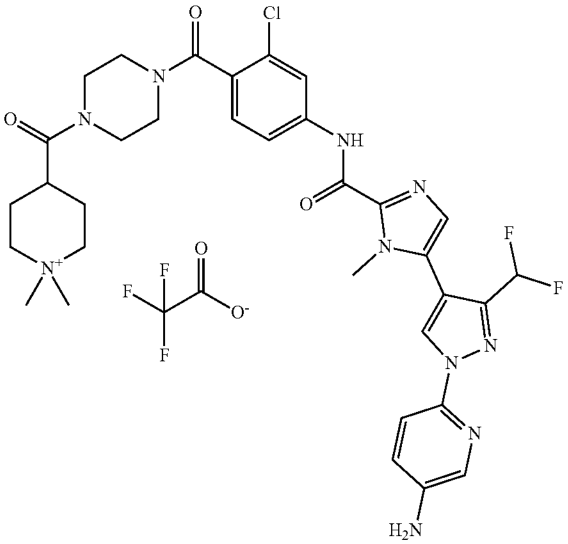 | 695.3 | Intermediate D17 and iodomethane |
| Example A6 | N-[3-chloro-4-[4-[2-[(3R)-3-hydroxy-1-methyl-pyrrolidin-1-ium-1-yl]acetyl]piperazine-1-carbonyl]phenyl]-1-methyl-5-[1-pyrimidin-2-yl-3-(trifluoromethyl)pyrazol-4-yl]imidazole-2-carboxamide;formate | 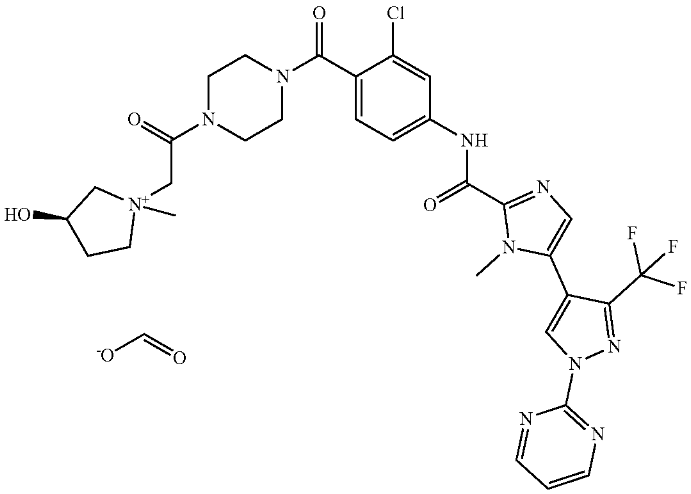 | 701.2 | Intermediate F2 and iodomethane |

-continued

| Ex# | Name | Structure | MS ESI [M]+ | Starting Material |
|---|---|---|---|---|
| Example A7 | N-[3-chloro-4-[4-[2-[(3R)-3-hydroxy-1-methyl-pyrrolidin-1-ium-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide;formate | 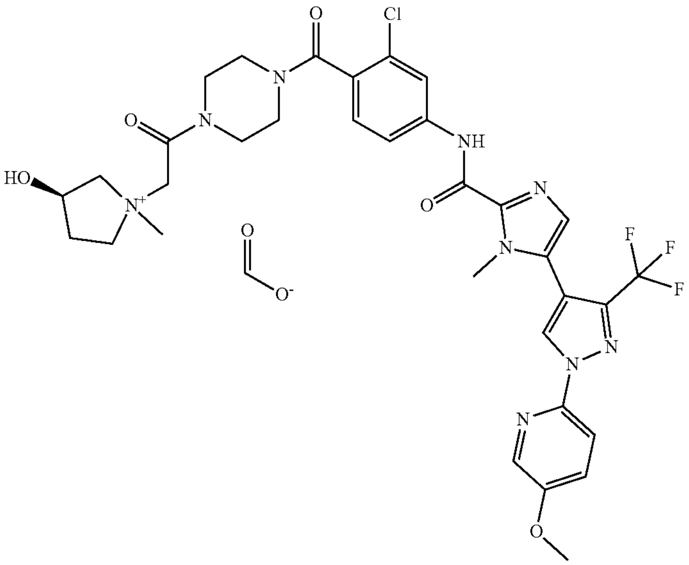 | 730.5 | Intermediate F3 and iodomethane |
| Example A8 | 5-[l-(5-amino-3-fluoro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate | 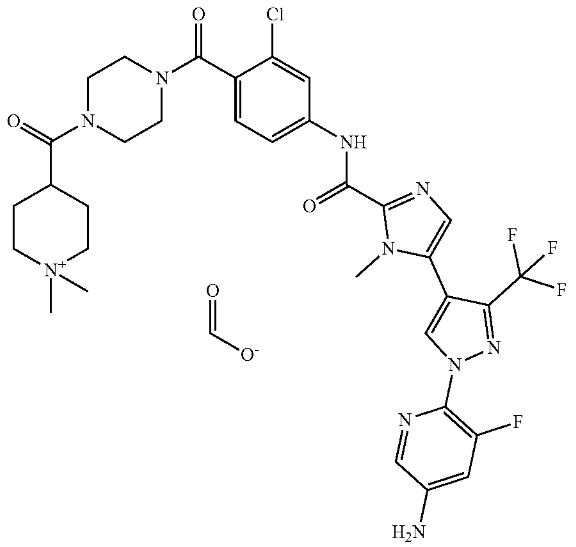 | 366.3, [M + H]2+/2 | Intermediate E15 and iodomethane |

-continued

| Ex# | Name | Structure | MS ESI $[M]^+$ | Starting Material |
|---|---|---|---|---|
| Example A9 | 5-[l-(5-amino-4-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate | 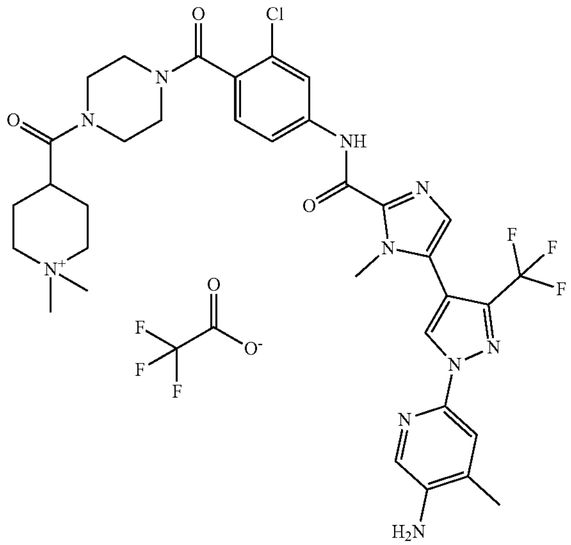 | 364.3, $[M + H]^{2+}/2$ | Inter-mediate E16 and iodo-methane |
| Example A10 | 5-[l-(5-amino-6-fluoro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate | 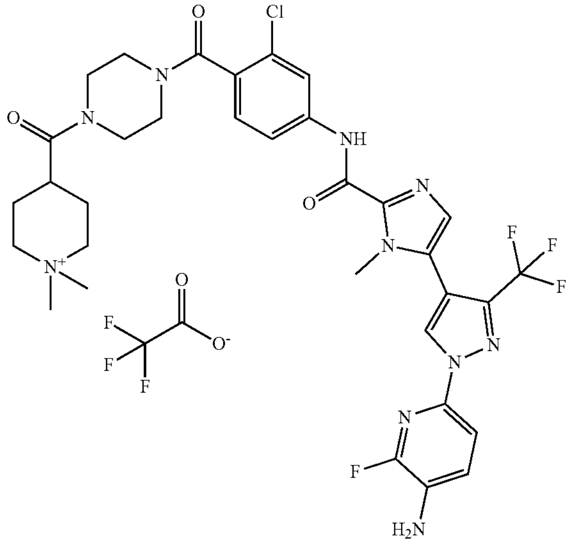 | 366.2, $[M + H]^{2+}/2$ | Inter-mediate E17 and iodo-methane |

-continued

| Ex# | Name | Structure | MS ESI $[M]^+$ | Starting Material |
|---|---|---|---|---|
| Example A11 | 5-[l-(5-amino-6-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate | 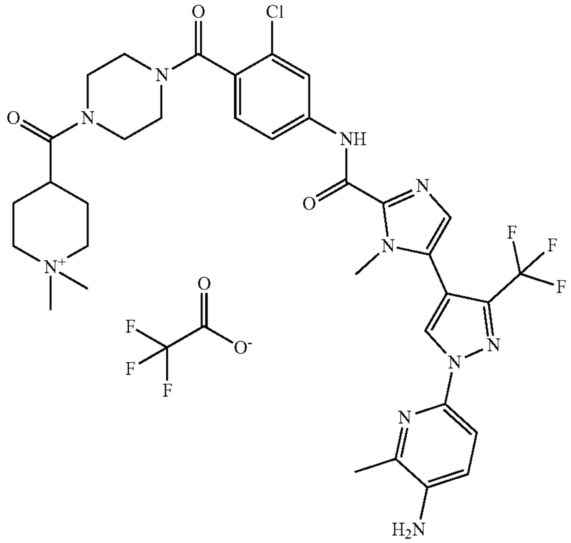 | 364.3, $[M + H]^{2+}/2$ | Inter-mediate E18 and iodo-methane |
| Example A12 | 5-[1-(5-amino-4-chloro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate | 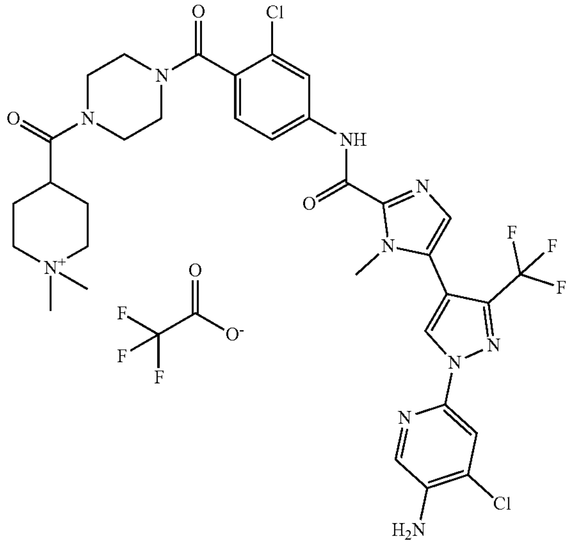 | 747.3 | Inter-mediate E19 and iodo-methane |

Example B1

N-[3-Chloro-4-[4-(1,1-dimethylpiperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide; formate

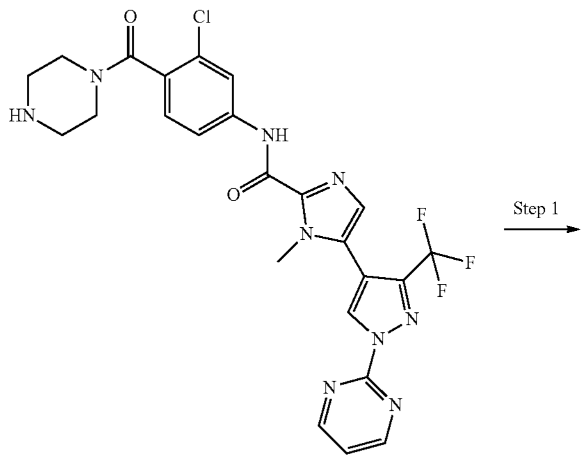

Intermediate E3

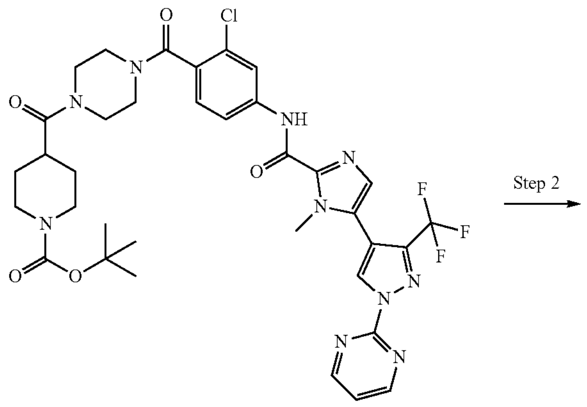

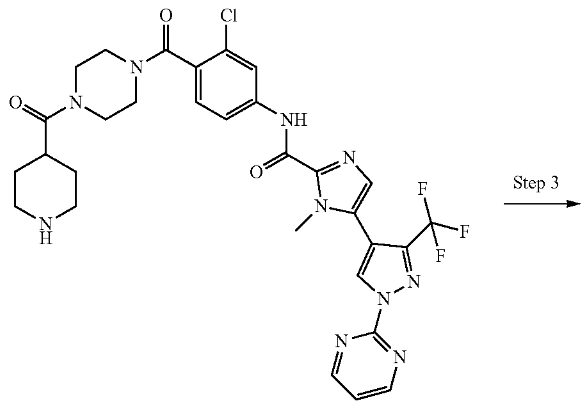

-continued

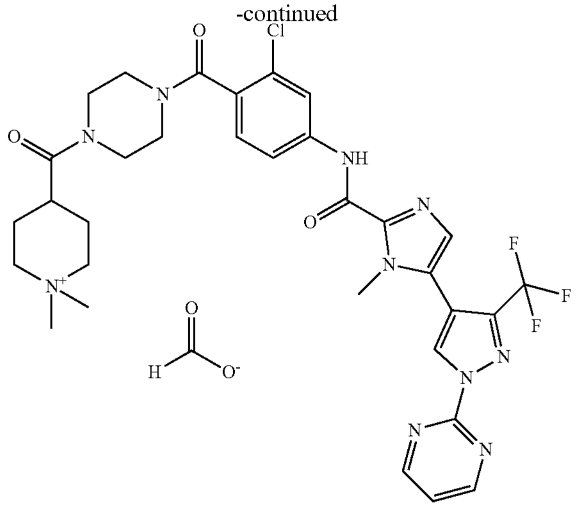

Example B1

Step 1: tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidine-1-carboxylate In a 50 mL round-bottomed flask, N-(3-chloro-4-(piperazine-1-carbonyl)phenyl)-1-methyl-5-(1-(pyrimidin-2-yl)-3-(trifluoromethyl)-pyrazol-4-yl)-imidazole-2-carboxamide (110 mg, 196 μmol), 1-(tert-butoxycarbonyl)piperidine-4-carboxylic acid (58.6 mg, 255 μmol), HATU (97.1 mg, 255 μmol) and DIPEA (50.8 mg, 393 μmol) were combined with DMF (3 mL) to give a light brown solution. The reaction mixture was poured into 50 mL $H_2O$ and extracted with EtOAc (25 mL×3). The organic layers were combined, washed with sat NaCl (25 mL×1). The organic layers were dried over $Na_2SO_4$ and concentrated in vacuum to afford tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidine-1-carboxylate (150 mg). MS $[M+H]^+$: 771.6.

Step 2: N-(3-chloro-4-(4-(piperidine-4-carbonyl)piperazine-1-carbonyl)phenyl)-1-methyl-5-(1-(pyrimidin-2-yl)-3-(trifluoromethyl)-pyrazol-4-yl)-imidazole-2-carboxamide In a 50 mL round-bottomed flask, tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidine-1-carboxylate (150 mg, 195 μmol) was combined with THE (2 mL) to give a light brown solution. HCl (1.3 mL, 15.6 mmol) was added. The reaction was stirred at room temperature for 20 min. The crude reaction mixture was concentrated in vacuum. The crude product was directly used to the next step, to afford N-(3-chloro-4-(4-(piperidine-4-carbonyl)piperazine-1-carbonyl)phenyl)-1-methyl-5-(1-(pyrimidin-2-yl)-3-(trifluoromethyl)-pyrazol-4-yl)-imidazole-2-carboxamide (131 mg). MS $[M+H]^+$: 670.7.

Step 3: N-[3-chloro-4-[4-(1,1-dimethylpiperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide; formate In a 50 mL round-bottomed flask, N-(3-chloro-4-(4-(piperidine-4-carbonyl)piperazine-1-carbonyl)phenyl)-1- methyl-5-(1-(pyrimidin-2-yl)-3-(trifluoromethyl)-pyrazol-4-yl)-imidazole-2-carboxamide (65 mg, 96.9 μmol), MeI (68.7 mg, 30.3 μl, 484 μmol) and DIPEA (62.6 mg, 484 mol) were combined with MeCN (5 mL) to give a light brown solution. The reaction was stirred at room temperature for 1 h. The crude reaction mixture was concentrated in vacuum. The crude material was purified by preparative HPLC. to afford N-[3-chloro-4-[4-(1,1-dimethylpiperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide;formate (16.1 mg). MS $[M+H]^+$: 699.9.

The following compounds were prepared in analogy of Example B1.

| Ex# | Name | Structure | MS ESI $[M]^+$ | Starting Material |
|---|---|---|---|---|
| Example B2 | N-[3-chloro-4-[4-[(2S,4R)-4-hydroxy-1,1-dimethyl-pyrrolidin-1-ium-2-carbonyl] piperazine-1-carbonyl]phenyl]-1-methyl-5-[l-pyrimidin-2-yl-3-(trifluoromethyl) pyrazol-4-yl]imidazole-2-carboxamide; formate | 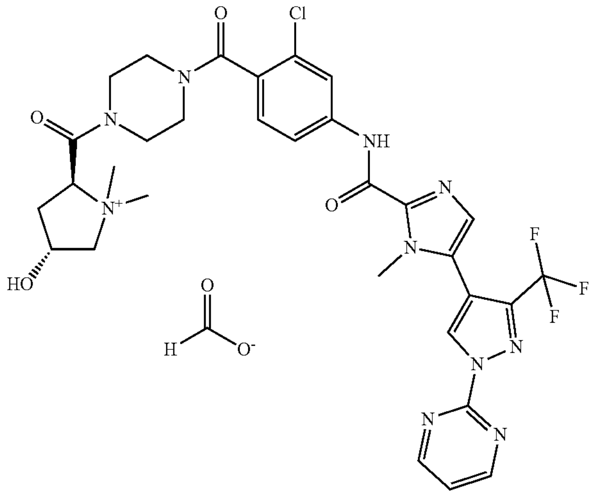 | 701.2 | Intermediate E3 and (2S,4R)-1-(tert-butoxy carbonyl)-4-hydroxypyrro lidine-2-carboxylic acid and iodomethane |
| Example B3 | N-[3-chloro-4-[4-[(2S, 3S)-3-hydroxy-1,1-dimethyl-pyrrolidin-1-ium-2-carbonyl]piperazine-1-carbonyl]phenyl]-1-methyl-5-[l-pyrimidin-2-yl-3-(trifluoromethyl)pyrazol-4-yl]imidazole-2-carboxamide; formate | 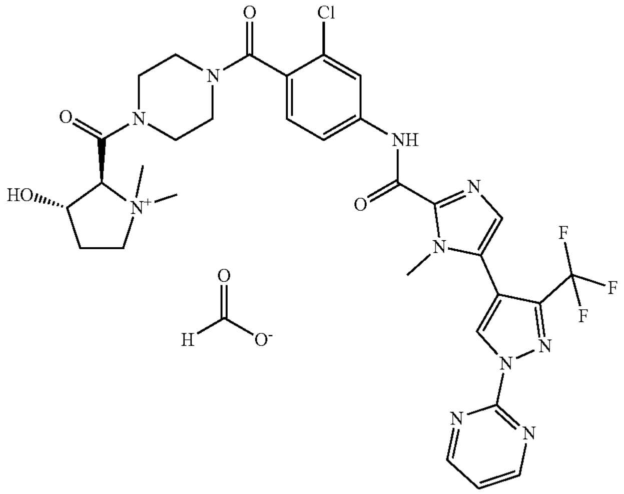 | 701.2 | Intermediate E3 and (2S,3S)-1-tert-butoxycarbon yl-3-hydroxy-pyrrolidine-2-carboxylic acid and iodomethane |

-continued

| Ex# | Name | Structure | MS ESI $[M]^+$ | Starting Material |
|---|---|---|---|---|
| Example B4 | N-[3-chloro-4-[4-(3-hydroxy-1,1-dimethyl-piperidin-1-ium-4-carbonyl)piperazine-1-carbonyl]phenyl]-1-methyl-5-[l-pyrimidin-2-yl-3-(trifluoromethyl)pyrazol-4-yl]imidazole-2-carboxamide; formate | 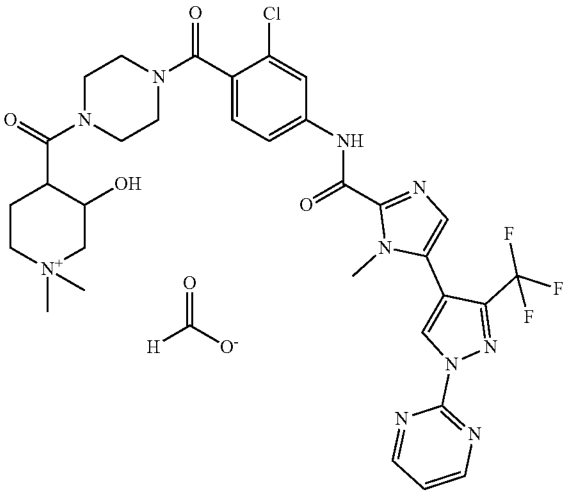 | 715.3 | Intermediate E3 and 1-tert-butoxycarbonyl-3-hydroxy-piperidine-4-carboxylic acid and iodomethane |
| Example B5 | N-[3-chloro-4-[4-[(3S,4R)-3-hydroxy-1,1-dimethyl-piperidin-1-ium-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide | 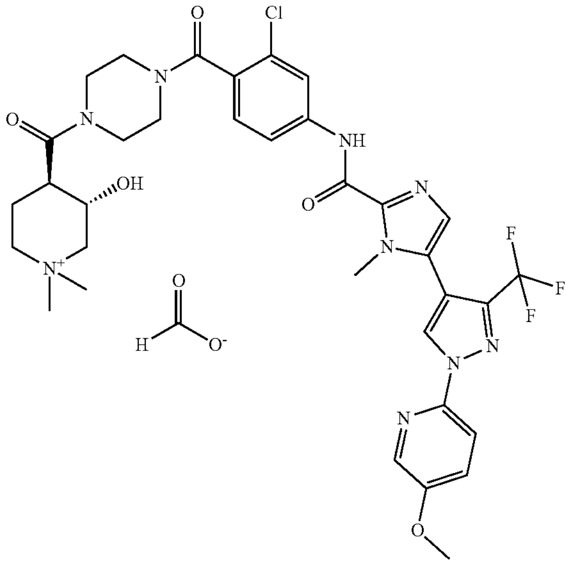 | 744.5 | Intermediate E9 and (3S,4R)-1-tert-butoxycarbonyl-3-hydroxy-piperidine-4-carboxylic acid and iodomethane |

-continued

| Ex# | Name | Structure | MS ESI [M]+ | Starting Material |
|---|---|---|---|---|
| Example B6 | N-[3-chloro-4-[4-[(2S,4R)-4-hydroxy-1,1-dimethyl-pyrrolidin-1-ium-2-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide; formate | 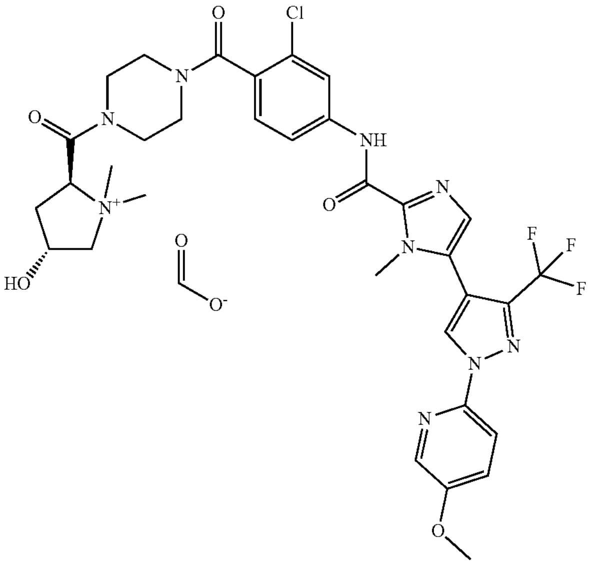 | 730.5 | Intermediate E9 and (2S,4R)-1-(tert-butoxy carbonyl)-4-hydroxypyrrolidine-2-carboxylic acid and iodomethane |
| Example B7 | N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[l-(5-nitro-2-pyridyl)-3-(trifluoromethyl)pyrazol-4-yl]imidazole-2-carboxamide; formate | 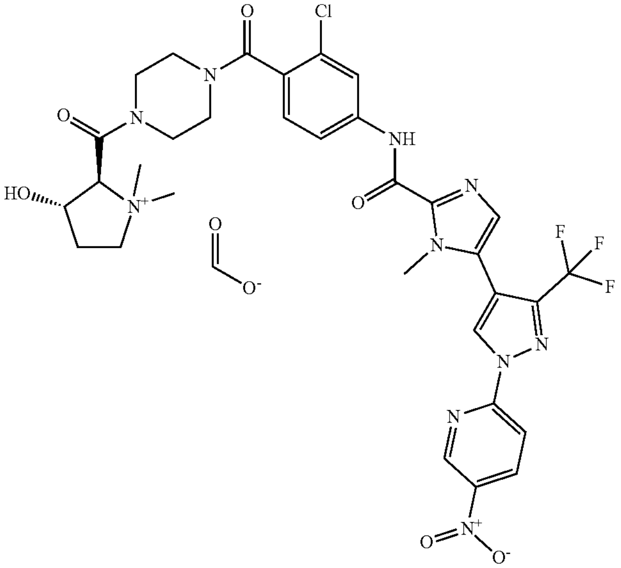 | 745.5 | Intermediate D27 and HCl and iodomethane |
| Example B8 | rac-(2R,4S)-2-((lR,5S,6S)-6-(2-chloro-4-(l-methyl-5-(l-(pyrimidin-2-yl)-3-(trifluoromethyl)-1H-pyrazol-4-yl)-1H-imidazole-2-carboxamido)benzamido)-3-azabicyclo[3.1.0]hexane-3-carbonyl)-4-hydroxy-1,1-dimethylpyrrolidin-1-ium; formate | 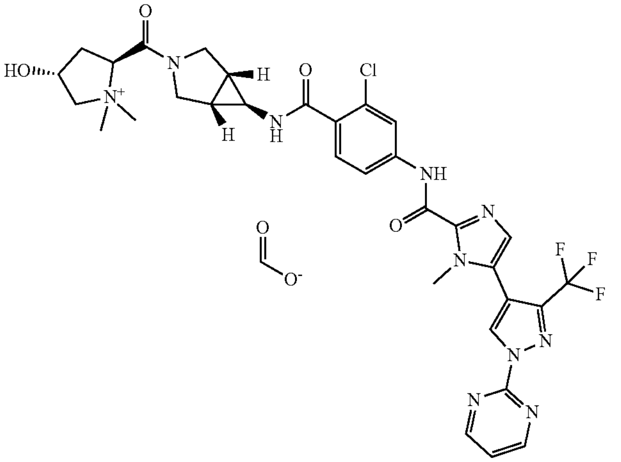 | 713.2 | Intermediate E24 and Intermediate 11 and iodomethane |

-continued

| Ex# | Name | Structure | MS ESI $[M]^+$ | Starting Material |
| --- | --- | --- | --- | --- |
| Example B9 | 4-(2-chloro-4-(1-methyl-5-(1-(pyrimidin-2-yl)-3-(trifluoromethyl)-1H-pyrazol-4-yl)-1H-imidazole-2-carboxamido)benzoyl)-1,1-dimethylpiperazin-1-ium; formate | 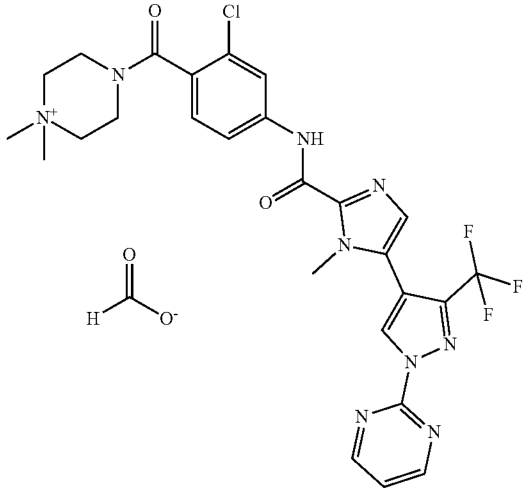 | 588.9 | Intermediate E3 and 1-(tert-butoxycarbonyl)piperidine-4-carboxylic acid and iodomethane; Example B9 was isolated together with Example B1 |

Example C1

N-[4-[4-[1-(Azetidin-3-ylmethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formate

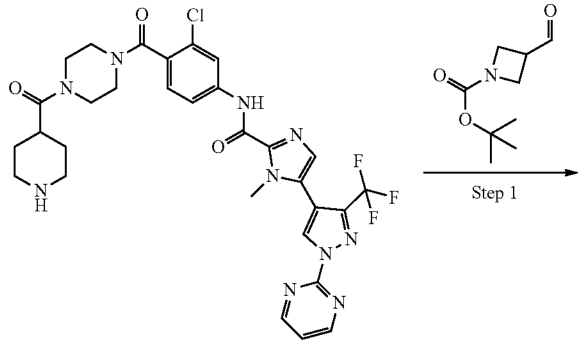

intermediate E5

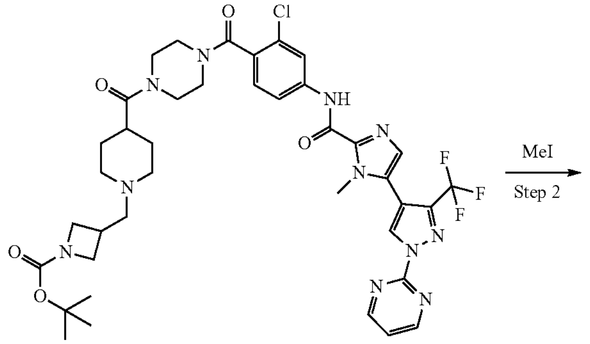

-continued

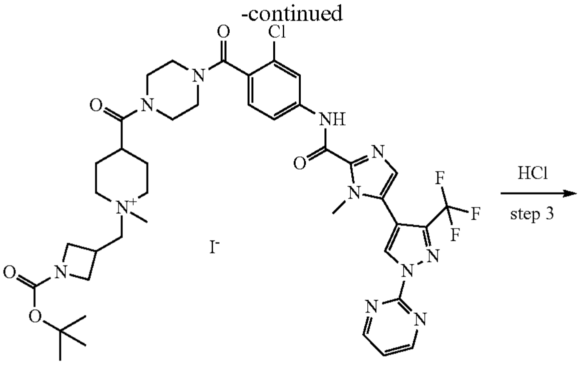

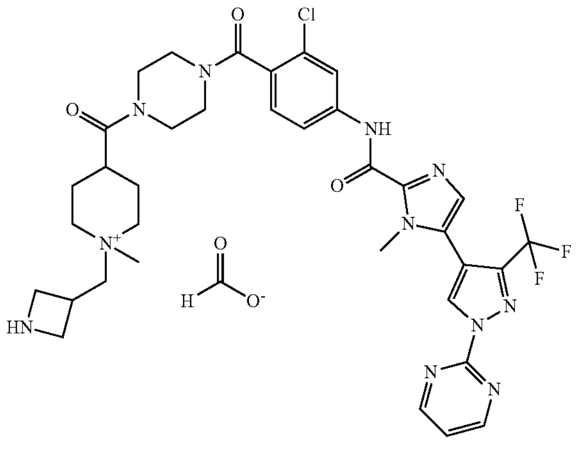

Example C1

Step 1: tert-butyl 3-((4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidin-1-yl)methyl)azetidine-1-carboxylate In a 50 mL round-bottomed flask, N-(3-chloro-4-(4-(piperidine-4-carbonyl)piperazine-1-carbonyl)phenyl)-1-methyl-5-(1-(pyrimidin-2-yl)-3-(trifluoromethyl)-pyrazol-4-yl)-imidazole-2-carboxamide (143 mg, 213 μmol), tert-butyl 3-formylazetidine-1-carboxylate (59.2 mg, 320 μmol) and $NaBH_3CN$ (26.8 mg, 426 μmol) were combined with MeOH (5 mL) to give a light brown solution. The reaction mixture was heated to 45° C. and stirred for 15 h. The crude reaction mixture was concentrated in vacuum. The reaction mixture was poured into 25 mL $H_2O$ and extracted with EtOAc (25 mL×3). The organic layers were combined, washed with sat NaCl (25 mL×1). The organic layers were dried over $Na_2SO_4$ and concentrated in vacuum. to afford tert-butyl 3-((4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidin-1-yl)methyl)azetidine-1-carboxylate (179 mg). MS $[M+H]^+$: 840.5.

Step 2: tert-butyl 3-[[4-[4-[2-chloro-4-[[1-methyl-5-[1-pyrimidin-2-yl-3-(trifluoromethyl)pyrazol-4-yl]imidazole-2-carbonyl]amino]benzoyl]piperazine-1-carbonyl]-1-methyl-piperidin-1-ium-1-yl]methyl]azetidine-1-carboxylate; iodide In a 50 mL round-bottomed flask, tert-butyl 3-((4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidin-1-yl)methyl)azetidine-1-carboxylate (80 mg, 95.2 μmol), MeI (67.6 mg, 29.8 μl, 476 μmol) and DIPEA (61.5 mg, 476 μmol) were combined with MeCN (5 mL) to give a light brown solution. The reaction was stirred at room temperature for 2 h. The crude reaction mixture was concentrated in vacuum. The crude product was directly used to the next step to afford tert-butyl 3-[[4-[4-[2-chloro-4-[[1-methyl-5-[1-pyrimidin-2-yl-3-(trifluoromethyl)pyrazol-4-yl]imidazole-2-carbonyl]amino]benzoyl]piperazine-1-carbonyl]-1-methyl-piperidin-1-ium-1-yl]methyl]azetidine-1-carboxylate;iodide (81.4 mg). MS $[M+H]^+$: 854.3.

Step 3: N-[4-[4-[1-(azetidin-3-ylmethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formate In a 50 mL round-bottomed flask, 1-((1-(tert-butoxycarbonyl)azetidin-3-yl)methyl)-4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)-1-methylpiperidin-1-ium (81 mg, 94.7 μmol) was combined with THE (3 mL) to give a light brown solution. HCl (631 μl, 7.58 mmol) was added. The reaction was stirred at room temperature for 1 h. The crude reaction mixture was concentrated in vacuum. The crude material was purified by preparative HPLC. to afford N-[4-[4-[1-(azetidin-3-ylmethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formate (16 mg). MS: 754.1.

The following compounds were prepared in analogy of Example C1.

| Ex# | Name | Structure | MS ESI $[M + H]^+$ | Starting Material |
|---|---|---|---|---|
| Example C2 | N-[4-[4-[1-(2-amino-2-oxo-ethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formate | 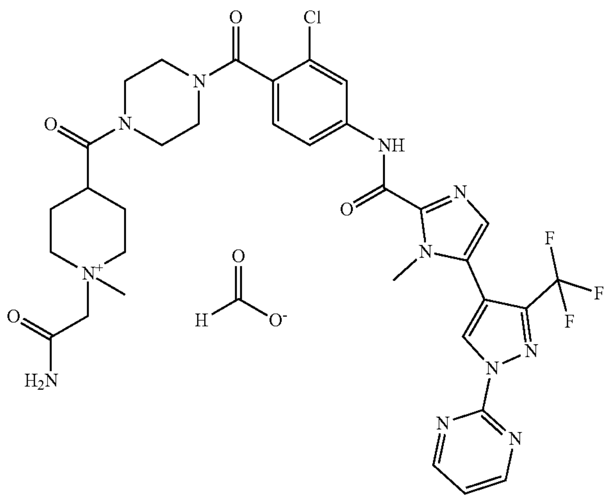 | 742.6 | Intermediate E5 and formaldehyde and 2-iodoacetamide |

Example D1

5-[1-(5-Amino-2-pyridyl)-3-(trifluoromethyl)pyrazol-4-yl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide; formate

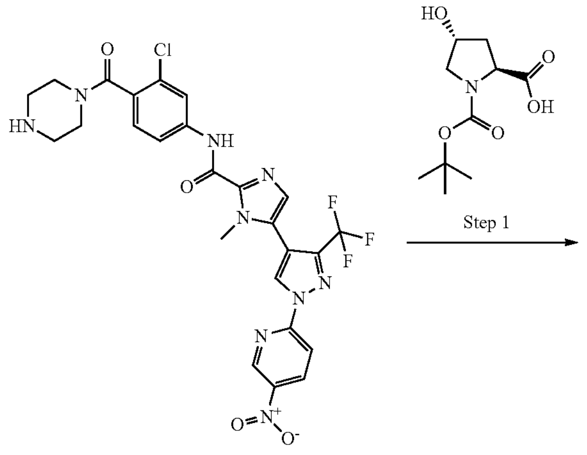

intermediate E1

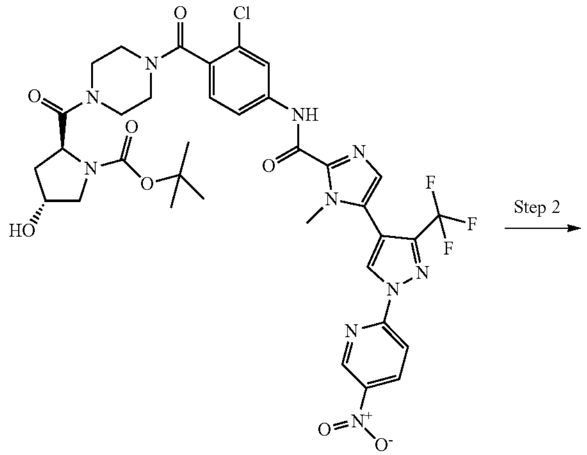

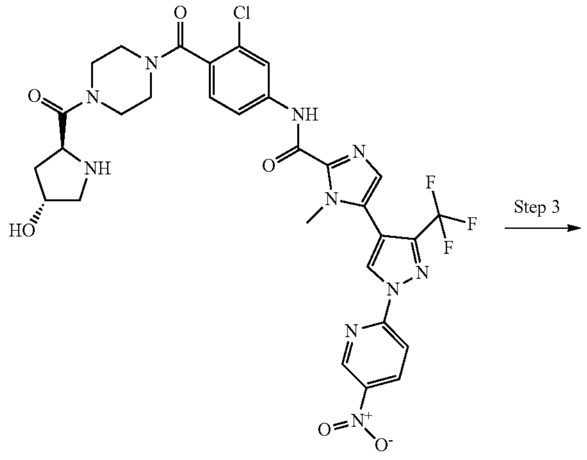

-continued

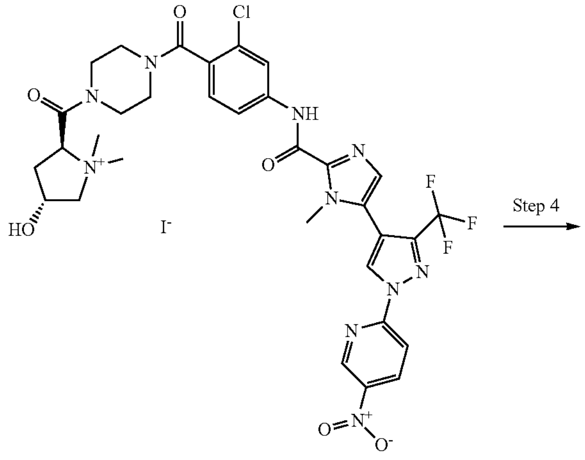

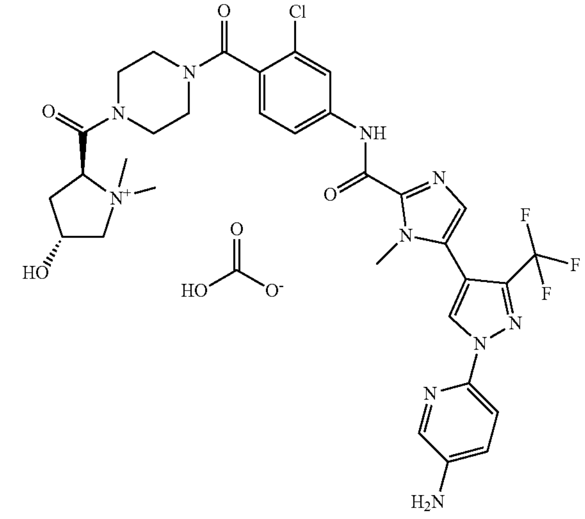

Example D1

Step 1: tert-butyl (2S,4R)-2-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)-4-hydroxypyrrolidine-1-carboxylate In a 50 mL round-bottomed flask, N-(3-chloro-4-(piperazine-1-carbonyl)phenyl)-1-methyl-5-(1-(5-nitropyridin-2-yl)-3-(trifluoromethyl)-pyrazol-4-yl)-imidazole-2-carboxamide (72 mg, 119 μmol), (2S,4R)-1-(tert-butoxycarbonyl)-4-hydroxypyrrolidine-2-carboxylic acid (33.1 mg, 143 μmol), HATU (54.4 mg, 143 μmol) and DIPEA (46.2 mg, 358 μmol) were combined with DMF (3 mL) to give a light yellow solution. The reaction was stirred at room temperature for 1 h. The reaction mixture was poured into 25 mL $H_2O$ and extracted with EtOAc (25 mL×3). The organic layers were combined, washed with sat NaCl (25 mL×1), The organic layers were dried over $Na_2SO_4$ and concentrated in vacuum to afford tert-butyl (2S,4R)-2-(4-(2-chloro-4-(1-methyl-5-(1-(5-nitropyridin-2-yl)-3-(trifluoromethyl)-pyrazol-4-yl)-imidazole-2-carboxamido)benzoyl) piperazine-1-carbonyl)-4-hydroxypyrrolidine-1-carboxylate (97.4 mg). MS $[M+H]^+$: 817.3.

Step 2: N-(3-chloro-4-(4-((2S,4R)-4-hydroxypyrrolidine-2-carbonyl)piperazine-1-carbonyl)phenyl)-1-methyl-5-(1-(5-nitropyridin-2-yl)-3-(trifluoromethyl)-pyrazol-4-yl)-imidazole-2-carboxamide In a 50 mL round-bottomed flask, tert-butyl (2S,4R)-2-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)-4-hydroxypyrrolidine-1-carboxylate (97 mg, 119 μmol) was combined with THE (2 mL) to give a light yellow solution. HCl water solution (989 μl, 11.9 mmol) was added. The reaction was stirred at room temperature for 1 h. The crude reaction mixture was concentrated in vacuum. The crude product was directly used to the next step, to afford N-(3-chloro-4-(4-((2S,4R)-4-hydroxypyrrolidine-2-carbonyl)piperazine-1-carbonyl)phenyl)-1-methyl-5-(1-(5-nitropyridin-2-yl)-3-(trifluoromethyl)-pyrazol-4-yl)-imidazole-2-carboxamide (85.1 mg). MS $[M+H]^+$: 717.1.

Step 3: N-[3-chloro-4-[4-[(2S,4R)-4-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide; iodide In a 50 mL round-bottomed flask, N-(3-chloro-4-(4-((2S,4R)-4-hydroxypyrrolidine-2-carbonyl)piperazine-1-carbonyl)phenyl)-1-methyl-5-(1-(5-nitropyridin-2-yl)-3-(trifluoromethyl)-pyrazol-4-yl)-imidazole-2-carboxamide (85 mg, 119 μmol), MeI (84.1 mg, 593 μmol) and DIPEA (76.6 mg, 593 μmol) were combined with MeCN (5 mL) to give a light brown solution. The reaction mixture was heated to 35° C. and stirred for 2 h.

The crude reaction mixture was concentrated in vacuum. The crude product was directly used to the next step, to afford N-[3-chloro-4-[4-[(2S,4R)-4-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;iodide (88.4 mg). MS $[M+H]^+$: 745.1.

Step 4: 5-[1-(5-amino-2-pyridyl)-3-(trifluoromethyl)pyrazol-4-yl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide; formate In a 50 mL round-bottomed flask, (2S,4R)-2-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)-4-hydroxy-1,1-dimethylpyrrolidin-1-ium (88 mg, 118 μmol) was combined with EtOH (6 mL) to give a light yellow solution. Ammonium chloride (631 mg, 11.8 mmol) in Water (2 mL) was added. Zinc (154 mg, 2.36 mmol) was added. The reaction was stirred at room temperature for 30 min. The crude reaction mixture was concentrated in vacuum. The product was washed with 30 mL of EA:MeOH (10:1), the filtrate was concentrated in vacuum. The crude material was purified by preparative HPLC. to afford (2S,4R)-2-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)-4-hydroxy-1,1-dimethylpyrrolidin-1-ium formate (15.1 mg). MS $[M+H]^+$: 715.3.

The following compounds were prepared in analogy of Example D1.

| Ex# | Name | Structure | MS ESI $[M]^+$ | Starting Material |
|---|---|---|---|---|
| Example D2 | 5-[1-(5-amino-2-pyridyl)-3-(trifluoromethyl)pyrazol-4-yl]-N-[3-chloro-4-[4-[(2S,3.S)-3-hydroxy-1,1-dimethyl-pyrrolidin-1-ium-2-carbonyl]piperazine-1-carbonyl]phenyl]-1-methyl-imidazole-2-carboxamide; formate | 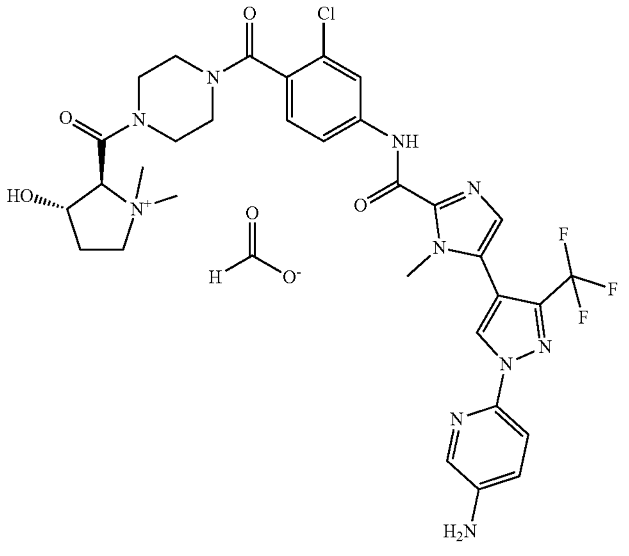 | 742.6 | Intermediate E1 and rac-(2S,3S)-1-tert-butoxycarbonyl-3-hydroxy-pyrrolidine-2-carboxylic acid and iodomethane |

-continued

| Ex# | Name | Structure | MS ESI $[M]^+$ | Starting Material |
|---|---|---|---|---|
| Example D3 | 5-[l-(5-amino-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate | 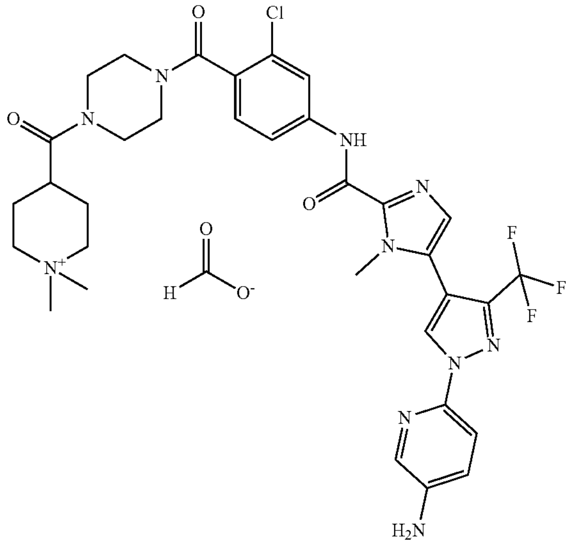 | 713.2 | Intermediate E1 and 1-tert-butoxycarbonylpiperidine-4-carboxylic acid and iodomethane |
| Example D4 | 5-[l-(5-amino-2-pyridyl)-3-(trifluoromethyl)pyrazol-4-yl]-N-[3-chloro-4-[4-(3-hydroxy-1,1-dimethyl-piperidin-1-ium 4-carbonyl)piperazine-1-carbonyl]phenyl]-1-methyl-imidazole-2-carboxamide; formate | 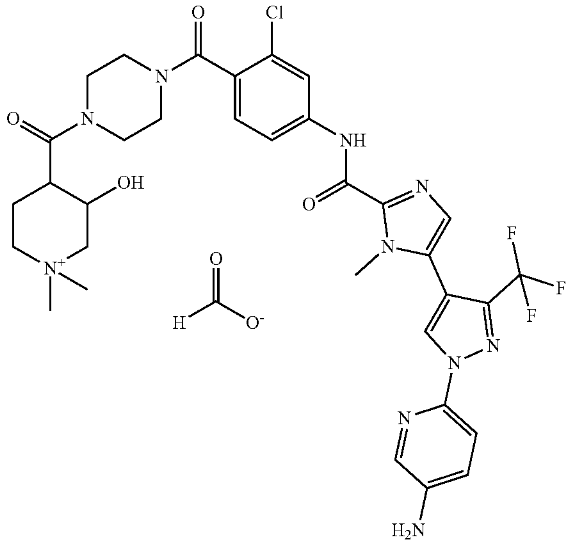 | 729.2 | Intermediate E1 and 1-tert-butoxy carb onyl-3-hydroxy-piperidine-4-carboxylic acid and iodomethane |

-continued

| Ex# | Name | Structure | MS ESI $[M]^+$ | Starting Material |
|---|---|---|---|---|
| Example D5 | 5-[l-(5-amino-2-pyridyl)-3-(trifluoromethyl)pyrazol-4-yl]-N-[3-chloro-4-[4-[(3R,4R)-3-hydroxy-1,1-dimethyl-piperidin-1-ium-4-carbonyl]piperazine-1-carbonyl]phenyl]-1-methyl-imidazole-2-carboxamide; formate | 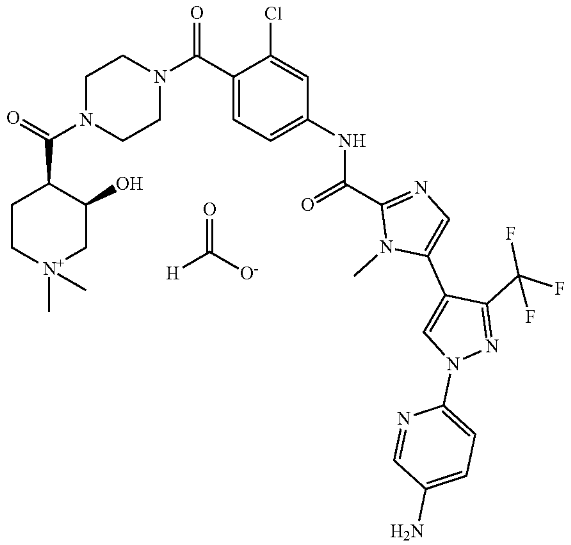 | 729.4 | Intermediate E1 and rac-(3R,4R)-1-tert-butoxycarbonyl-3-hydroxy-piperidine-4-carboxylic acid and iodomethane |
| Example D6 | 5-[l-(5-amino-2-pyridyl)-3-(trifluoromethyl)pyrazol-4-yl]-N-[3-chloro-4-[4-[(3S,4R)-3-hydroxy-1,1-dimethyl-piperidin-1-ium-4-carbonyl]piperazine-1-carbonyl]phenyl]-1-methyl-imidazole-2-carboxamide; formate | 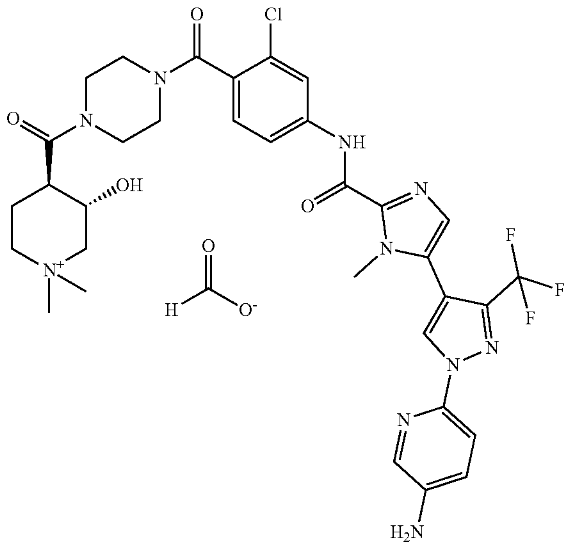 | 729.4 | Intermediate E1 and rac-(3S,4R)-1-tert-butoxycarbonyl-3-hydroxy-piperidine-4-carboxylic acid and iodomethane |

-continued

| Ex# | Name | Structure | MS ESI $[M]^+$ | Starting Material |
| --- | --- | --- | --- | --- |
| Example D7 | 5-[l-(5-amino-2-pyridyl)-3-(trifluoromethyl)pyrazol-4-yl]-N-[3-chloro-4-[4-[(3S,4S)-3-hydroxy-1,1-dimethyl-piperidin-1-ium-4-carbonyl]piperazine-1-carbonyl]phenyl]-1-methyl-imidazole-2-carboxamide; formate | 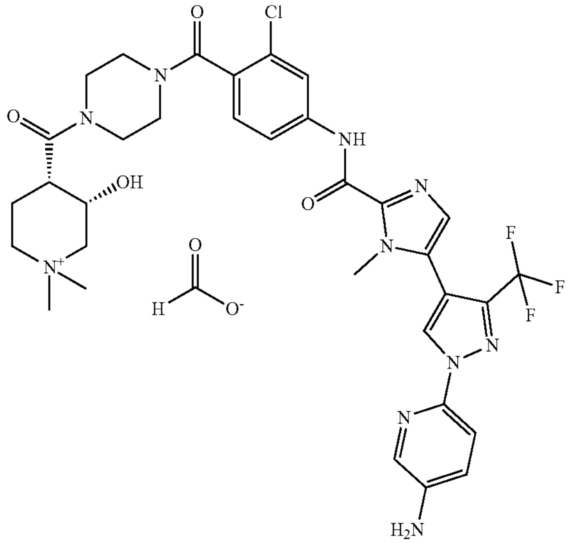 | 729.4 | Intermediate E1 and rac-(3S,4S)-1-tert-butoxycarbonyl-3-hydroxy-piperidine-4-carboxylic acid and iodomethane |
| Example D8 | 5-[1-(5-amino-2-pyridyl)-3-(trifluoromethyl)pyrazol-4-yl]-N-[3-chloro-4-[4-[(3R,4S)-3-hydroxy-1,1-dimethyl-piperidin-1-ium-4-carbonyl]piperazine-1-carbonyl]phenyl]-1-methyl-imidazole-2-carboxamide; formate | 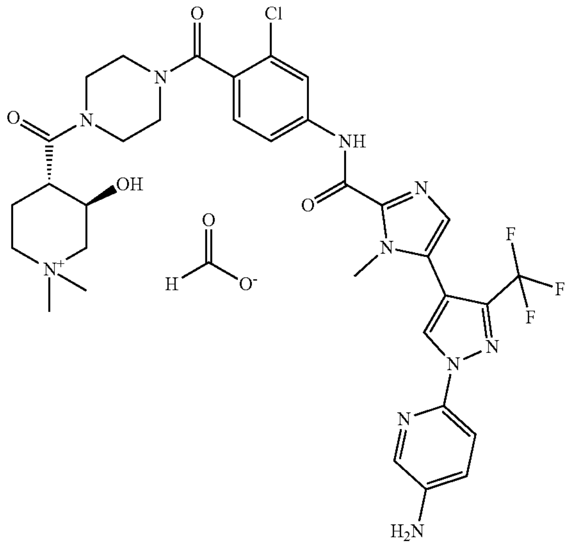 | 729.3 | Intermediate E1 and rac-(3R,4S)-1-tert-butoxycarbonyl-3-hydroxy-piperidine-4-carboxylic acid and iodomethane |

-continued

| Ex# | Name | Structure | MS ESI $[M]^+$ | Starting Material |
|---|---|---|---|---|
| Example D10 | 5-[l-(5-amino-2-pyridyl)-3-(trifluoromethyl)pyrazol-4-yl]-N-[3-chloro-4-[4-(4-hydroxy-1,1-dimethyl-piperidin-1-ium-4-carbonyl)piperazine-1-carbonyl]phenyl]-1-methyl-imidazole-2-carboxamide; formate | 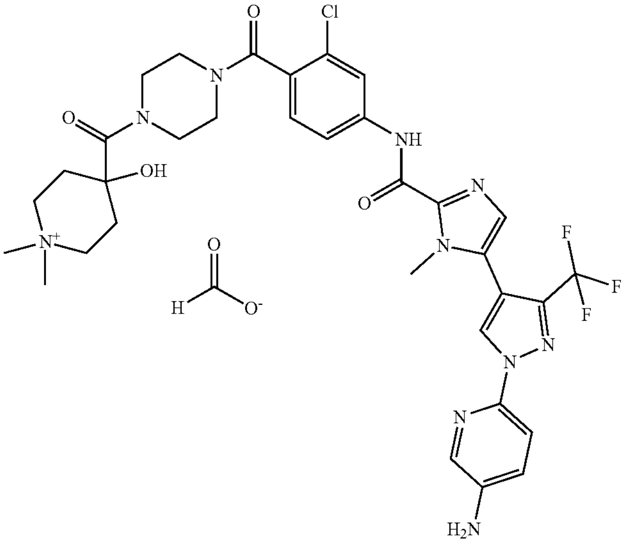 | 729.4 | Intermediate E11 and iodomethane |
| Example D11 | 5-[l-(5-amino-2-pyridyl)-3-(trifluoromethyl)pyrazol-4-yl]-N-[3-chloro-4-[4-[2-(3-hydroxy-1-methyl-pyrrolidin-1-ium-1-yl)acetyl]piperazine-1-carbonyl]phenyl]-1-methyl-imidazole-2-carboxamide; formate | 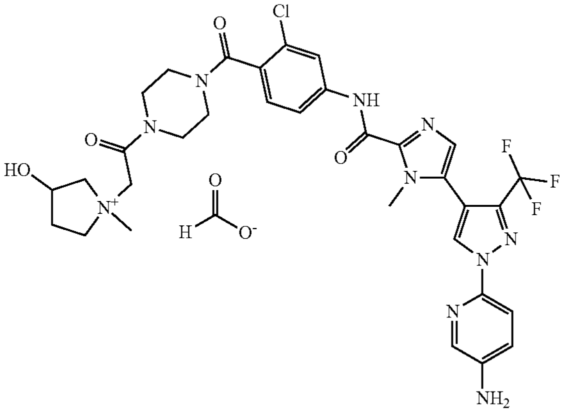 | 715.5 | Intermediate F1 and iodomethane |
| Example D12 | 5-[l-(5-amino-2-pyridyl)-3-(trifluoromethyl)pyrazol-4-yl]-N-[3-chloro-4-[[l-(1,1-dimethylpiperidin-1-ium-4-carbonyl)-4-piperidyl]methylcarbamoyl]phenyl]-1-methyl-imidazole-2-carboxamide; formate | 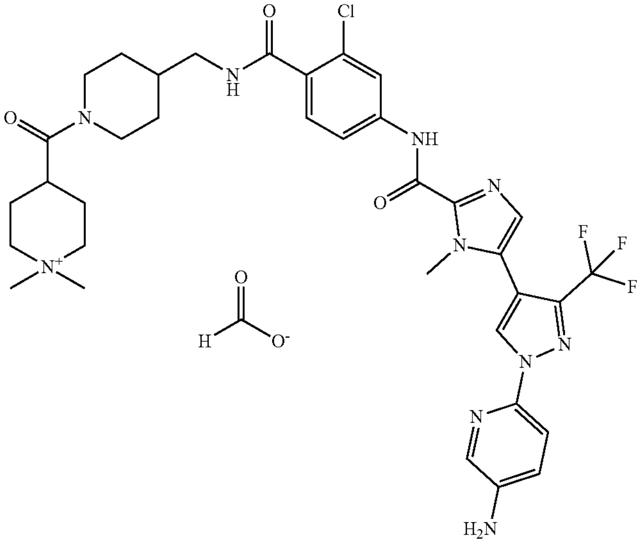 | 741.5 | Intermediate E13 and iodomethane |

-continued

| Ex# | Name | Structure | MS ESI $[M]^+$ | Starting Material |
|---|---|---|---|---|
| Example D13 | 5-[l-(5-amino-2-pyridyl)-3-(trifluoromethyl)pyrazol-4-yl]-N-[3-chloro-4-[4-[(3S)-4,4-dimethylmorpholin-4-ium-3-carbonyl]piperazine-1-carbonyl]phenyl]-1-methyl-imidazole-2-carboxamide; formate | 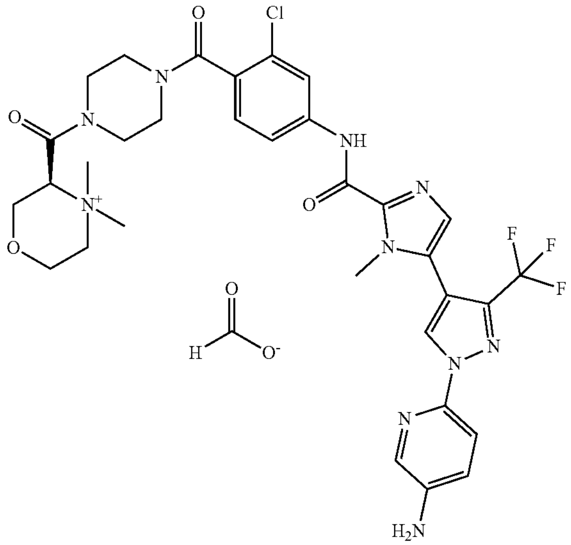 | 715.4 | Intermediate E14 and iodomethane |
| Example D14 | N-[4-[4-[(2S,3S)-3-[(5-amino-2-pyridyl)oxy]-1,1-dimethyl-pyrrolidin-l-ium-2-carbonyl]piperazine-1-carbonyl]-3-chloro-phenyl]-5-[1-(5-amino-2-pyridyl)-3-(trifluoromethyl)pyrazol-4-yl]-1-methyl-imidazole-2-carboxamide; formate | 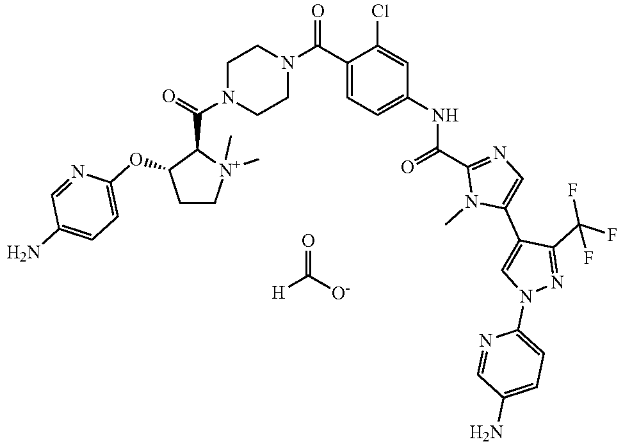 | 807.5 | Intermediate D29 and iodomethane |
| Example D16 | 5-[1-(5-aminopyrazin-2-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate | 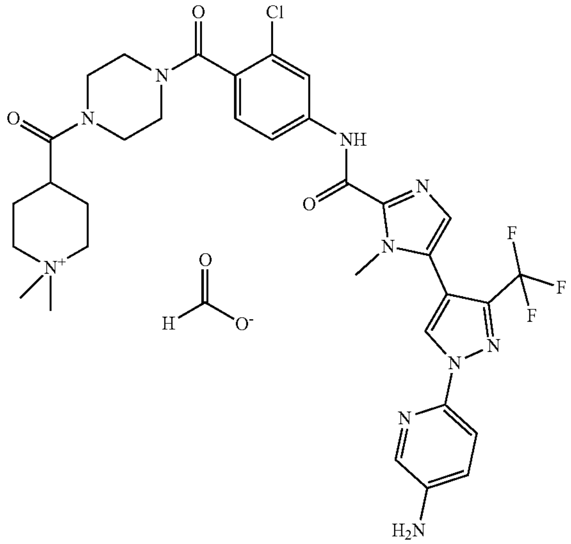 | 714.3 | Intermediate E21 and iodomethane |

-continued

| Ex# | Name | Structure | MS ESI [M]+ | Starting Material |
|---|---|---|---|---|
| Example D17 | 5-[l-(5-amino-2-pyridyl)-3-(trifluoromethyl)pyrazol-4-yl]-N-[3-chloro-4-[[(exo)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-1-methyl-imidazole-2-carboxamide; 1:1 formate | 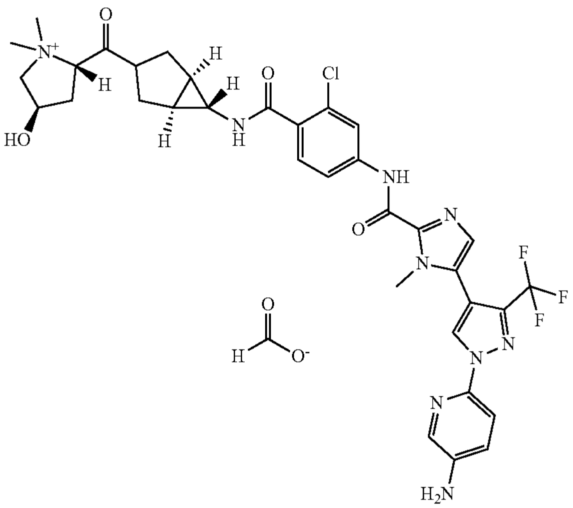 | 727.2 | Intermediate E22 and iodomethane |

Example D15

5-[1-(5-Amino-2-pyridyl)-3-(trifluoromethyl)pyrazol-4-yl]-N-[3-chloro-4-[4-[(2S)-4-hydroxy-1,1-dimethyl-piperidin-1-ium-2-carbonyl]piperazine-1-carbonyl]phenyl]-1-methyl-imidazole-2-carboxamide;formate

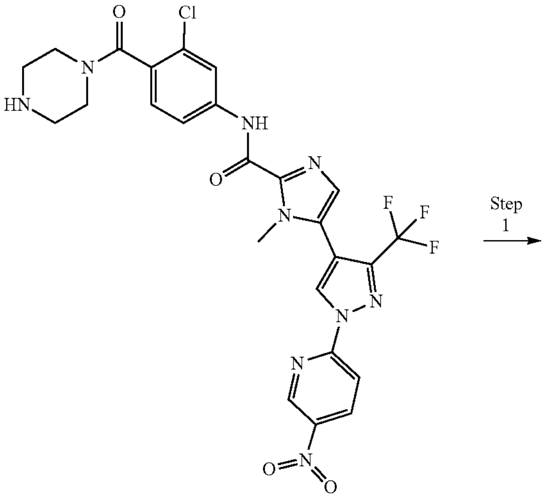

Intermediate E1

-continued

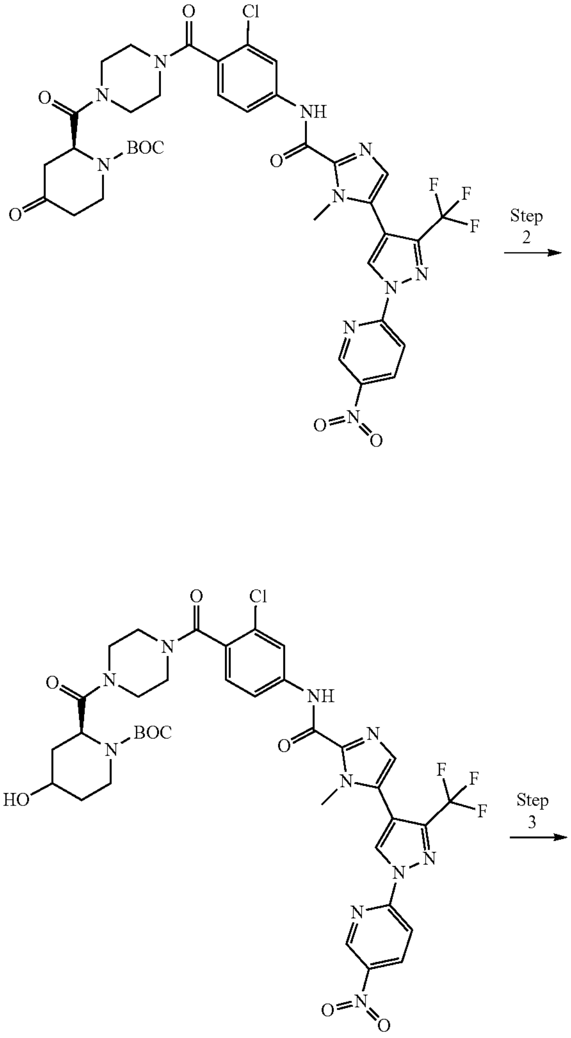

-continued

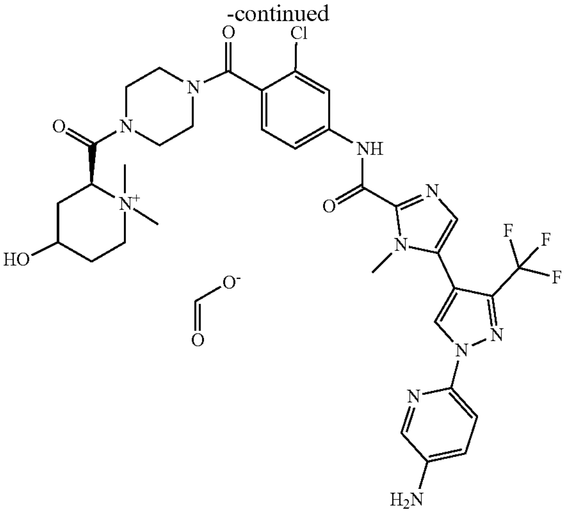

Example D15

Step 1: tert-butyl (2S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-4-oxo-piperidine-1-carboxylate Intermediate E1 (300 mg, 0.5 mmol), 1-(tert-butoxycarbonyl)-4-oxopiperidine-2-carboxylic acid (135.2 mg, 0.6 mmol), HATU (193.6 mg, 0.5 mmol) and DIEA (299.2 mg, 404.3 uL, 2.3 mmol) were stirred in acetonitrile (4.6 mL) at 25° C. for 0.5 h. The solvent was removed in vacuum, and the residue was purified by flash chromatography to yield the title compound as light yellow oil, 380 mg. MS $[M+H]^+$: 829.9.

Step 2: N-[3-chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide (2S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-4-keto-piperidine-1-carboxylic acid tert-butyl ester (500 mg, 0.6 mmol) was dissolved in methanol (6.0 mL), $NaBH_4$ (22.8 mg, 0.6 mmol) was added in one portion. The mixture was stirred at rt for 30 min. Then 5 mL 1M HCl/MeOH solution was added, and the stirring was continued for 3 h. The solvent was removed in vacuum, the residue was neutralized with TEA and purified by flash chromatography to yield the title compound as light yellow oil, 350 mg. MS $[M+H]^+$: 731.4.

Step 3: 5-[1-(5-amino-2-pyridyl)-3-(trifluoromethyl)pyrazol-4-yl]-N-[3-chloro-4-[4-[(2S)-4-hydroxy-1,1-dimethyl-piperidin-1-ium-2-carbonyl]piperazine-1-carbonyl]phenyl]-1-methyl-imidazole-2-carboxamide; formate N-[3-chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide (200 mg, 0.3 mmol), DIEA (354 mg, 448 uL, 2.7 mmol) and iodomethane (116 mg, 51.3 uL, 0.8 mmol) were stirred in ethanol (4 mL) at rt for 18 h. The solvent was removed in vacuum. The residue was dissolve in ethanol (4 mL) and 1 mL water. To this solution was added ammonium chloride (74.8 mg, 1.4 mmol) and zinc (182.9 mg, 2.8 mmol). The mixture was stirred at rt for 3 h. The mixture was filtered, the filtrate was concentrated in vacuum, the residue was dissolved in DMF and purified by preparative HPLC to give the title compound as light yellow powder, 19 mg. MS $[M]^+$: 729.5.

Example D18

(exo)-6-[[4-[[5-[1-(5-Aminopyridin-2-yl)-3-(trifluoromethyl)pyrazol-4-yl]-1-methylimidazole-2-carbonyl]amino]-2-chlorobenzoyl]amino]-N-[rac-(trans)-4-hydroxy-1,1-dimethylpyrrolidin-1-ium-3-yl]-3-azabicyclo[3.1.0]hexane-3-carboxamide; formate

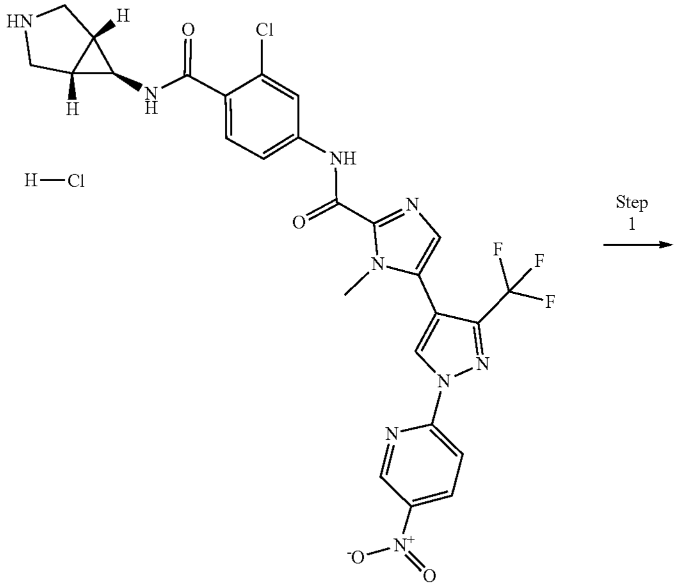

Intermediate E23

-continued
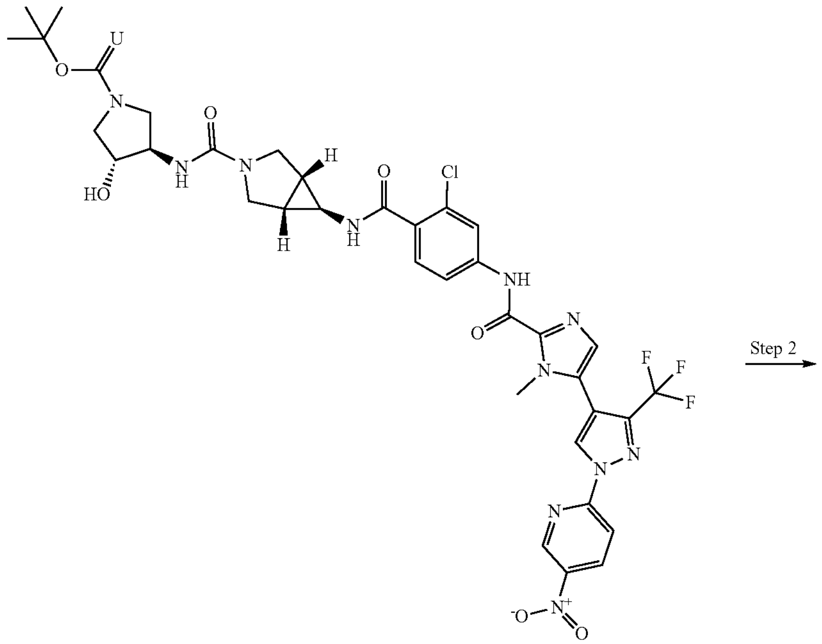
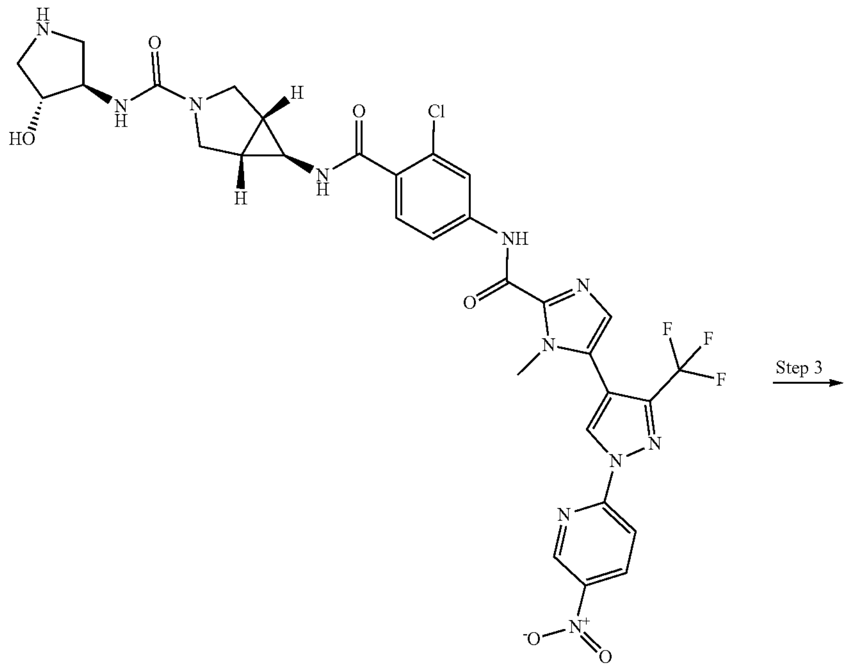

-continued

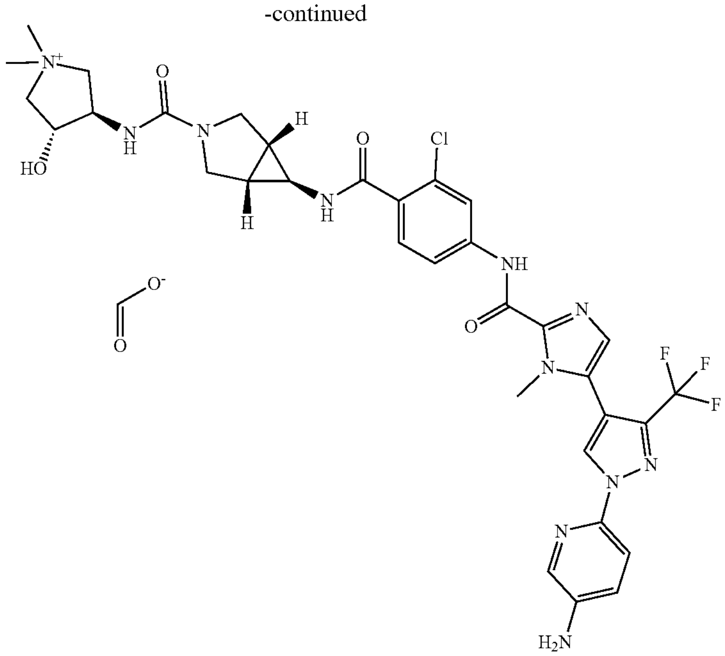

Example D18

Step 1: (trans)-3-[[(exo)-6-[[2-chloro-4-[[1-methyl-5-[1-(5-nitro-2-pyridyl)-3-(trifluoromethyl)pyrazol-4-yl]imidazole-2-carbonyl]amino]benzoyl]amino]-3-azabicyclo[3.1.0]hexane-3-carbonyl]amino]-4-hydroxy-pyrrolidine-1-carboxylic acid tert-butyl ester 3-amino-4-hydroxy-pyrrolidine-1-carboxylic acid tert-butyl ester (93.05 mg, 0.460 mmol, 1.5 eq) was added to a stirred solution of CDI (74.6 mg, 0.460 mmol, 1.5 eq) and $Et_3N$ (155.18 mg, 213.75 uL, 1.53 mmol, 5 eq) dissolved in N,N-dimethylformamide (14.24 mL) at 0° C. The reaction mixture was stirred for 0.5 h, and then N-[4-[[(exo)-3-azabicyclo[3.1.0]hexan-6-yl]carbamoyl]-3-chloro-phenyl]-1-methyl-5-[1-(5-nitro-2-pyridyl)-3-(trifluoromethyl)pyrazol-4-yl]imidazole-2-carboxamide;hydrogen chloride (230 mg, 0.307 mmol, 1 eq) was added. The ice bath was removed, and the reaction mixture was stirred for 2 h and allowed to warm to RT. The reaction mixture was poured into water (20 mL), and then extracted with EtOAc. The organic layer was washed with 5% LiCl-solution and brine, and concentrated. The crude residue was purified by flash chromatography (MeOH/DCM 1:9 in DCM, 0-70%, 12 g) to give the title compound (106 mg, 40.94%) as orange solid. MS $[M-H]^-$: 842.2.

Step 2: (exo)-6-[[2-chloro-4-[[1-methyl-5-[1-(5-nitro-2-pyridyl)-3-(trifluoromethyl)pyrazol-4-yl]imidazole-2-carbonyl]amino]benzoyl]amino]-N-[(trans)-4-hydroxypyrrolidin-3-yl]-3-azabicyclo[3.1.0]hexane-3-carboxamide; hydrogen chloride (trans)-3-[[(exo)-6-[[2-chloro-4-[[1-methyl-5-[1-(5-nitro-2-pyridyl)-3-(trifluoromethyl)pyrazol-4-yl]imidazole-2-carbonyl]amino]benzoyl]amino]-3-azabicyclo[3.1.0]hexane-3-carbonyl]amino]-4-hydroxy-pyrrolidine-1-carboxylic acid tert-butyl ester (45 mg, 0.053 mmol, 1 eq) was combined with dichloromethane (1 mL). 4 M HCl in dioxane (79.96 mg, 66.63 uL, 0.267 mmol, 5 eq) was added, and the reaction mixture was stirred for 2 h. The solvents were evaporated to afford crude (42 mg, 99.9%) as a yellow solid, which was directly used for the next step. MS $[M+H]^+$: 744.2.

Step 3: (exo)-6-[[4-[[5-[1-(5-Aminopyridin-2-yl)-3-(trifluoromethyl)pyrazol-4-yl]-1-methylimidazole-2-carbonyl]amino]-2-chlorobenzoyl]amino]-N-[rac-(trans)-4-hydroxy-1,1-dimethylpyrrolidin-1-ium-3-yl]-3-azabicyclo[3.1.0]hexane-3-carboxamide; formate A mixture of (exo)-6-[[2-chloro-4-[[1-methyl-5-[1-(5-nitro-2-pyridyl)-3-(trifluoromethyl)pyrazol-4-yl]imidazole-2-carbonyl]amino]benzoyl]amino]-N-[(trans)-4-hydroxypyrrolidin-3-yl]-3-azabicyclo[3.1.0]hexane-3-carboxamide; hydrochloride (41.6 mg, 0.053 mmol, 1 eq) in acetonitrile (2.88 mL) was treated with DIPEA (20.66 mg, 27.92 uL, 0.160 mmol, 3 eq) and iodomethane (18.91 mg, 8.33 uL, 0.133 mmol, 2.5 eq). After the mixture was stirred at RT for 1 h, the solvents were evaporated at HV, and the crude residue was directly used for the next step. A mixture of crude residue (40 mg, 0.052 mmol, 1 eq) was combined with ammonium chloride (138.19 mg, 2.58 mmol, 50 eq), water (0.500 mL) and ethanol (1.5 mL). Zinc (67.56 mg, 1.03 mmol, 20 eq) was added, and the reaction mixture was stirred over night. The reaction mixture was filtered, and then purified by prep HPLC to afford the title compound (25 mg, 60%) as an off-white solid. MS $[M]^+$: 742.5.

Example E1
N-[3-Chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate
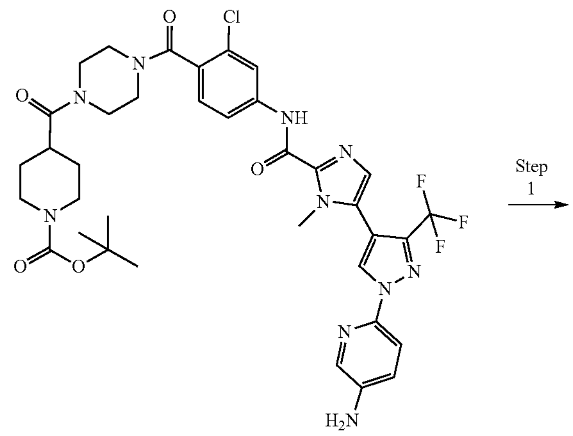
intermediate G1
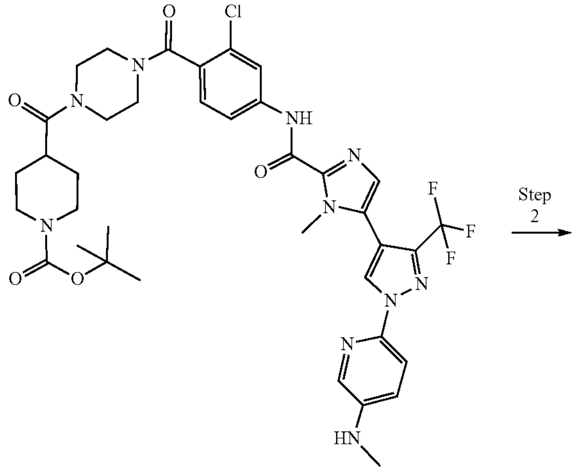
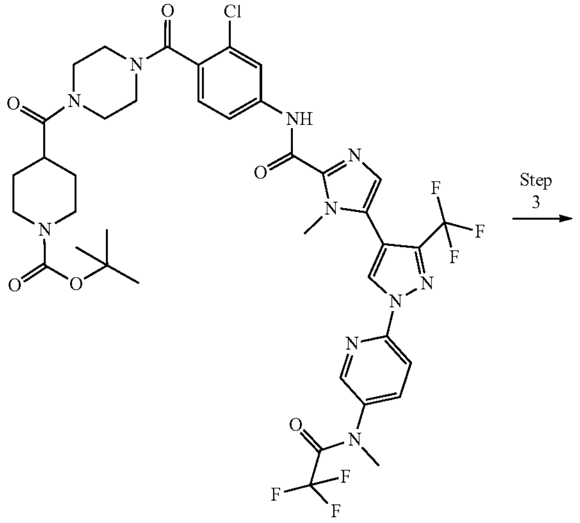
-continued
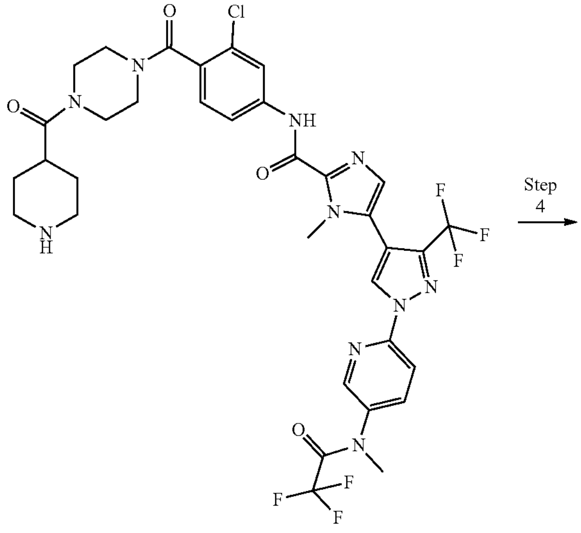
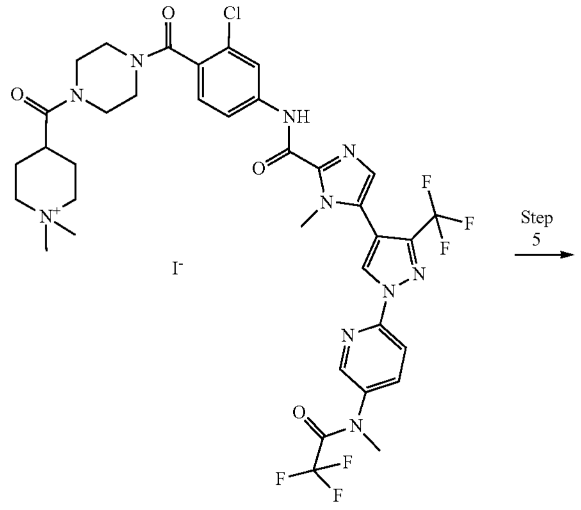
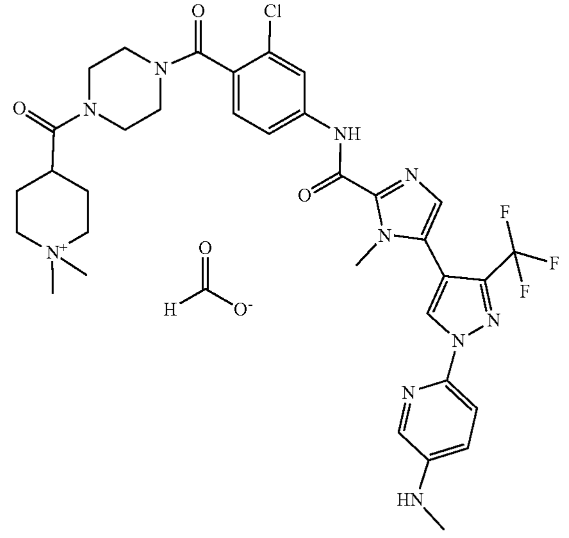
Example E1

Step 1: tert-butyl 4-(4-(2-chloro-4-(1-methyl-5-(1-(5-(methylamino)pyridin-2-yl)-3-(trifluoromethyl)-pyrazol-4-yl)-imidazole-2-carboxamido)benzoyl) piperazine-1-carbonyl)piperidine-1-carboxylate To a 25 mL microwave vial was added tert-butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate (240 mg, 306 μmol), formaldehyde (275 mg, 9.17 mmol) and sodium methoxide (495 mg, 9.17 mmol) in MeOH (10 mL). The vial was capped and heated under microwave at 50° C. for 15 h. The reaction was cooled to the room temperature, $NaBH_4$ (405 mg, 10.7 mmol) was added. The reaction stirred at room temperature for 2 h. The crude reaction mixture was concentrated in vacuum. The reaction mixture was poured into 25 mL sat $NH_4Cl$ and extracted with EtOAc (25 mL×3). sat NaCl (25 mL×1), The organic layers were dried over $Na_2SO_4$ and concentrated in vacuum to afford tert-butyl 4-(4-(2-chloro-4-(1-methyl-5-(1-(5-(methylamino)pyridin-2-yl)-3-(trifluoromethyl)-pyrazol-4-yl)-imidazole-2-carboxamido)benzoyl)piperazine-1-carbonyl)piperidine-1-carboxylate (169 mg). MS $[M+H]^+$:799.7.

Step 2: tert-butyl 4-(4-(2-chloro-4-(1-methyl-5-(1-(5-(2,2,2-trifluoro-N-methylacetamido)pyridin-2-yl)-3-(trifluoromethyl)-pyrazol-4-yl)-imidazole-2-carboxamido)benzoyl)piperazine-1-carbonyl) piperidine-1-carboxylate In a 50 mL round-bottomed flask, tert-butyl 4-(4-(2-chloro-4-(1-methyl-5-(1-(5-(methylamino)pyridin-2-yl)-3-(trifluoromethyl)-pyrazol-4-yl)-imidazole-2-carboxamido) benzoyl)piperazine-1-carbonyl)piperidine-1-carboxylate (160 mg, 200 μmol), 2,2,2-trifluoroacetic anhydride (84.1 mg, 400 μmol) and DIPEA (129 mg, 1 mmol) were combined with DCM (3 mL) to give a light yellow solution. The reaction was stirred at room temperature for 1 h. The crude reaction mixture was concentrated in vacuum. The crude product was directly used to the next step, to afford tert-butyl 4-(4-(2-chloro-4-(1-methyl-5-(1-(5-(2,2,2-trifluoro-N-methylacetamido)pyridin-2-yl)-3-(trifluoromethyl)-pyrazol-4-yl)-imidazole-2-carboxamido)benzoyl)piperazine-1-carbonyl)piperidine-1-carboxylate (179 mg). MS $[M+H]^+$: 895.3.

Step 3: N-(3-chloro-4-(4-(piperidine-4-carbonyl) piperazine-1-carbonyl)phenyl)-1-methyl-5-(1-(5-(2,2,2-trifluoro-N-methylacetamido)pyridin-2-yl)-3-(trifluoromethyl)-pyrazol-4-yl)-imidazole-2-carboxamide In a 50 mL round-bottomed flask, tert-butyl 4-(4-(2-chloro-4-(1-methyl-5-(1-(5-(2,2,2-trifluoro-N-methylacetamido)pyridin-2-yl)-3-(trifluoromethyl)-pyrazol-4-yl)-imidazole-2-carboxamido)benzoyl)piperazine-1-carbonyl) piperidine-1-carboxylate (170 mg, 190 μmol) was combined with THE (1 mL) to give a light yellow solution. HCl water solution (3.46 g, 94.9 mmol) was added. The reaction was stirred at room temperature for 1 h. The crude reaction mixture was concentrated in vacuum. the crude product was directly used to the next step to afford N-(3-chloro-4-(4-(piperidine-4-carbonyl)piperazine-1-carbonyl)phenyl)-1-methyl-5-(1-(5-(2,2,2-trifluoro-N-methylacetamido)pyridin-2-yl)-3-(trifluoromethyl)-pyrazol-4-yl)-imidazole-2-carboxamide (151 mg). MS $[M+H]^+$:795.5.

Step 4: N-[3-chloro-4-[4-(1,1-dimethylpiperidin-1-ium-4-carbonyl)piperazine-1-carbonyl]phenyl]-1-methyl-5-[1-[5-[methyl-(2,2,2-trifluoroacetyl) amino]-2-pyridyl]-3-(trifluoromethyl)pyrazol-4-yl] imidazole-2-carboxamide; iodide In a 100 mL round-bottomed flask, N-(3-chloro-4-(4-(piperidine-4-carbonyl)piperazine-1-carbonyl)phenyl)-1-methyl-5-(1-(5-(2,2,2-trifluoro-N-methylacetamido)pyridin-2-yl)-3-(trifluoromethyl)-pyrazol-4-yl)-imidazole-2-carboxamide (151 mg, 190 μmol) was combined with MeCN (6 mL) to give a light yellow solution. DIPEA (73.6 mg, 570 μmol) and MeI (135 mg 950 μmol) were added. The reaction was stirred at room temperature for 1 h. The crude reaction mixture was concentrated in vacuum. The crude product was directly used to the next step, to afford N-[3-chloro-4-[4-(1,1-dimethylpiperidin-1-ium-4-carbonyl)piperazine-1-carbonyl]phenyl]-1-methyl-5-[1-[5-[methyl-(2,2,2-trifluoroacetyl)amino]-2-pyridyl]-3-(trifluoromethyl) pyrazol-4-yl]imidazole-2-carboxamide; iodide (157 mg). MS $[M+H]^+$: 823.4.

Step 5: N-[3-chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate In a 100 mL round-bottomed flask, 4-(4-(2-chloro-4-(1-methyl-5-(1-(5-(2,2,2-trifluoro-N-methylacetamido)pyridin-2-yl)-3-(trifluoromethyl)-pyrazol-4-yl)-imidazole-2-carboxamido)benzoyl)piperazine-1-carbonyl)-1,1-dimethylpiperidin-1-ium (150 mg, 182 μmol) was combined with MeOH (6 mL) to give a light yellow solution. $K_2CO_3$ (2.52 g, 18.2 mmol) was added. The reaction was stirred at room temperature for 1 h. The reaction mixture was filtered through glass fiber paper. The filtrate was concentrated in vacuum. The crude material was purified by preparative HPLC. to afford N-[3-chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate (31 mg). MS:727.3.

The following compounds were prepared in analogy of Example E1.

| Ex# | Name | Structure | MS ESI [M + H]+ | Starting Material |
|---|---|---|---|---|
| Example E2 | N-[3-chloro-4-[4-(1,1-dimethylpiperidin-l-ium-4-carbonyl)piperazine-1-carbonyl]phenyl]-5-[1-[5-(2-methoxyethylamino)-2-pyridyl]-3-(trifluoromethyl)pyrazol-4-yl]-l-methyl-imidazole-2-carboxamide; formate | 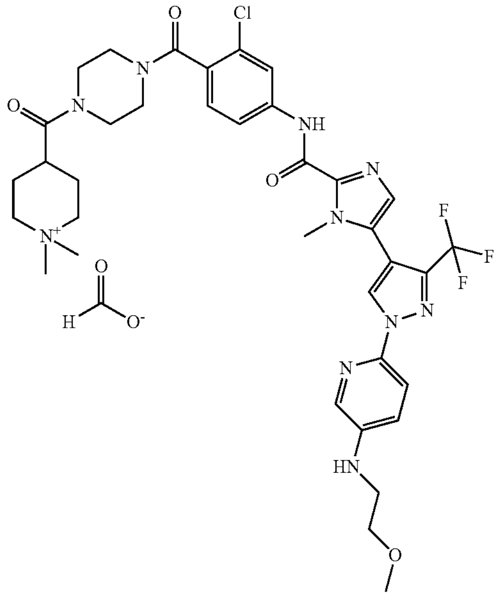 | 771.6 | Intermediate D11 and TFAA and iodomethane |
| Example E3 | N-[3-chloro-4-[4-(1,1-dimethylpiperidin-1-ium-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide; formate | 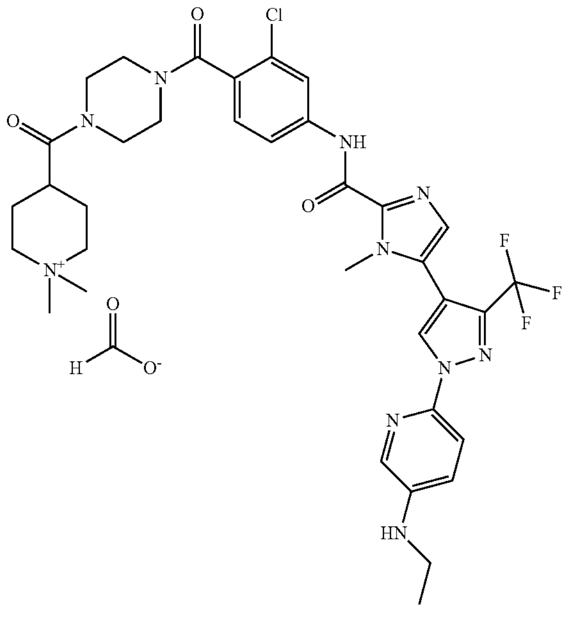 | 741.5 | Intermediate H1 and TFAA and iodomethane |

-continued

| Ex# | Name | Structure | MS ESI [M + H]+ | Starting Material |
|---|---|---|---|---|
| Example E4 | N-[3-chloro-4-[4-(4-hydroxy-1,1-dimethyl-piperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formate | 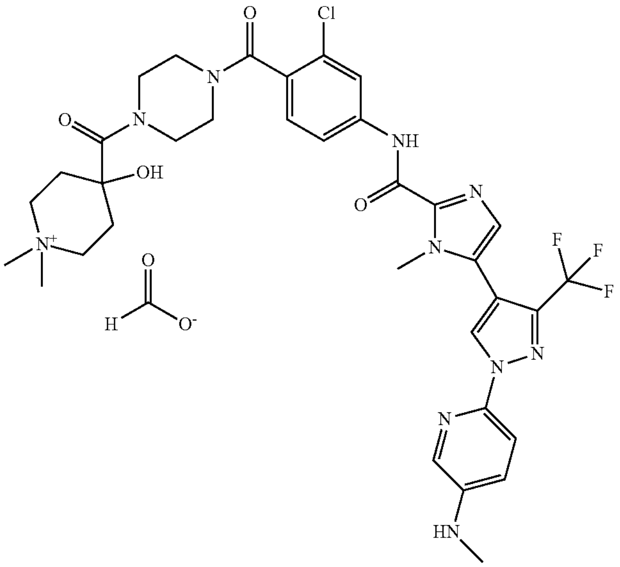 | 743.4 | Intermediate G2 and TFAA and iodomethane |
| Example E5 | N-[3-chloro-4-[4-[2-(3-hydroxy-1-methyl-pyrrolidin-1-ium-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate | 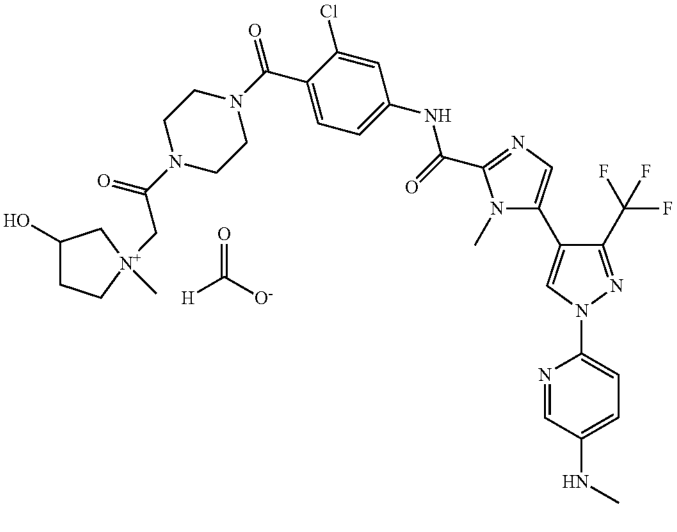 | 729.5 | Intermediate G3 and TFAA and iodomethane |

-continued

| Ex# | Name | Structure | MS ESI [M + H]+ | Starting Material |
|---|---|---|---|---|
| Example E6 | N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate | 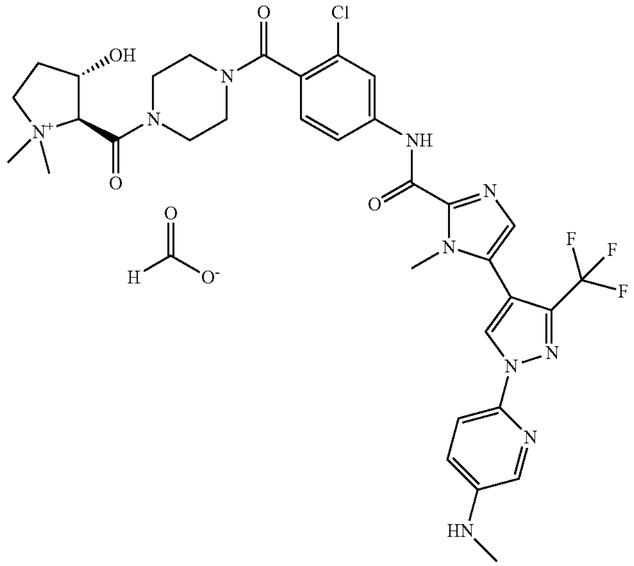 | 729.5 | Intermediate G4 and TFAA and iodomethane |
| Example E7 | N-[4-[4-(1,1-dimethylpiperidin-1-ium-4-carbonyl)piperazine-1-carbonyl]-3-methyl-phenyl]-1-methyl-5-[1-[5-(methylamino)-2-pyridyl]-3-(trifluoromethyl)pyrazol-4-yl]imidazole-2-carboxamide; formate | 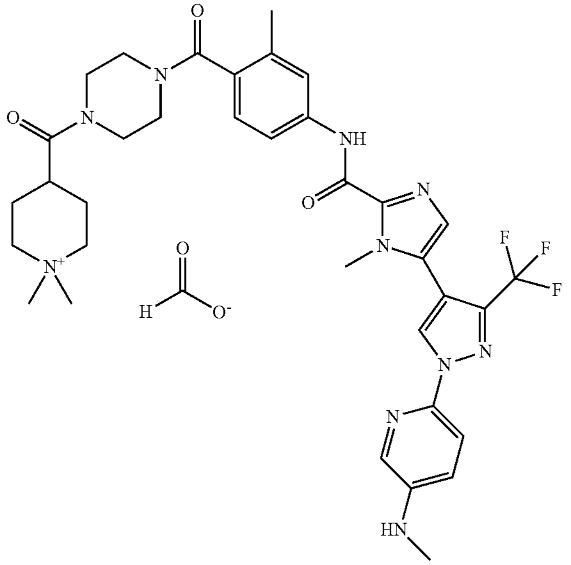 | 707.4 | Intermediate G5 and TFAA and iodomethane |

-continued

| Ex# | Name | Structure | MS ESI [M + H]+ | Starting Material |
|---|---|---|---|---|
| Example E8 | N-[3-chloro-4-[4-[(3S,4R)-3-hydroxy-1,1-dimethyl-piperidin-1-ium-4-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formate | 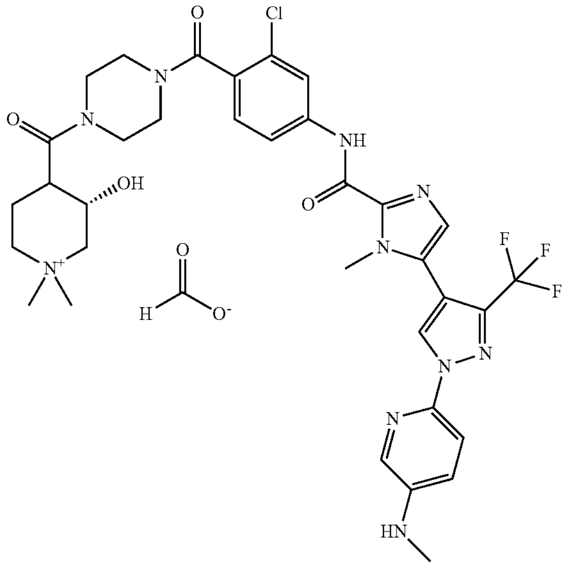 | 744.2 | Intermediate G6 and TFAA and iodomethane |

Example F1

N-[3-Chloro-4-[4-(1,1-dimethylpiperidin-1-ium-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide; formate

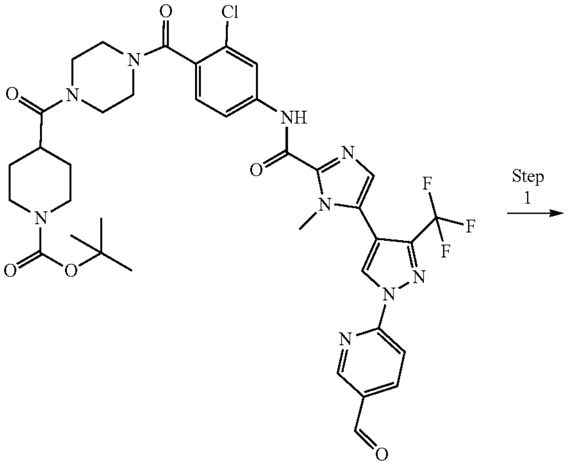

Intermediate D7

-continued

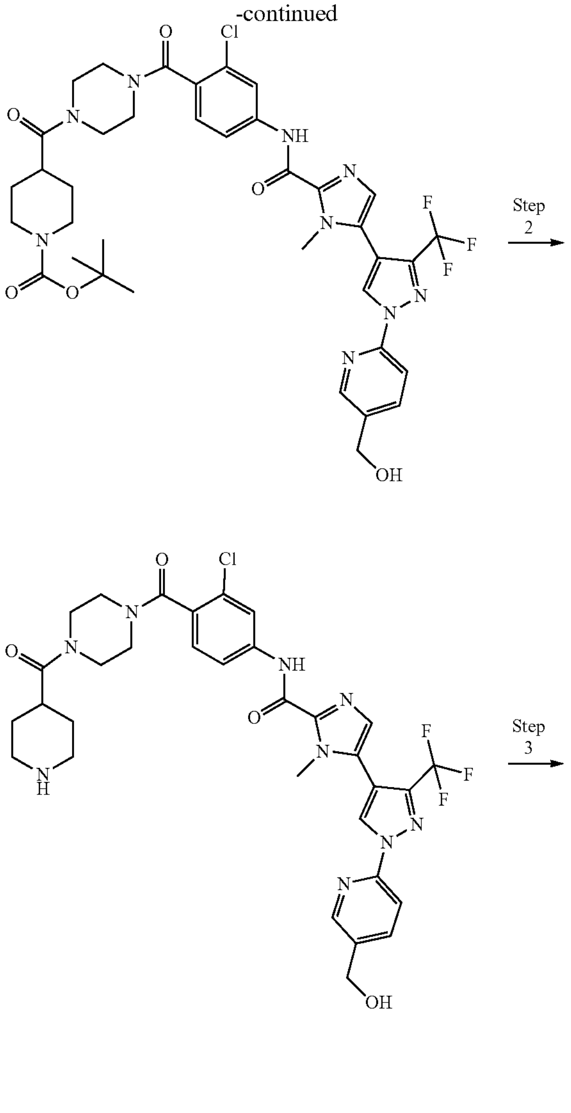

-continued

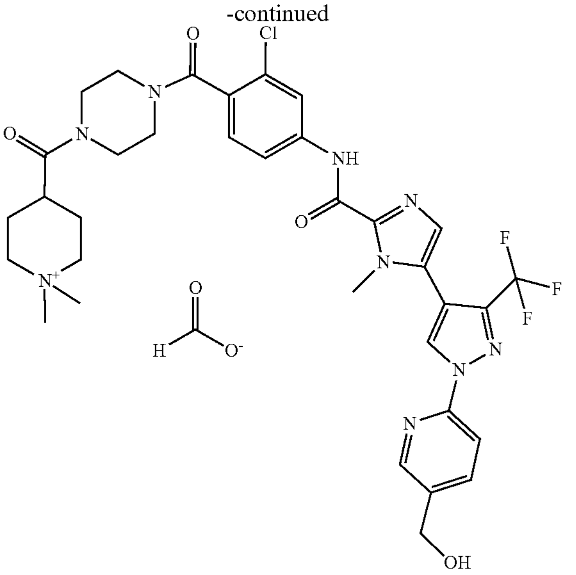

Example F1

Step 1: tert-butyl 4-[4-[2-chloro-4-[[5-[1-[5-(hydroxymethyl)-2-pyridyl]-3-(trifluoromethyl)pyrazol-4-yl]-1-methyl-imidazole-2-carbonyl]amino]benzoyl]piperazine-1-carbonyl]piperidine-1-carboxylate 4-[4-[2-chloro-4-[[5-[1-(5-formyl-2-pyridyl)-3-(trifluoromethyl)pyrazol-4-yl]-1-methyl-imidazole-2-carbonyl]amino]benzoyl]piperazine-1-carbonyl]piperidine-1-carboxylic acid tert-butyl ester (69 mg, 0.086 mmol) was dissolved in methanol (5 mL), and NaBH4 (32.7 mg, 0.864 mmol) was added at rt. The mixture was stirred for 30 min at room temperature. The reaction was concentrated under vacuum, the crude product was directly used to the next step to afford tert-butyl 4-[4-[2-chloro-4-[[5-[1-[5-(hydroxymethyl)-2-pyridyl]-3-(trifluoromethyl)pyrazol-4-yl]-1-methyl-imidazole-2-carbonyl]amino]benzoyl]piperazine-1-carbonyl]piperidine-1-carboxylate (69 mg). MS $[M+H]^+$: 800.7.

Step 2: N-[3-chloro-4-[4-(piperidine-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide 4-[4-[2-chloro-4-[[1-methyl-5-[1-(5-methylol-2-pyridyl)-3-(trifluoromethyl)pyrazol-4-yl]imidazole-2-carbonyl]amino]benzoyl]piperazine-1-carbonyl]piperidine-1-carboxylic acid tert-butyl ester (69 mg, 0.086 mmol) was dissolved in tetrahydrofuran (2 mL), 12 M HCl water solution (718.54 uL, 8.62 mmol) was added at rt. The mixture was stirred for 1 h at room temperature. the reaction was concentrated under vacuum, the crude product was directly used to the next step to afford N-[3-chloro-4-[4-(piperidine-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide (60.3 mg). MS $[M+H]^+$: 700.3.

Step 3: N-[3-chloro-4-[4-(1,1-dimethylpiperidin-1-ium-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide; formate N-[3-chloro-4-(4-isonipecotoylpiperazine-1-carbonyl)phenyl]-1-methyl-5-[1-(5-methylol-2-pyridyl)-3-(trifluoromethyl)pyrazol-4-yl]imidazole-2-carboxamide (60.3 mg, 0.086 mmol) was dissolved in acetonitrile (2 mL) acetonitrile (2 mL), DIEA (55.66 mg, 0.431 mmol) and iodomethane (61.13 mg, 0.431 mmol) was added at rt. The mixture was stirred for 1 h at room temperature. The reaction was concentrated under vacuum, the crude product was prepared by HPLC to afford N-[3-chloro-4-[4-(1,1-dimethylpiperidin-1-ium-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide; formate (18 mg). MS: $[M+H]^+$: 728.4.

Example G1

N-[3-Chloro-4-[4-(1,1-dimethylpiperidin-1-ium-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formate

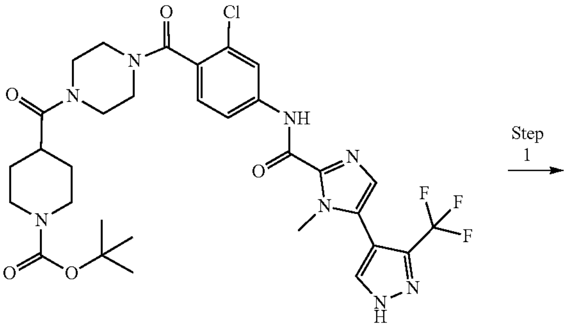

Intermediate C3

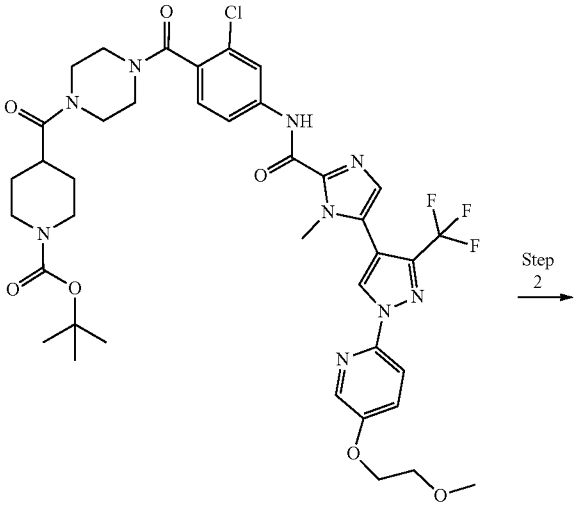

-continued

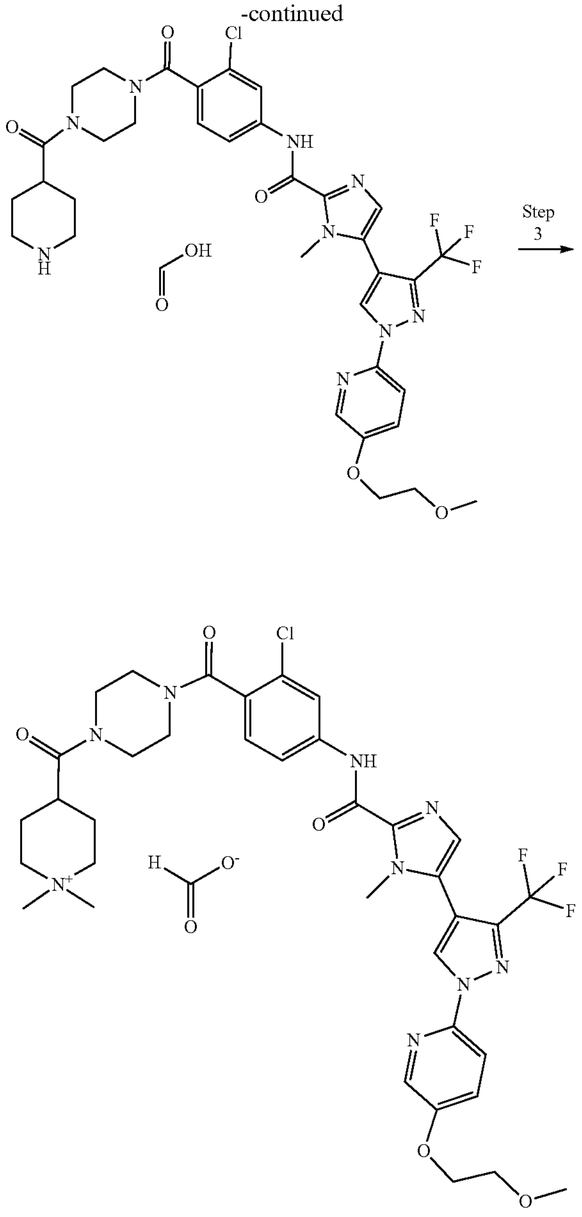

Example G1

Step 1: tert-butyl 4-[4-[2-chloro-4-[[5-[1-[5-(2-methoxyethoxy)-2-pyridyl]-3-(trifluoromethyl)pyrazol-4-yl]-1-methyl-imidazole-2-carbonyl]amino]benzoyl]piperazine-1-carbonyl]piperidine-1-carboxylate Under $N_2$ protection, a mixture of tert-butyl 4-(4-(2-chloro-4-(1-methyl-5-(3-(trifluoromethyl)-pyrazol-4-yl)-imidazole-2-carboxamido)benzoyl)piperazine-1-carbonyl) piperidine-1-carboxylate (200 mg, 0.3 mmol), 2-bromo-5-(2-methoxyethoxy)pyridine (133.9 mg, 0.6 mmol), copper (I) iodide (54.9 mg, 0.3 mmol) and trans-n,n'-dimethylcyclohexane-1,2-diamine (82.1 mg, 0.6 mmol) in N,N-dimethylformamide, extra dry (3.3 mL) was heated at 100° C. for 1 h. Then the mixture was concentrated and the residue was purified by flash column to give the title compound as a black oil, 220 mg. MS $[M+H]^+$: 845.3.

Step 2: N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formic acid tert-butyl 4-[4-[2-chloro-4-[[5-[1-[5-(2-methoxyethoxy)-2-pyridyl]-3-(trifluoromethyl)pyrazol-4-yl]-1-methyl-imidazole-2-carbonyl]amino]benzoyl]piperazine-1-carbonyl] piperidine-1-carboxylate (300 mg, 0.4 mmol) was stirred in 1 M HCl/MeOH solution (1.8 mL) for 4 h at rt. Then the solvent was concentrated and the residue was purified by preparative HPLC to give the title compound as a white powder, 46 mg. MS $[M+H]^+$: 744.4.

Step 3: N-[3-chloro-4-[4-(1,1-dimethylpiperidin-1-ium-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formate Under $N_2$ protection, a mixture of N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide;formic acid (300 mg, 0.4 mmol), iodomethane (127 mg, 1.2 mmol) and DIEA (521 mg, 4.0 mmol) were stirred in ethanol (4.0 mL) at rt for 18 h. Then the mixture was concentrated and the residue was purified by preparative HPLC to give the title compound as an off-white powder, 50 mg. MS $[M]^+$: 772.4.

Example H1

5-[1-(5-Amino-2-pyridyl)-3-(trifluoromethyl)pyrazol-4-yl]-N-[3-chloro-4-[4-(4,4-dimethylpiperazin-4-ium-1-carbonyl)piperidine-1-carbonyl]phenyl]-1-methyl-imidazole-2-carboxamide; formate

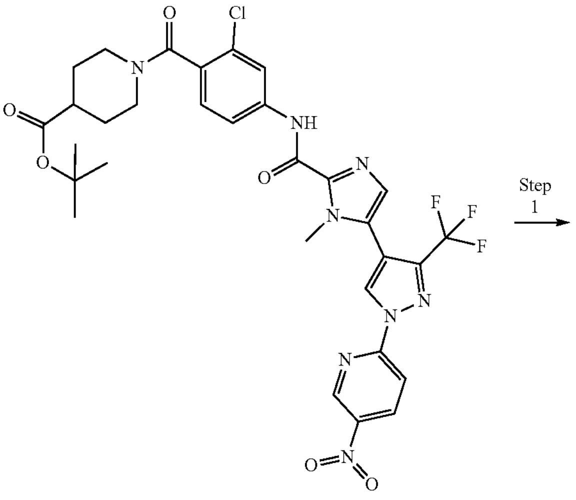

Intermediate C4

-continued

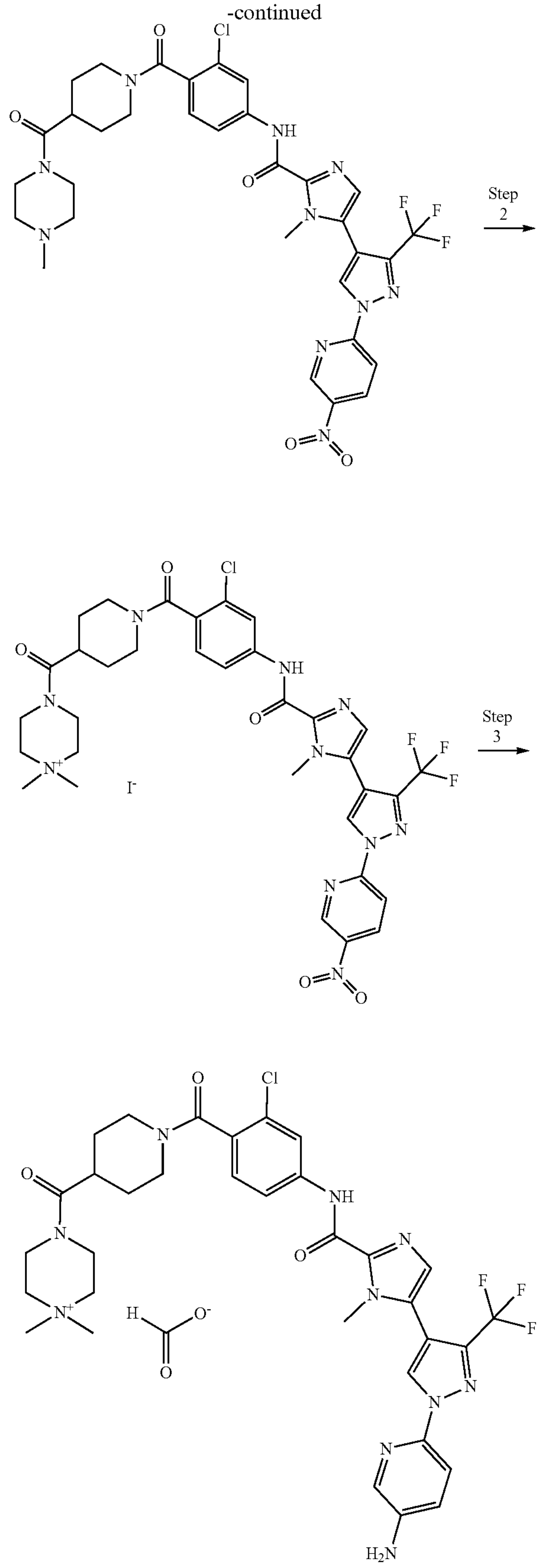

Example H1

Step 1: N-[3-chloro-4-[4-(4-methylpiperazine-1-carbonyl)piperidine-1-carbonyl]phenyl]-1-methyl-5-[1-(5-nitro-2-pyridyl)-3-(trifluoromethyl)pyrazol-4-yl]imidazole-2-carboxamide tert-butyl 1-[2-chloro-4-[[1-methyl-5-[1-(5-nitro-2-pyridyl)-3-(trifluoromethyl)pyrazol-4-yl]imidazole-2-carbonyl]amino]benzoyl]piperidine-4-carboxylate (200 mg, 0.3 mmol) was dissolved in 20% TFA/DCM solution (5 mL), and stirred at rt for 3 h. The solvent was removed in vacuum. The residue, 1-methylpiperazine (37.2 mg, 41.2 uL, 0.4 mmol), HATU (129.3 mg, 0.3 mmol) and DIEA (119.9 mg, 162.0 uL, 0.9 mmol) were stirred in acetonitrile (3.1 mL) at rt for 30 min. The solvent was removed in vacuum, the residue was purified by flash chromatography to yield the title compound as light yellow oil, 224 mg. MS $[M+H]^+$: 729.3.

Step 2: N-[3-chloro-4-[4-(4,4-dimethylpiperazin-4-ium-1-carbonyl)piperidine-1-carbonyl]phenyl]-1-methyl-5-[1-(5-nitro-2-pyridyl)-3-(trifluoromethyl)pyrazol-4-yl]imidazole-2-carboxamide; iodide N-[3-chloro-4-[4-(4-methylpiperazine-1-carbonyl)piperidine-1-carbonyl]phenyl]-1-methyl-5-[1-(5-nitro-2-pyridyl)-3-(trifluoromethyl)pyrazol-4-yl]imidazole-2-carboxamide (220 mg, 0.3 mmol) was dissolved in acetonitrile (3.1 mL). To this solution was added iodomethane (85.7 mg, 37.7 uL, 0.6 mmol). The mixture was stirred at 25° C. for 18 h. The solvent was removed in vacuum, and the crude was used in the next step without any purification. MS $[M+H]^+$: 745.3.

Step 3: 5-[1-(5-amino-2-pyridyl)-3-(trifluoromethyl)pyrazol-4-yl]-N-[3-chloro-4-[4-(4,4-dimethylpiperazin-4-ium-1-carbonyl)piperidine-1-carbonyl]phenyl]-1-methyl-imidazole-2-carboxamide; formate N-[3-chloro-4-[4-(4,4-dimethylpiperazin-4-ium-1-carbonyl)piperidine-1-carbonyl]phenyl]-1-methyl-5-[1-(5-nitro-2-pyridyl)-3-(trifluoromethyl)pyrazol-4-yl]imidazole-2-carboxamide (200 mg, 0.3 mmol) and ammonium chloride (718.8 mg, 13.4 mmol) were suspended in ethanol (4.0 mL) and water (1.3 mL). The mixture was stirred at room temperature for 1 h. Then zinc (351.4 mg, 5.4 mmol) was added, the mixture was stirred at room temperature for another 1 h. After completion, the reaction was filtered through Celite, The filtrate was concentrated in vacuum. The crude material was dissolved in 5 mL DMAc, filtered and purified by preparative HPLC to yield the title compound as off-white powder. MS $[M]^+$: 713.4.

The following compounds were prepared in analogy of Example H1.

| Ex# | Name | Structure | MS ESI $[M + H]^+$ | Starting Material |
|---|---|---|---|---|
| Example H2 | 5-[1-(5-amino-2-pyridyl)-3-(trifluoromethyl)pyrazol-4-yl]-N-[3-chloro-4-[4-[3-(hydroxymethyl)-4,4-dimethyl-piperazin-4-ium-1-carbonyl]piperidine-1-carbonyl]phenyl]-1-methyl-imidazole-2-carboxamide; formate | 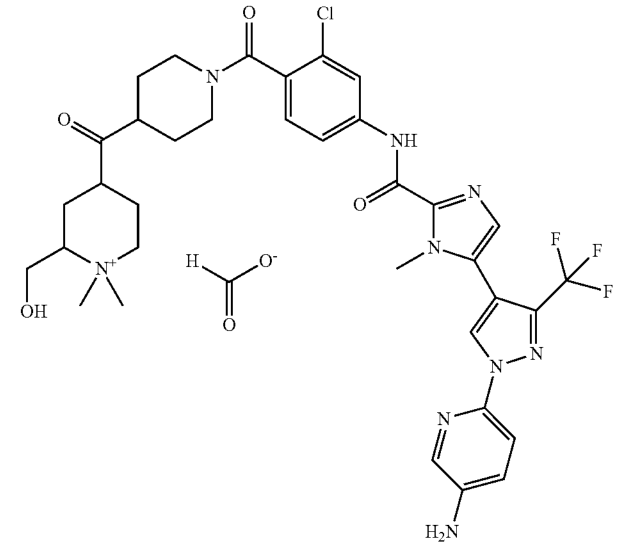 | 743.4 | Intermediate D14 and 1-boc-(2-hydroxymethyl) piperazine and iodomethane |

Example I1

5-[1-(5-Amino-2-pyridyl)-3-(trifluoromethyl)pyrazol-4-yl]-N-[3-chloro-4-[4-[(4,4-dimethyl-2-oxo-piperazin-4-ium-1-yl)methyl]piperidine-1-carbonyl]phenyl]-1-methyl-imidazole-2-carboxamide; formate

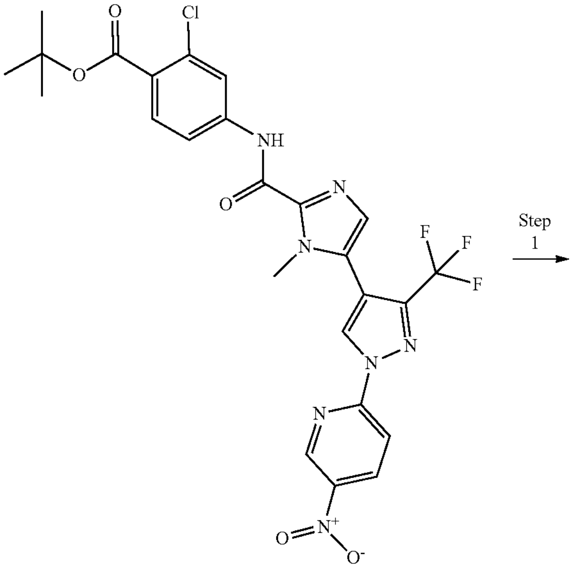

Intermediate C5

-continued

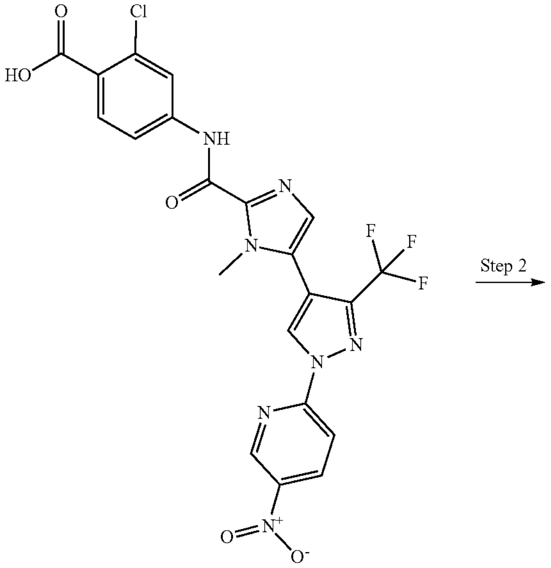

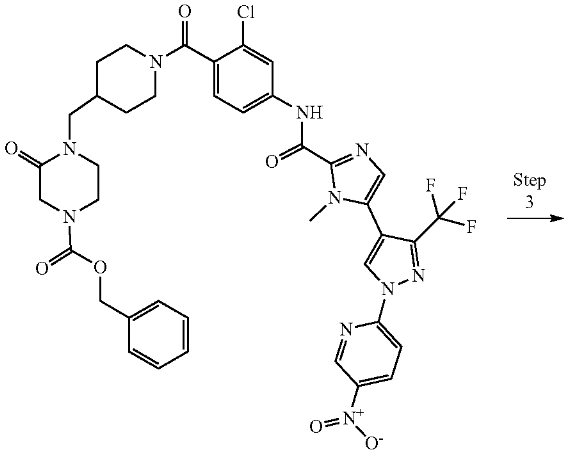

-continued

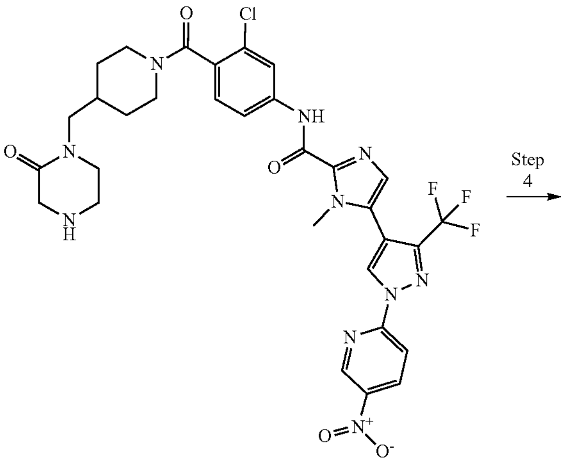

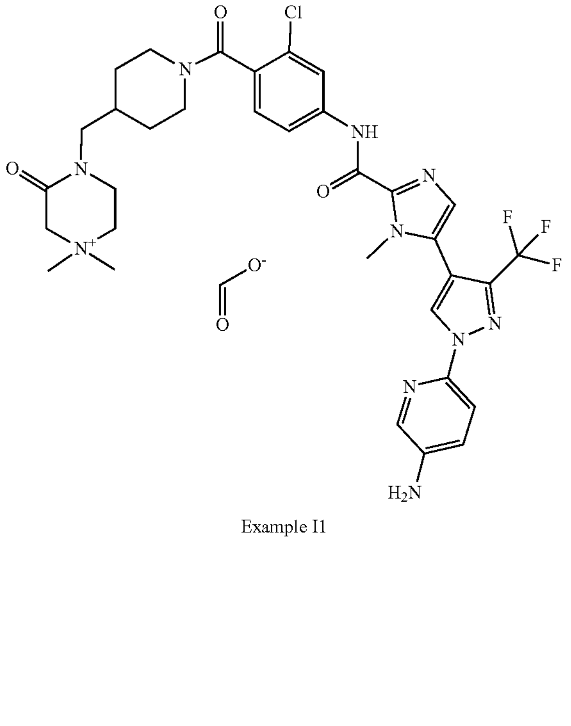

Example I1

Step 1: 2-chloro-4-[[1-methyl-5-[1-(5-nitro-2-pyridyl)-3-(trifluoromethyl)pyrazol-4-yl]imidazole-2-carbonyl]amino]benzoic acid tert-butyl 1-[2-chloro-4-[[1-methyl-5-[1-(5-nitro-2-pyridyl)-3-(trifluoromethyl)pyrazol-4-yl]imidazole-2-carbonyl]amino]benzoyl]piperidine-4-carboxylate (180 mg, 0.3 mmol) was dissolved in 20% TFA/DCM solution (5 mL), and stirred at rt for 3 h. The solvent was removed in vacuum. The residue was used in the next step without further purification.

Step 2: benzyl 4-[[1-[2-chloro-4-[[1-methyl-5-[1-(5-nitro-2-pyridyl)-3-(trifluoromethyl)pyrazol-4-yl] imidazole-2-carbonyl]amino]benzoyl]-4-piperidyl] methyl]-3-oxo-piperazine-1-carboxylate 2-chloro-4-[[1-methyl-5-[1-(5-nitro-2-pyridyl)-3-(trifluoromethyl)pyrazol-4-yl]imidazole-2-carbonyl]amino]benzoic acid (165 mg, 0.3 mmol), benzyl 3-oxo-4-(4-piperidylmethyl) piperazine-1-carboxylate (144.7 mg, 0.4 mmol), DIEA (217.1 mg, 293.4 uL, 1.7 mmol) and HATU (153.3 mg, 0.4 mmol) were stirred in acetonitrile (5 mL) at rt for 1 h. The solvent was removed in vacuum, the residue was purified by flash chromatography to give the title compound as light yellow oil, 250 mg. MS $[M+H]^+$: 849.6.

Step 3: N-[3-chloro-4-[4-[(2-oxopiperazin-1-yl) methyl]piperidine-1-carbonyl]phenyl]-1-methyl-5-[1-(5-nitro-2-pyridyl)-3-(trifluoromethyl)pyrazol-4-yl]imidazole-2-carboxamide benzyl 4-[[1-[2-chloro-4-[[1-methyl-5-[1-(5-nitro-2-pyridyl)-3-(trifluoromethyl)pyrazol-4-yl]imidazole-2-carbonyl]amino]benzoyl]-4-piperidyl]methyl]-3-oxo-piperazine-1-carboxylate (250 mg, 0.3 mmol) was heated in TFA (5 mL) under microwave at 100° C. for 1 h. The solvent was removed in vacuum. The residue was used in the next step without purification. MS $[M+H]^+$: 715.4.

Step 4: 5-[1-(5-amino-2-pyridyl)-3-(trifluoromethyl) pyrazol-4-yl]-N-[3-chloro-4-[4-[(4,4-dimethyl-2-oxo-piperazin-4-ium-1-yl)methyl]piperidine-1-carbonyl]phenyl]-1-methyl-imidazole-2-carboxamide; formate N-[3-chloro-4-[4-[(2-oxopiperazin-1-yl)methyl]piperidine-1-carbonyl]phenyl]-1-methyl-5-[1-(5-nitro-2-pyridyl)-3-(trifluoromethyl)pyrazol-4-yl]imidazole-2-carboxamide (100 mg, 0.1 mmol), DIEA (180.7 mg, 244.2 uL, 1.4 mmol) and iodomethane (79.4 mg, 35.0 uL, 0.6 mmol) were stirred in ethanol (4 mL) at rt for 18 h. The solvent was removed in vacuum. The residue was dissolve in ethanol (4 mL) and 1 mL water. To this solution was added ammonium chloride (74.8 mg, 1.4 mmol) and zinc (182.9 mg, 2.8 mmol). The mixture was stirred at rt for 3 h. The mixture was filtered, the filtrate was concentrated in vacuum, the residue was dissolved in DMF and purified by preparative HPLC to give the title compound as light yellow powder, 40 mg. MS $[M]^+$: 713.5.

Example J1

5-[1-(5-Amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate

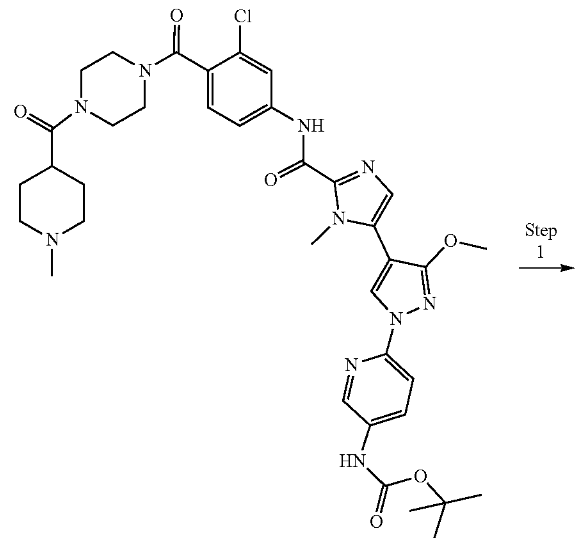

Intermediate C8

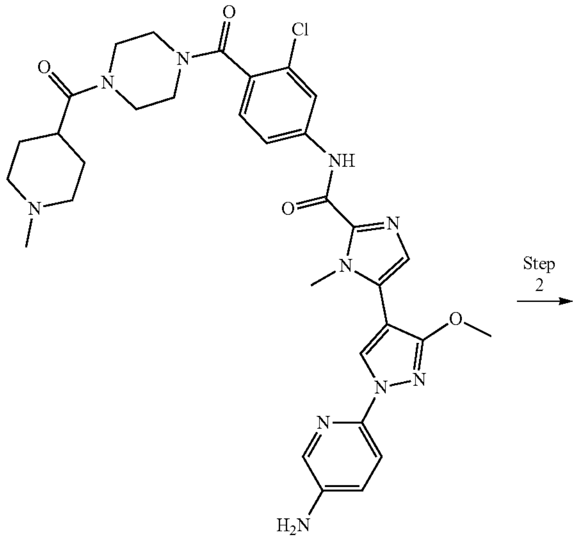

-continued

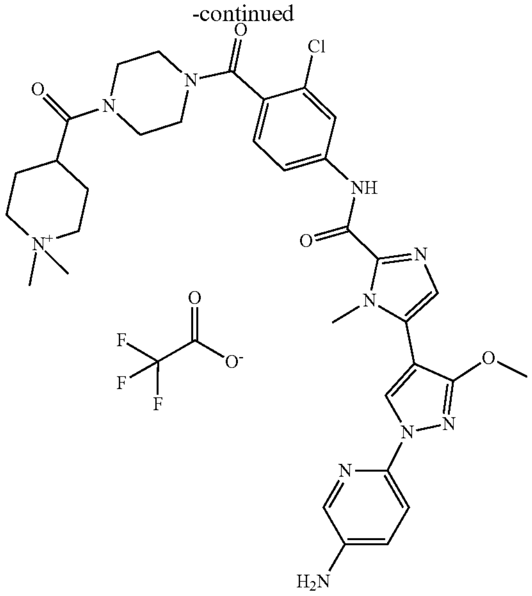

Example J1

Step 1: 5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide; 2,2,2-trifluoroacetic acid A solution of compound tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-methoxy-pyrazol-1-yl]-3-pyridyl]carbamate (100.0 mg, 0.13 mmol) in HCl/dioxane (2.0 mL, 8.00 mmol) was stirred at 20° C. for 2 h. The reaction mixture was concentrated in vacuum to give a residue, which was purified by Prep-HPLC (0.1% TFA as additive) and dried by lyophilization to give 5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide; 2,2,2-trifluoroacetic acid (50.0 mg, 0.06 mmol, 53% yield) as a yellow solid. MS $[M+H]^+$: 661.3.

Step 2: 5-[1-(5-amino-2-pyridyl)-3-methoxy-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate (RW-40-57)

To a solution of 5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide;2,2,2-trifluoroacetic acid (30.0 mg, 0.05 mmol) in ACN (2.0 mL) was added DIEA (58.5 mg, 0.45 mmol) and iodomethane (32.2 mg, 0.23 mmol). The mixture was stirred at 20° C. for 2 h. The reaction mixture was filtered and the filtrate was concentrated in vacuum to give a residue, which was purified by flash column (0.1% TFA as additive) and dried by lyophilization to give 5-[1-(5-amino-2-pyridyl)-3-methoxy-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate (17.3 mg) as a yellow solid. MS $[M+H]^+$: 675.3.

The following compounds were prepared in analogy of Example J1.

| Ex# | Name | Structure | MS ESI [M + H]+ | Starting Material |
|---|---|---|---|---|
| Example J2 | 5-[1-(5-amino-2-pyridyl)-3-cyano-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate | 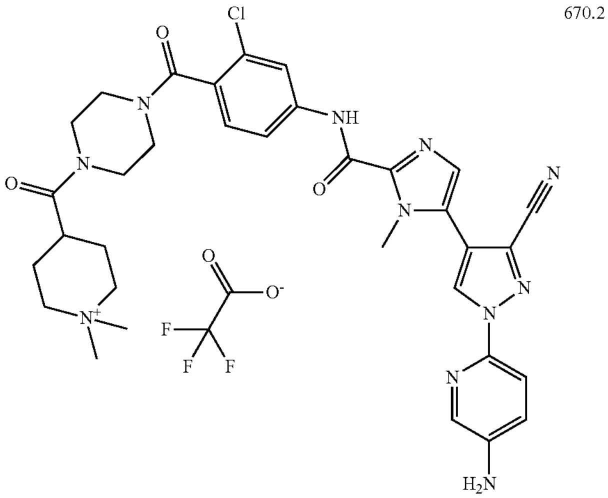 | 670.2 | Intermediate D19 and HCl and iodomethane |
| Example J3 | 5-[1-(5-amino-2-pyridyl)-3-methyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate | 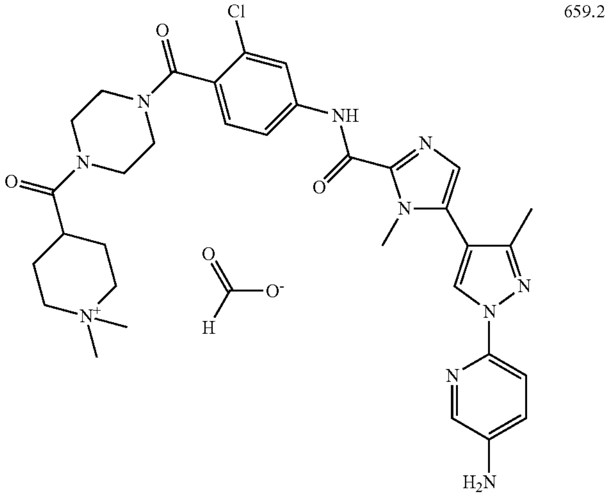 | 659.2 | Intermediate D20 and HCl and iodomethane |
| Example J4 | 5-[1-(5-amino-2-pyridyl)-3-ethyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate | 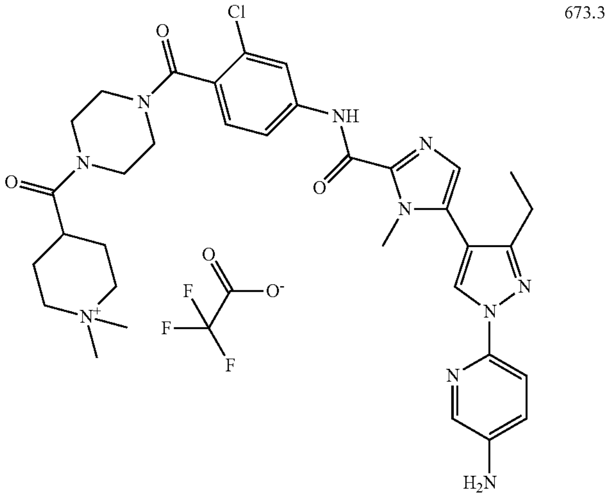 | 673.3 | Intermediate D21 and HCl and iodomethane |

Example K1

5-[1-(6-Aminopyridazin-3-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate

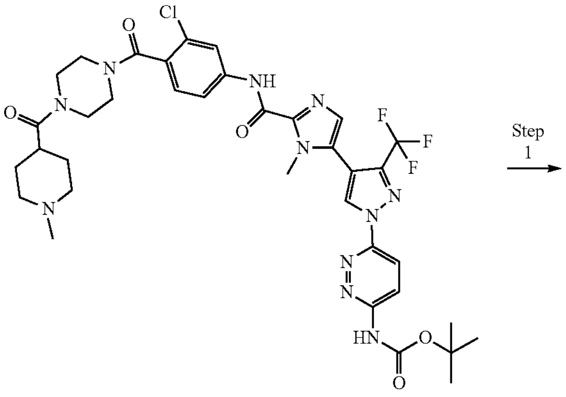

Intermediate C12

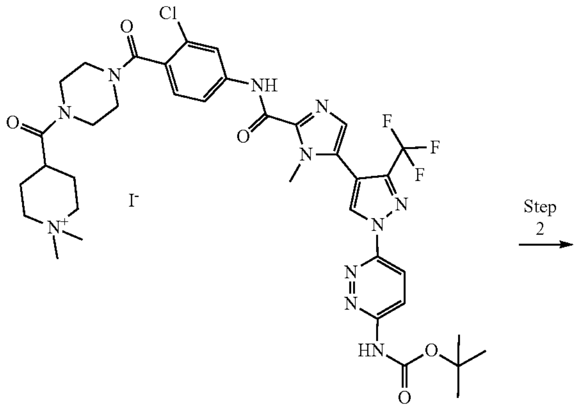

-continued

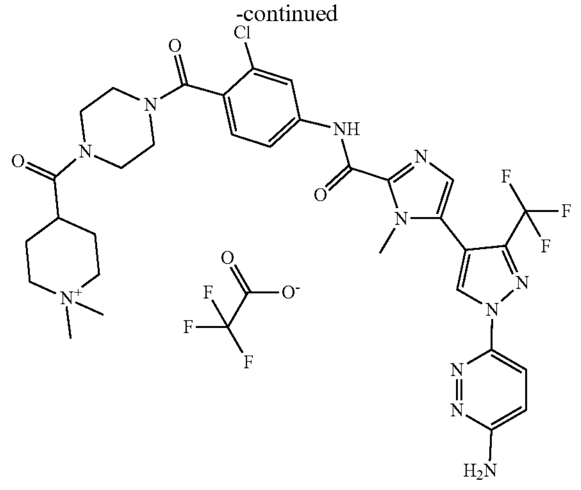

Example K1

Step 1: tert-butyl N-[6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]pyridazin-3-yl]carbamate; iodide To a solution of Intermediate D22 (50.0 mg, 0.06 mmol, 1.0 eq) and N,N-diisopropylethylamine (0.11 mL, 0.62 mmol, 10.0 eq) in ACN (2.0 mL) was added iodomethane (0.04 mL, 0.62 mmol, 10.0 eq) in one portion under $N_2$. This reaction mixture was stirred at 25° C. for 1 h. This reaction mixture was concentrated to get tert-butyl N-[6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]pyridazin-3-yl]carbamate;iodide (60.0 mg, 0.06 mmol, 102% yield) as brown solid (crude), which would be used in the next step directly without further purification. MS $[M+H]^+$: 814.1.

Step 2: 5-[1-(6-aminopyridazin-3-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetate A mixture of tert-butyl N-[6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3 (trifluoromethyl)pyrazol-1-yl]pyridazin-3-yl]carbamate;iodide (60.0 mg, 0.06 mmol, 1.0 eq) in hydrochloric acid in dioxane (4 M) (0.5 mL, 2.0 mmol, 31.41 eq) was stirred at 25° C. for 1 h. This reaction mixture was concentrated to get the crude product. The crude product was purified by Prep-HPLC (TFA) to get 5-[1-(6-aminopyridazin-3-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;2,2,2-trifluoroacetate (12.2 mg, 0.01 mmol, 21% yield) as white solid. MS $[M+H]^+$: 714.2.

The following compounds were prepared in analogy of Example K1. The order of steps can be interchanged.

| Ex# | Name | Structure | MS ESI [M + H]+ | Starting Material |
| --- | --- | --- | --- | --- |
| Example K2 | N-[3-chloro-4-[4-(1,1-dimethylpiperidin-1-ium-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide; 2,2,2-trifluoroacetate | 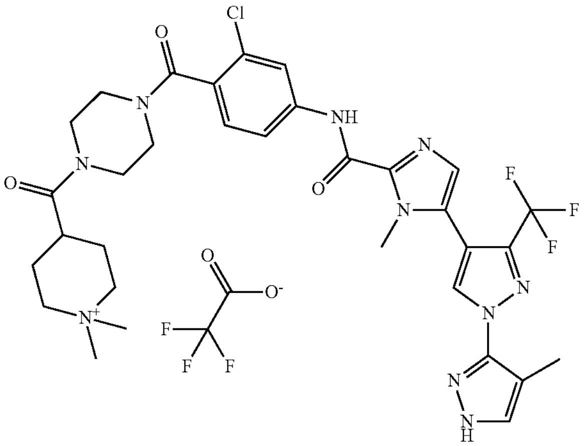 [SMILES: Cc1c[nH]nc1-n1cc(-c2cnc(C(=O)Nc3ccc(C(=O)N4CCN(C(=O)C5CC[N+](C)(C)CC5)CC4)c(Cl)c3)n2C)c(C(F)(F)F)n1 ; O=C([O-])C(F)(F)F] | 701.2 | Intermediate D23 and iodomethane, and HCl |
| Example K3 | N-[3-chloro-4-[4-(1,1-dimethylpiperidin-1-ium-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide; formate | 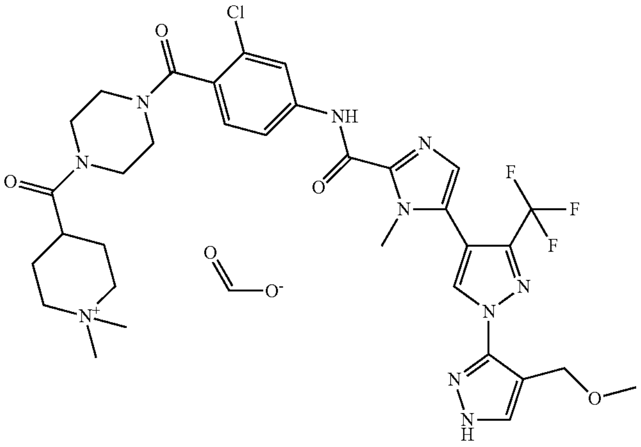 | 731.3 | Intermediate D35 and TFA in DCM, and iodomethane |

Example L1

5-[1-[5-[(3-Amino-3-oxo-propyl)amino]-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate

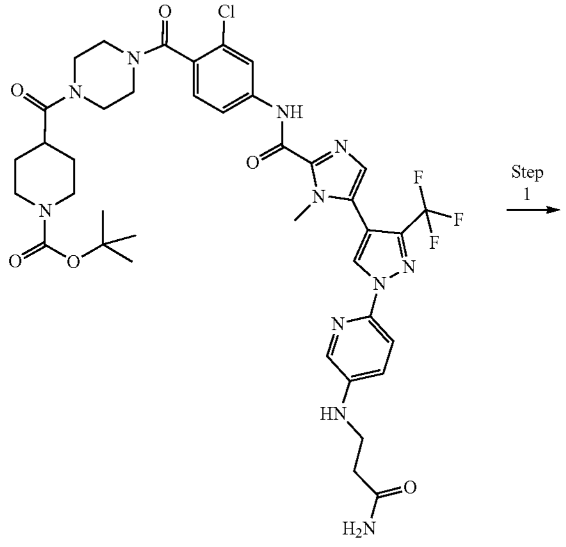

Intermediate D13

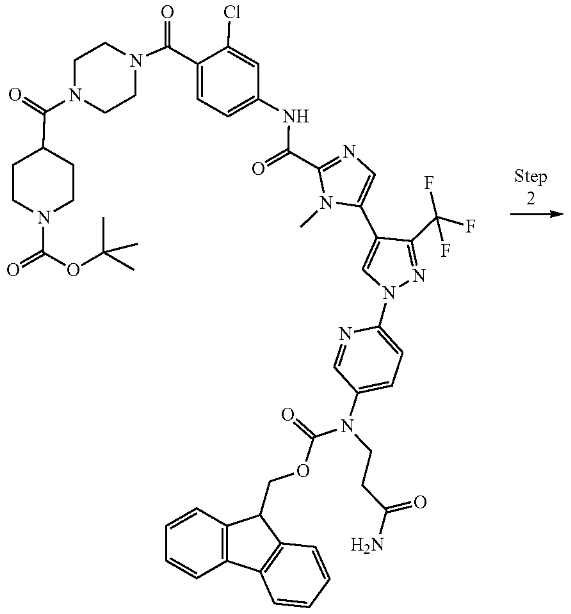

-continued

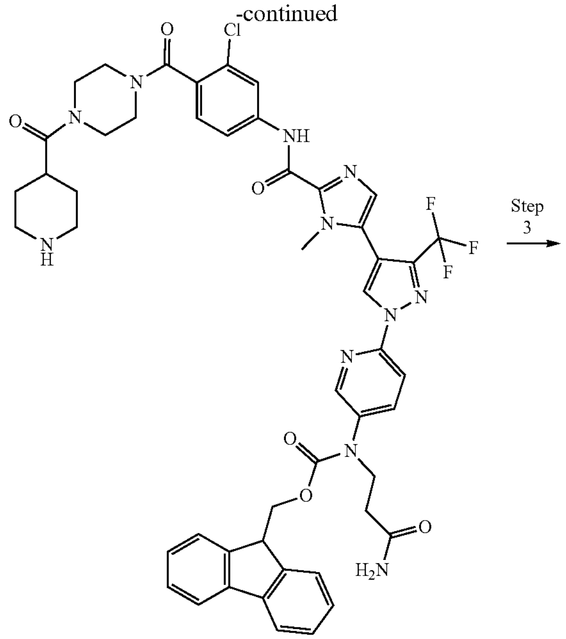

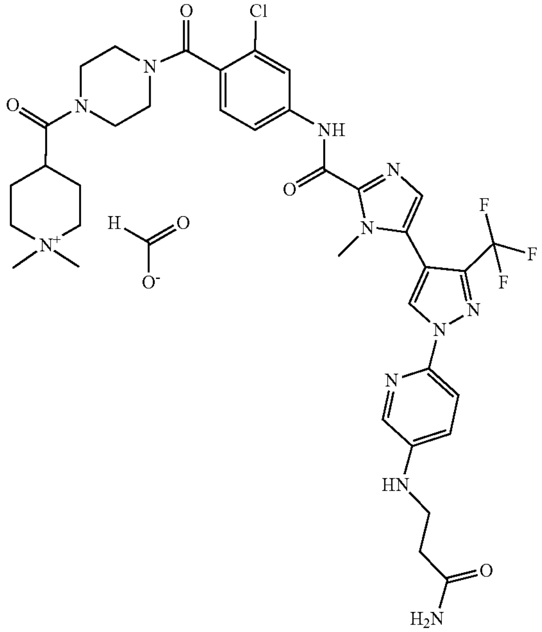

Example L1

Step 1: tert-butyl 4-[4-[4-[[5-[1-[5-[(3-amino-3-oxo-propyl)-(9H-fluoren-9-ylmethoxycarbonyl)amino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylate 4-[4-[4-[[5-[1-[5-[(3-amino-3-keto-propyl)amino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylic acid tert-butyl ester (426 mg, 0.5 mmol), chlorocarbonic acid 9H-fluoren-9-ylmethyl ester (154.4 mg, 0.6 mmol) and sodium bicarbonate (62.7 mg, 0.7 mmol) were stirred in 1,4-dioxane (10 mL) at rt for 24 h. The solvent was removed in vacuum. The residue was purified by flash chromatography to give 432 mg of the title compound as light yellow foam. MS $[M+H]^+$: 1078.4.

Step 2: 9H-fluoren-9-ylmethyl N-(3-amino-3-oxo-propyl)-N-[6-[4-[2-[[3-chloro-4-[4-(piperidine-4-carbonyl)piperazine-1-carbonyl]phenyl]carbamoyl]-3-methyl-imidazol-4-yl]-3-(trifluoromethyl)pyrazol-1-yl]-3-pyridyl]carbamate 4-[4-[4-[[5-[1-[5-[(3-amino-3-keto-propyl)-(9H-fluoren-9-ylmethoxycarbonyl)amino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylic acid tert-butyl ester (400 mg, 0.4 mmol) was dissolved in 5 mL 1 M HCl/MeOH solution. The solution was stirred at rt for 18 h. The solvent was removed in vacuum to give the crude product. MS $[M+H]^+$: 978.2.

Step 3: 5-[1-[5-[(3-amino-3-oxo-propyl)amino]-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; formate N-(3-amino-3-keto-propyl)-N-[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]carbamic acid 9H-fluoren-9-ylmethyl ester (360 mg, 0.4 mmol), iodomethane (208.9 mg, 92.0 uL, 1.5 mmol) and DIEA (475.5 mg, 642.6 uL, 3.7 mmol) were stirred in N,N-dimethylacetamide (5 mL) at rt for 30 min. 1 mL piperidine was added to the solution and the stirring was continued for 15 min. The product was purified by preparative HPLC directly to give 50 mg of the title compound as white powder. MS $[M]^+$: 784.3.

The following compounds were prepared in analogy of Example L1.

| Ex# | Name | Structure | MS ESI $[M]^+$ | Starting Material |
|---|---|---|---|---|
| Example L2 | N-[3-chioro-4-[4-(1,1-dimethylpiperidin-1-ium-4-carbonyl)piperazine-1-carbonyl]phenyl]-5-[1-[5-[[3-keto-3-(methylamino)propyl]amino]-2-pyridyl]-3-(trifluoromethyl)pyrazol-4-yl]-l-methyl-imidazole-2-carboxamide; formate | 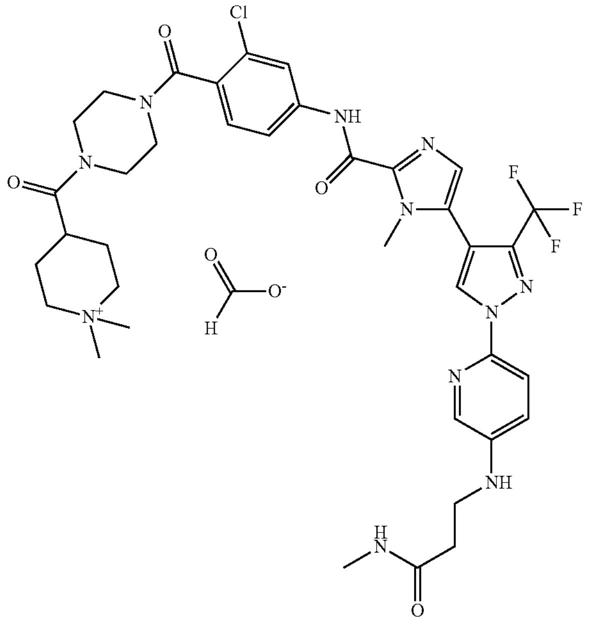 | 799.1 | Intermediate D13; Example L2 was isolated together with Example L1 |

Example M1
5-[1-[5-(2-aminoethylamino)-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetic acid; 2,2,2-trifluoroacetate
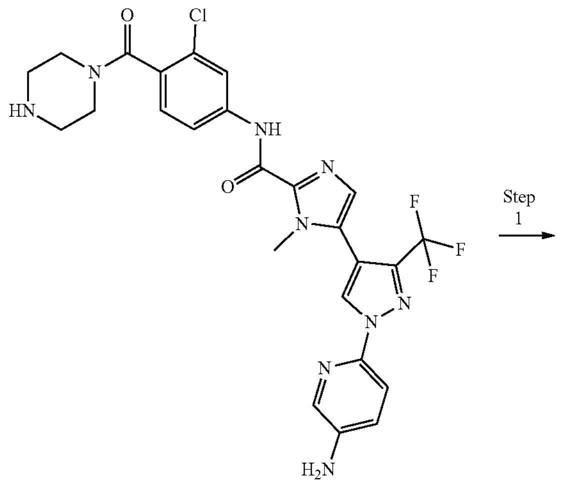
Intermediate E20
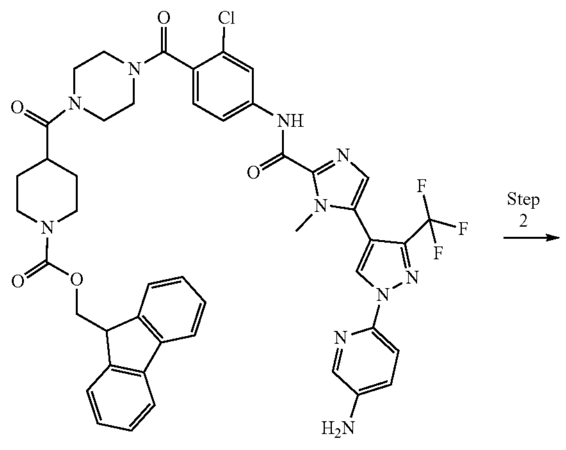
-continued
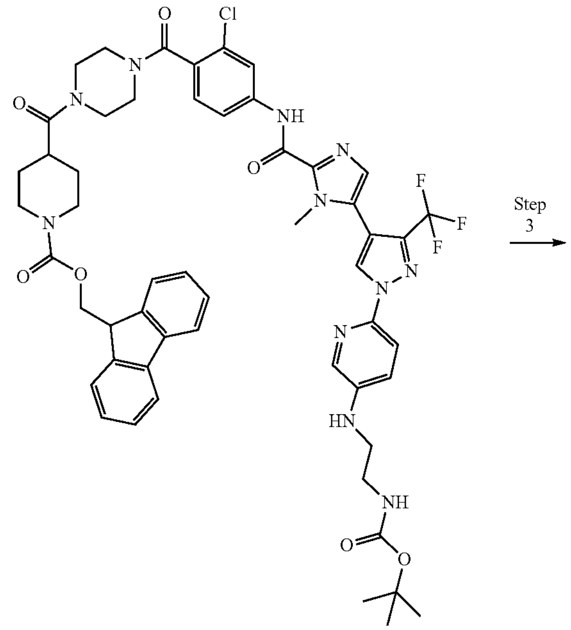
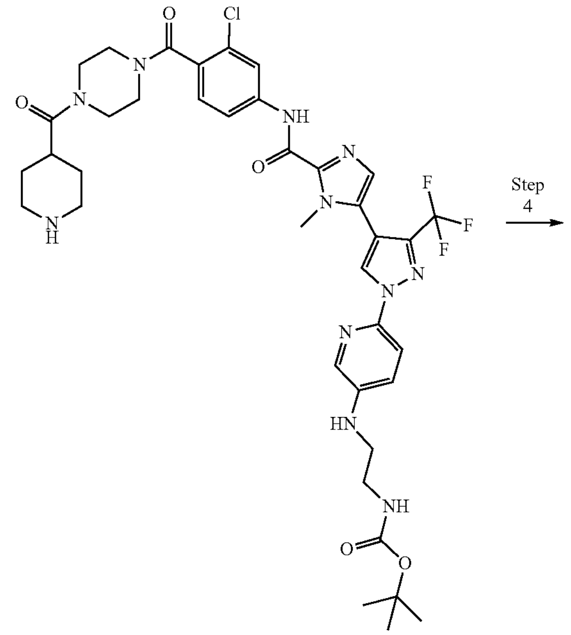

-continued

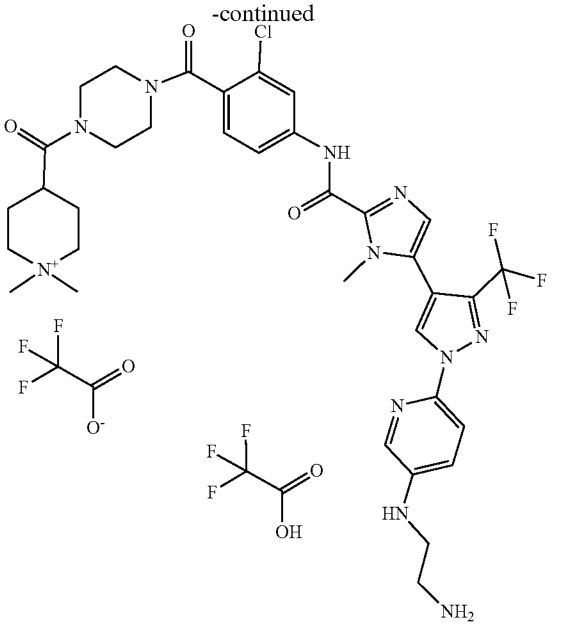

Example M1

Step 1: 4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylic acid 9H-fluoren-9-ylmethyl ester A mixture of 5-[1-(5-amino-2-pyridyl)-3-(trifluoromethyl)pyrazol-4-yl]-N-[3-chloro-4-(piperazine-1-carbonyl)phenyl]-1-methyl-imidazole-2-carboxamide;hydrogen chloride (100 mg, 0.162 mmol, 1 eq) and 1-[(9H-fluoren-9-ylmethoxy)carbonyl]piperidine-4-carboxylic acid (59.84 mg, 0.170 mmol, 1.05 eq) in N,N-dimethylformamide (2 mL) was treated with N-ethyldiisopropylamine (83.84 mg, 113. uL, 0.649 mmol, 4 eq), and subsequently with PyAOP (101.47 mg, 0.195 mmol, 1.2 eq), and the mixture was stirred at RT for 2.5 h. The reaction mixture was transferred into half-sat. $NaHCO_3$ (50 mL), and extracted with EtOAc (3x22 mL). The combined organics were washed with brine (20 mL), dried ($Na_2SO_4$), filtered, and evaporated. Purification by MPLC (15-85% EtOAc/EtOH 3:1 in heptane) afforded the title compound (137 mg, 85.65%) as light yellow solid. MS $[M+2H]^+$: 454.6.

Step 2: 4-[4-[4-[[5-[1-[5-[2-(tert-butoxycarbonylamino)ethylamino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylic acid 9H-fluoren-9-ylmethyl ester A mixture of 4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylic acid 9H-fluoren-9-ylmethyl ester (137 mg, 0.139 mmol, 1 eq) in dichloromethane (2 mL) was treated with molecular sieves, 3a (?, 0.139 mmol, 1 eq), N-(2-ketoethyl)carbamic acid tert-butyl ester (33.17 mg, 0.208 mmol, 1.5 eq), and acetic acid (16.68 mg, 15.9 uL, 0.278 mmol, 2 eq), cooled to 0° C., and stirred for 10 min. Subsequently, sodium triacetoxyborohydride (51.52 mg, 0.243 mmol, 1.75 eq) was added portionwise during 30 min, after which stirring was continued at RT for 2 h. The mixture was diluted with EtOAc and half-sat. $NaHCO_3$ (50 mL) and extracted with EtOAc (3x20 mL). The combined organics were washed with brine (20 mL), dried ($Na_2SO_4$), filtered, and evaporated. Purification by MPLC (10-90% EtOAc/EtOH 3:1 in heptane) afforded the title compound (128 mg, 78.94%) as off-white solid, which seemed to contain some impurities by NMR, but was used in the next step without any further purification. MS $[M+HCOO]^-$: 1094.9.

Step 3: N-[2-[[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]amino]ethyl]carbamic acid tert-butyl ester A mixture of 4-[4-[4-[[5-[1-[5-[2-(tert-butoxycarbonylamino)ethylamino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylic acid 9H-fluoren-9-ylmethyl ester (128 mg, 0.110 mmol, 1 eq) in acetonitrile (2.5 mL) was treated with 2 M dimethylamine in THF (548.3 uL, 1.1 mmol, 10 eq), and the mixture was stirred at RT for 3 h, and evaporated. Purification by MPLC (0-100% DCM/MeOH/$Et_3N$ 8:2:0.2 in DCM) afforded a residue, which was dissolved in 0.1 M NaOH (25 mL), and extracted with EtOAc (3x12 mL). The combined organics were washed with brine (12 mL), dried ($Na_2SO_4$), filtered, and evaporated to afford the title compound (60 mg, 60.77%) as white solid. MS $[M+HCOO]^-$: 872.6.

Step 4: 5-[1-[5-(2-aminoethylamino)-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; 2,2,2-trifluoroacetic acid; 2,2,2-trifluoroacetate A mixture of N-[2-[[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]amino]ethyl]carbamic acid tert-butyl ester (34 mg, 0.038 mmol, 1 eq) in N,N-dimethylformamide (2.5 mL) was treated with $K_2CO_3$ (20.88 mg, 0.151 mmol, 4 eq), and subsequently with iodomethane (21.44 mg, 9.45 uL, 0.151 mmol, 4 eq). The mixture was stirred at 40° C. for 2.5 h, and evaporated to afford crude N-[2-[[6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]-3-pyridyl]amino]ethyl]carbamic acid tert-butyl ester;iodide (37 mg, 86.6%) as off-white solid, which was directly used in the next step. MS $[M]^+$: 856.6.

A mixture of N-[2-[[6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]-3-pyridyl]amino]ethyl]carbamic acid tert-butyl ester;iodide (37 mg, 0.033 mmol, 1 eq) in dichloromethane (2.5 mL) and 4 M HCl in dioxane (900 mg, 0.750 mL, 3 mmol, 91.73 eq) was stirred at RT for 3 h, and evaporated. Purification by RPHPLC gave the title compound (19.3 mg, 59.95%) as white lyoph solid. MS $[M+2HCOO]^-$: 846.7.

Assay Procedures

Antimicrobial Susceptibility Testing:

90% Growth Inhibitory Concentration (IC90) Determination

The in vitro antimicrobial activity of the compounds was determined according to the following procedure:

The assay used a 10-points Iso-Sensitest broth medium to measure quantitatively the in vitro activity of the compounds against *Acinetobacter baumannii* ATCC17961.

Stock compounds in DMSO were serially twofold diluted (e.g. range from 50 to 0.097 μM final concentration) in 384 wells microtiter plates and inoculated with 49 μl the bacterial suspension in Iso-Sensitest medium to have a final cell concentration of ~$5\times10^{(5)}$ CFU/ml in a final volume/well of 50 ul/well. Microtiter plates were incubated at 35±2° C.

Bacterial cell growth was determined with the measurement of optical density at λ=600 nm each minutes over a time course of 16 h. Growth inhibition was calculated during the logarithmic growth of the bacterial cells with determination of the concentration inhibiting 50% (IC50) and 90% (IC90) of the growth.

Table 1 provides the 90% growth inhibitory concentrations (IC90) in micromoles per liter of the compounds of present invention obtained against the strain *Acinetobacter baumannii* ATCC17961.

Particular compounds of the present invention exhibit an IC90 (*Acinetobacter baumannii* ATCC17961)≤25 μmol/l.

More particular compounds of the present invention exhibit an IC90 (*Acinetobacter baumannii* ATCC17961)≤5 μmol/l.

Most particular compounds of the present invention exhibit an IC90 (*Acinetobacter baumannii* ATCC17961)≤1 μmol/l.

TABLE 1

| Example | ATCC 17961 IC90 [μM] |
|---|---|
| Example A1 | 0.095 |
| Example A2 | 0.98 |
| Example A3 | 0.82 |
| Example A4 | 0.25 |
| Example A5 | 0.76 |
| Example A6 | 1.3 |
| Example A7 | 0.55 |
| Example A8 | 0.33 |
| Example A9 | 0.29 |
| Example A10 | 0.51 |
| Example A11 | 0.23 |
| Example A12 | 0.27 |
| Example B1 | 0.94 |
| Example B2 | 1.6 |
| Example B3 | 3.8 |
| Example B4 | 1.9 |
| Example B5 | 0.31 |
| Example B6 | 0.36 |
| Example B7 | 1.6 |
| Example B8 | 1.5 |
| Example B9 | 5.2 |
| Example C1 | 0.41 |
| Example C2 | 1.1 |
| Example D1 | 0.31 |
| Example D2 | 0.4 |
| Example D3 | 0.15 |
| Example D4 | / |
| Example D5 | 0.24 |
| Example D6 | 0.37 |
| Example D7 | 0.4 |
| Example D8 | 0.23 |
| Example D10 | 0.33 |
| Example D11 | 0.21 |
| Example D12 | 1.3 |
| Example D13 | 0.42 |
| Example D14 | 0.55 |
| Example D15 | 0.55 |

TABLE 1-continued

| Example | ATCC 17961 IC90 [μM] |
|---|---|
| Example D16 | 0.32 |
| Example D17 | 0.30 |
| Example D18 | 0.29 |
| Example E1 | 0.1 |
| Example E2 | 0.3 |
| Example E3 | 0.39 |
| Example E4 | / |
| Example E5 | 0.22 |
| Example E6 | 0.37 |
| Example E7 | 0.33 |
| Example E8 | 0.22 |
| Example F1 | 0.39 |
| Example G1 | 0.35 |
| Example H1 | 0.61 |
| Example H2 | 0.64 |
| Example I1 | / |
| Example J1 | 10 |
| Example J2 | 9.83 |
| Example J3 | 10 |
| Example J4 | / |
| Example K1 | 1.6 |
| Example K2 | 4.36 |
| Example K3 | 1.3 |
| Example L1 | / |
| Example L2 | 0.33 |
| Example M1 | 0.1 |

Example 1

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 2

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 3

A compound of formula (I) can be used in a manner known per se as the active ingredient for the production of an infusion solution of the following composition:

| | |
|---|---|
| Active ingredient | 100 mg |
| Lactic acid 90% | 100 mg |
| NaOH q.s. or HCl q.s. for adjustment to pH 4.0 | |
| Sodium chloride q.s. or glucose q.s. for adjustment of the osmolality to 290 mOsm/kg | |
| Water for injection (WFI) | ad 100 ml |

Example 4

A compound of formula (I) can be used in a manner known per se as the active ingredient for the production of an infusion solution of the following composition:

| | |
|---|---|
| Active ingredient | 100 mg |
| Hydroxypropyl-beta-cyclodextrin | 10 g |
| NaOH q.s. or HCl q.s. for adjustment to pH 7.4 | |
| Sodium chloride q.s. or glucose q.s. for adjustment of the osmolality to 290 mOsm/kg | |
| Water for injection (WFI) | ad 100 ml |

The invention claimed is:

1. A compound of formula (I)

(I)

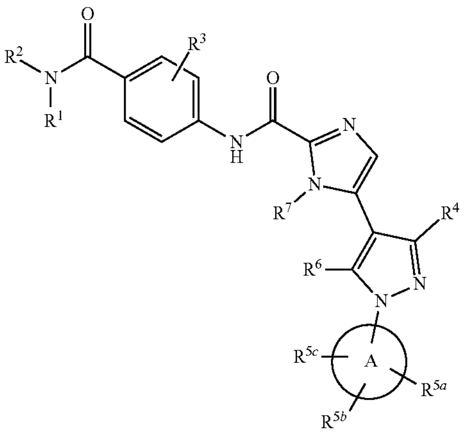

or a pharmaceutically acceptable salt thereof, wherein:

$R^1$ and $R^2$, taken together with the nitrogen atom to which they are attached, form a group of formula (II) or (III)

(II)

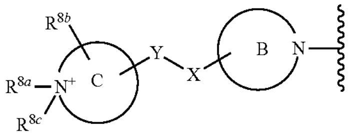

(III)

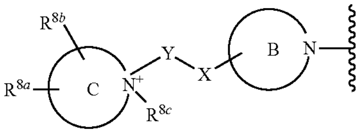
;

or $R^1$ is

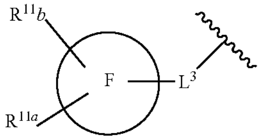

and $R^2$ is hydrogen or $C_1$-$C_6$-alkyl;

$R^3$ is selected from the group consisting of hydrogen, halogen, $C_1$-$C_6$-alkyl and $C_1$-$C_6$-alkoxy;

$R^4$ and $R^6$ are each independently selected from the group consisting of hydrogen, $C_1$-$C_6$-alkyl, $C_1$-$C_6$-alkoxy, cyano, halo-$C_1$-$C_6$-alkyl and halo-$C_1$-$C_6$-alkoxy;

$R^{5a}$, $R^{5b}$ and $R^{5c}$ are each independently selected from the group consisting of hydrogen, halogen, hydroxy, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, $C_1$-$C_6$-alkyl-NH—C(O)—$C_1$-$C_6$-alkyl-NH—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, carbamoyl and nitro;

$R^7$ is selected from the group consisting of hydrogen, $C_1$-$C_6$-alkyl and halo-$C_1$-$C_6$-alkyl;

in formula (II), $R^{8a}$ is selected from the group consisting of $C_1$-$C_6$-alkyl, carbamoyl-$C_1$-$C_6$-alkyl and

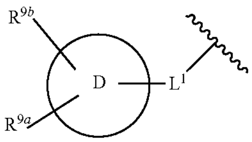
;

in formula (III), $R^{8a}$ is selected from the group consisting of hydrogen, $C_1$-$C_6$-alkyl, carbamoyl-$C_1$-$C_6$-alkyl and

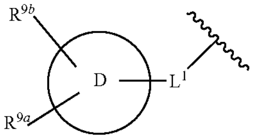
;

$R^{8b}$ is selected from the group consisting of hydrogen, hydroxy, hydroxy-$C_1$-$C_6$-alkyl, and

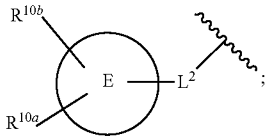
;

$R^{8c}$, $R^{12a}$ and $R^{12c}$ are independently $C_1$-$C_6$-alkyl;

$R^{9a}$, $R^{9b}$, $R^{10a}$, $R^{10b}$ and $R^{12b}$ are each independently selected from the group consisting of hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro and hydroxy;

$R^{11a}$ and $R^{11b}$ are each independently selected from the group consisting of hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro, hydroxy and

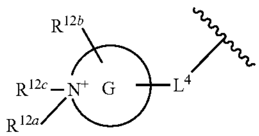

;

X is carbonyl and Y is selected from the group consisting of a covalent bond, —NH—, —N($C_1$-$C_6$-alkyl)-, and $C_1$-$C_6$-alkyldiyl; or X is $C_1$-$C_6$-alkyldiyl and Y is a covalent bond;

$L^1$ and $L^3$ are each independently selected from the group consisting of a covalent bond, carbonyl and $C_1$-$C_6$-alkyldiyl;

$L^2$ and $L^4$ are each independently selected from the group consisting of a covalent bond, carbonyl, —O—, —NH—C(O)—, —C(O)—NH— and $C_1$-$C_6$-alkyldiyl;

A and E are each independently 5- to 14-membered heteroaryl;

B, C, D, F and G are each independently 3- to 14-membered heterocyclyl.

2. The compound of claim 1, or a pharmaceutically acceptable salt thereof, wherein the compound is a compound of formula (I-I)

(I-I)

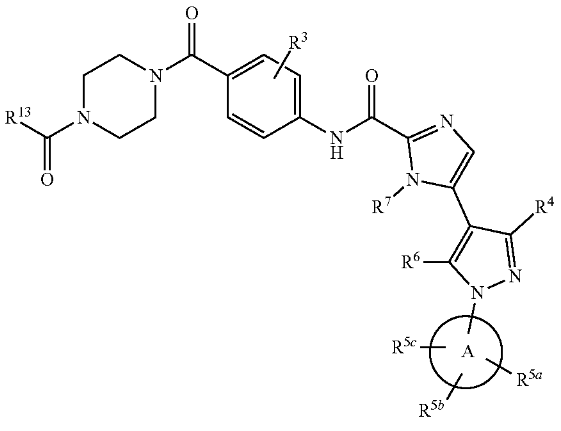

wherein:

$R^{13}$ is

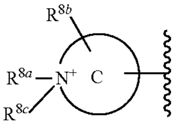

or

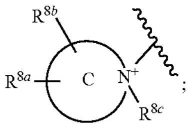

;

and $R^3$, $R^4$, $R^{5a}$, $R^{5b}$, $R^{5c}$, $R^6$, $R^7$, $R^{8a}$ and $R^{8b}$ are as defined in claim 1.

3. The compound of claim 1, or a pharmaceutically acceptable salt thereof, wherein the compound is a compound of formula (I-II)

(I-II)

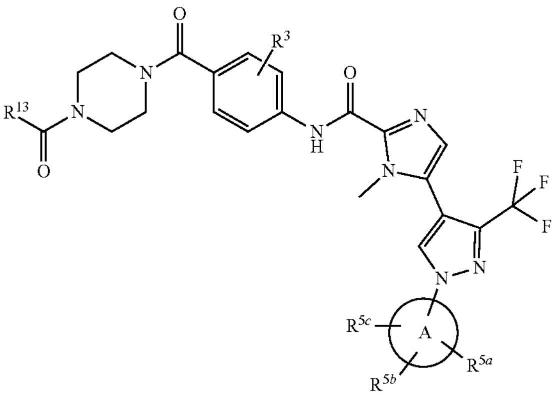

wherein:

$R^{13}$ is

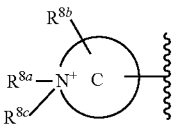

or

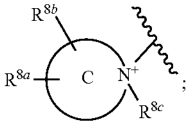

;

and $R^3$, $R^{5a}$, $R^{5b}$, $R^{5c}$, $R^{8a}$ and $R^{8b}$ are as defined in claim 1.

4. The compound of claim 1, or a pharmaceutically acceptable salt thereof, wherein $R^1$ and $R^2$, taken together with the nitrogen atom to which they are attached, form a group of formula (II) or (III)

(II)

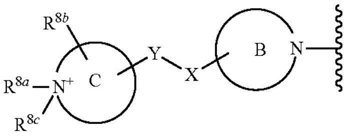

-continued (III)

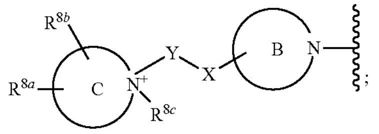

or $R^1$ is

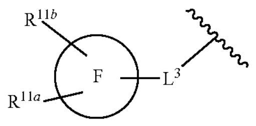

and $R^2$ is hydrogen;

$R^{9a}$, $R^{9b}$, $R^{10b}$ and $R^{11b}$ are each hydrogen;

in formula (II), $R^{8a}$ is selected from the group consisting of $C_1$-$C_6$-alkyl, carbamoyl-$C_1$-$C_6$-alkyl and

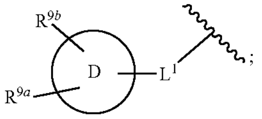

in formula (III), $R^{8a}$ is selected from the group consisting of hydrogen, $C_1$-$C_6$-alkyl, carbamoyl-$C_1$-$C_6$-alkyl and

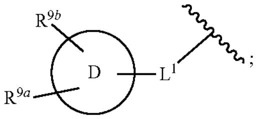

$R^{8b}$ is selected from the group consisting of hydrogen, hydroxy and

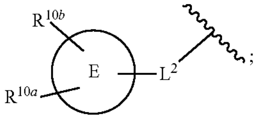

$R^{8c}$, $R^{12a}$ and $R^{12c}$ are independently $C_1$-$C_6$-alkyl;

$R^{10a}$ is amino or nitro;

$R^{11a}$ is

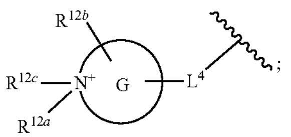

$R^{12b}$ is hydrogen or hydroxy;

X is carbonyl;

Y is a covalent bond or $C_1$-$C_6$-alkyldiyl;

$L^1$ is $C_1$-$C_6$-alkyldiyl;

$L^2$ is —O—;

$L^3$ is a covalent bond;

$L^4$ is carbonyl;

B, C, D, F and G are each independently 3- to 14-membered heterocyclyl; and

E is 5- to 14-membered heteroaryl.

5. The compound of claim 4, or a pharmaceutically acceptable salt thereof, wherein $R^1$ and $R^2$, taken together with the nitrogen atom to which they are attached, form a group of formula (II)

(II)

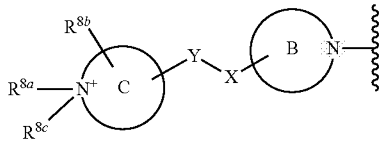

$R^{8a}$ and $R^{8c}$ are both independently $C_1$-$C_6$-alkyl, $R^{8b}$ is hydrogen or hydroxy;

X is carbonyl;

Y is a covalent bond; and

B and C are each independently 3- to 14-membered heterocyclyl.

6. The compound of claim 5, or a pharmaceutically acceptable salt thereof, wherein $R^1$ and $R^2$, taken together with the nitrogen atom to which they are attached, form a group of formula (II)

(II)

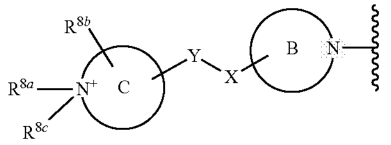

$R^{8a}$ and $R^{8c}$ are both methyl, $R^{8b}$ is hydrogen or hydroxy;

X is carbonyl;

Y is a covalent bond;

B is piperazinyl; and

C is piperidyl or pyrrolidinyl.

7. The compound of claim 1, or a pharmaceutically acceptable salt thereof, wherein $R^3$ is halogen or $C_1$-$C_6$-alkyl.

8. The compound of claim 7, or a pharmaceutically acceptable salt thereof, wherein $R^3$ is halogen.

9. The compound of claim 1, or a pharmaceutically acceptable salt thereof, wherein $R^4$ is selected from the group consisting of $C_1$-$C_6$-alkyl, $C_1$-$C_6$-alkoxy, cyano and halo-$C_1$-$C_6$-alkyl; and $R^6$ is hydrogen or halo-$C_1$-$C_6$-alkyl.

10. The compound of claim 9, or a pharmaceutically acceptable salt thereof, wherein $R^4$ is halo-$C_1$-$C_6$-alkyl; and $R^6$ is hydrogen.

11. The compound of claim 1, or a pharmaceutically acceptable salt thereof, wherein A is 5- to 14-membered heteroaryl;

$R^{5a}$ is selected from the group consisting of hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, $C_1$-$C_6$-alkyl-NH—C (O)—$C_1$-$C_6$-alkyl-NH—, amino-$C_1$-$C_6$-alkyl-NH—, $C_1$-$C_6$-alkoxy-$C_1$-$C_6$-alkyl-NH—, carbamoyl and nitro; and $R^{5b}$ is hydrogen or $C_1$-$C_6$-alkyl; and $R^{5c}$ is hydrogen.

12. The compound of claim 11, or a pharmaceutically acceptable salt thereof, wherein A is 5- to 14-membered heteroaryl;

$R^{5a}$ is selected from the group consisting of $C_1$-$C_6$-alkoxy, hydroxy-$C_1$-$C_6$-alkyl, $C_1$-$C_6$-alkyl-NH—, amino-$C_1$-$C_6$-alkyl-NH— and amino;

$R^{5b}$ is hydrogen or $C_1$-$C_6$-alkyl; and $R^{5c}$ is hydrogen.

13. The compound of claim 12, or a pharmaceutically acceptable salt thereof, wherein A is pyridyl;

$R^{5a}$ is selected from the group consisting of methoxy, hydroxymethyl, methylamino, 2-aminoethylamino and amino;

$R^{5b}$ is hydrogen or methyl; and $R^{5c}$ is hydrogen.

14. The compound of claim 1, or a pharmaceutically acceptable salt thereof, wherein $R^7$ is $C_1$-$C_6$-alkyl.

15. The compound of claim 1, or a pharmaceutically acceptable salt thereof, wherein:

$R^1$ and $R^2$, taken together with the nitrogen atom to which they are attached, form a group of formula (II) or (III)

(II)

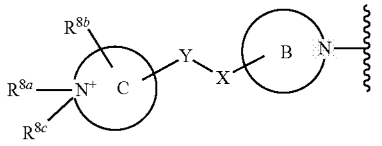

(III)

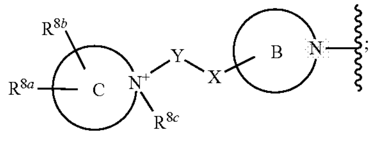

or $R^1$ is

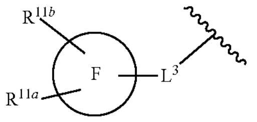

and $R^2$ is hydrogen;

$R^3$ is halogen or $C_1$-$C_6$-alkyl;

$R^4$ is selected from the group consisting of $C_1$-$C_6$-alkyl, $C_1$-$C_6$-alkoxy, cyano and halo-$C_1$-$C_6$-alkyl;

$R^{5a}$ is selected from the group consisting of hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, $C_1$-$C_6$-alkyl-NH—C(O)—$C_1$-$C_6$-alkyl-NH—, amino-$C_1$-$C_6$-alkyl-NH—, $C_1$-$C_6$-alkoxy-$C_1$-$C_6$-alkyl-NH—, carbamoyl and nitro;

$R^{5b}$ is hydrogen or $C_1$-$C_6$-alkyl;

$R^{5c}$, $R^{9a}$, $R^{9b}$, $R^{10b}$, $R^{11b}$ and $R^{12b}$ are each hydrogen;

$R^6$ is hydrogen or halo-$C_1$-$C_6$-alkyl;

$R^7$ is $C_1$-$C_6$-alkyl;

in formula (II), $R^{8a}$ is selected from the group consisting of $C_1$-$C_6$-alkyl, carbamoyl-$C_1$-$C_6$-alkyl and

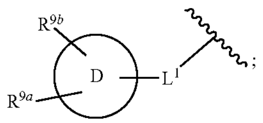

in formula (III), $R^{8a}$ is selected from the group consisting of hydrogen, $C_1$-$C_6$-alkyl, carbamoyl-$C_1$-$C_6$-alkyl and

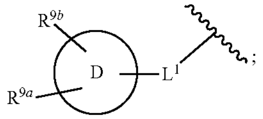

$R^{8b}$ is selected from the group consisting of hydrogen, hydroxy and

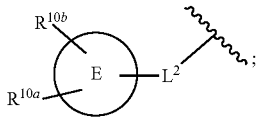

$R^{8c}$, $R^{12a}$ and $R^{12c}$ are independently $C_1$-$C_6$-alkyl;

$R^{10a}$ is amino or nitro;

$R^{11a}$ is

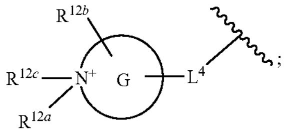

$R^{12b}$ is hydrogen or hydroxy;

X is carbonyl;

Y is a covalent bond or $C_1$-$C_6$-alkyldiyl;

$L^1$ is $C_1$-$C_6$-alkyldiyl;

$L^2$ is —O—;

$L^3$ is a covalent bond;

$L^4$ is carbonyl;

A and E are each independently 5- to 14-membered heteroaryl; and

B, C, D, F and G are each independently 3- to 14-membered heterocyclyl.

16. The compound of claim 15, or a pharmaceutically acceptable salt thereof, wherein:

$R^1$ and $R^2$, taken together with the nitrogen atom to which they are attached, form a group of formula (II)

(II)

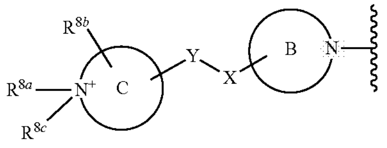

$R^3$ is halogen;

$R^4$ is halo-$C_1$-$C_6$-alkyl;

$R^{5a}$ is selected from the group consisting of $C_1$-$C_6$-alkoxy, hydroxy-$C_1$-$C_6$-alkyl, $C_1$-$C_6$-alkyl-NH— and amino;

$R^{5b}$ is hydrogen or $C_1$-$C_6$-alkyl;

$R^{5c}$ and $R^6$ are each hydrogen;

$R^7$ is $C_1$-$C_6$-alkyl;

$R^{8a}$ and $R^{8c}$ are both independently $C_1$-$C_6$-alkyl;

$R^{8b}$ is hydrogen or hydroxy;

X is carbonyl;

Y is a covalent bond;

A is 5- to 14-membered heteroaryl; and

B and C are each independently 3- to 14-membered heterocyclyl.

17. The compound of claim 16, or a pharmaceutically acceptable salt thereof, wherein:

$R^1$ and $R^2$, taken together with the nitrogen atom to which they are attached, form a group of formula (II)

(II)

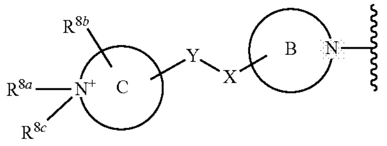

$R^3$ is chloro;

$R^4$ is $CF_3$;

$R^{5a}$ is selected from the group consisting of methoxy, hydroxymethyl, methylamino and amino;

$R^{5b}$ is hydrogen or methyl;

$R^{5c}$ and $R^6$ are each hydrogen;

$R^7$ is methyl;

$R^{8a}$ and $R^{8c}$ are both methyl;

$R^{8b}$ is hydrogen or hydroxy;

X is carbonyl;

Y is a covalent bond;

A is pyridyl;

B is piperazinyl; and

C is piperidyl or pyrrolidinyl.

18. The compound of claim 1, or a pharmaceutically acceptable salt thereof, wherein the compound is selected from the group consisting of:

N-[3-Chloro-4-[4-(1,1-dimethylpiperidin-1-ium-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide;

6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]pyridine-3-carboxamide;

6-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-3-(trifluoromethyl)pyrazol-1-yl]-N-methyl-pyridine-3-carboxamide;

N-[3-chloro-4-[4-(1,1-dimethylpiperidin-1-ium-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide;

5-[1-(5-amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-Chloro-4-[4-(1,1-dimethylpiperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-(3-hydroxy-1,1-dimethyl-piperidin-1-ium-4-carbonyl)piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-[(3S,4R)-3-hydroxy-1,1-dimethyl-piperidin-1-ium-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

N-[4-[4-[1-(Azetidin-3-ylmethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

5-[1-(5-Amino-2-pyridyl)-3-(trifluoromethyl)pyrazol-4-yl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(2S,3S)-3-hydroxy-1,1-dimethyl-pyrrolidin-1-ium-2-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(3-hydroxy-1,1-dimethyl-piperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3R,4R)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S,4R)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S,4S)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3R,4S)-3-hydroxy-1,1-dimethyl-piperidin-1-ium-4-carbonyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(4-hydroxy-1,1-dimethyl-piperidin-1-ium-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[2-(3-hydroxy-1-methyl-pyrrolidin-1-ium-1-yl)acetyl]piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[[1-(1,1-dimethylpiperidin-1-ium-4-carbonyl)-4-piperidyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S)-4,4-dimethylmorpholin-4-ium-3-carbonyl]piperazine-1-carbonyl]phenyl]-1-methyl-imidazole-2-carboxamide;

N-[4-[4-[(2S,3S)-3-[(5-amino-2-pyridyl)oxy]-1,1-dimethyl-pyrrolidin-1-ium-2-carbonyl]piperazine-1-carbonyl]-3-chloro-phenyl]-5-[1-(5-amino-2-pyridyl)-3-(trifluoromethyl)pyrazol-4-yl]-1-methyl-imidazole-2-carboxamide;

5-[1-(5-Amino-2-pyridyl)-3-(trifluoromethyl)pyrazol-4-yl]-N-[3-chloro-4-[4-[(2S)-4-hydroxy-1,1-dimethyl-piperidin-1-ium-2-carbonyl]piperazine-1-carbonyl]phenyl]-1-methyl-imidazole-2-carboxamide;

N-[3-Chloro-4-[4-(1,1-dimethylpiperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-(1,1-dimethylpiperidin-1-ium-4-carbonyl)piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide;

N-[3-chloro-4-[4-(1,1-dimethylpiperidin-1-ium-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide;

N-[3-chloro-4-[4-(4-hydroxy-1,1-dimethyl-piperidin-1-ium-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[2-(3-hydroxy-1-methyl-pyrrolidin-1-ium-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[4-[4-(1,1-dimethylpiperidin-1-ium-4-carbonyl)piperazine-1-carbonyl]-3-methyl-phenyl]-1-methyl-5-[1-[5-(methylamino)-2-pyridyl]-3-(trifluoromethyl)pyrazol-4-yl]imidazole-2-carboxamide;

N-[3-chloro-4-[4-[(3S,4R)-3-hydroxy-1,1-dimethyl-piperidin-1-ium-4-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-Chloro-4-[4-(1,1-dimethylpiperidin-1-ium-4-carbonyl)piperazine-1-carbonyl]phenyl]-5-[1-[5-(hydroxymethyl)-2-pyridyl]-3-(trifluoromethyl)pyrazol-4-yl]-1-methyl-imidazole-2-carboxamide;

N-[3-Chloro-4-[4-(1,1-dimethylpiperidin-1-ium-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide;

5-[1-(5-Amino-2-pyridyl)-3-(trifluoromethyl)pyrazol-4-yl]-N-[3-chloro-4-[4-(4,4-dimethylpiperazin-4-ium-1-carbonyl)piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[3-(hydroxymethyl)-4,4-dimethyl-piperazin-4-ium-1-carbonyl]piperidine-1-carbonyl]phenyl]-1-methyl-imidazole-2-carboxamide;

5-[1-(5-Amino-2-pyridyl)-3-(trifluoromethyl)pyrazol-4-yl]-N-[3-chloro-4-[4-[(4,4-dimethyl-2-oxo-piperazin-4-ium-1-yl)methyl]piperidine-1-carbonyl]phenyl]-1-methyl-imidazole-2-carboxamide;

5-[1-(5-Amino-2-pyridyl)-3-(difluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-cyano-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-methyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-2-pyridyl)-3-ethyl-pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(6-Aminopyridazin-3-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide;

5-[1-[5-[(3-Amino-3-oxo-propyl)amino]-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

4-(2-chloro-4-(1-methyl-5-(1-(pyrimidin-2-yl)-3-(trifluoromethyl)-1H-pyrazol-4-yl)-1H-imidazole-2-carboxamido)benzoyl)-1,1-dimethylpiperazin-1-ium;

rac-(2R,4S)-2-((1R,5S,6S)-6-(2-chloro-4-(1-methyl-5-(1-(pyrimidin-2-yl)-3-(trifluoromethyl)-1H-pyrazol-4-yl)-

1H-imidazole-2-carboxamido)benzamido)-3-azabicyclo[3.1.0]hexane-3-carbonyl)-4-hydroxy-1,1-dimethylpyrrolidin-1-ium;

N-[3-chloro-4-[4-[(2S,3S)-3-hydroxy-1,1-dimethyl-pyrrolidin-1-ium-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

(exo)-6-[[4-[[5-[1-(5-aminopyridin-2-yl)-3-(trifluoromethyl)pyrazol-4-yl]-1-methylimidazole-2-carbonyl]amino]-2-chlorobenzoyl]amino]-[(trans)-4-hydroxy-1,1-dimethylpyrrolidin-1-ium-3-yl]-3-azabicyclo[3.1.0]hexane-3-carboxamide;

N-[3-chloro-4-[4-(1,1-dimethylpiperidin-1-ium-4-carbonyl)piperazine-1-carbonyl]phenyl]-5-[1-[5-[[3-keto-3-(methylamino)propyl]amino]-2-pyridyl]-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[[(exo)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-1-methyl-imidazole-2-carboxamide;

5-[1-(5-aminopyrazin-2-yl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide;

5-[1-(5-amino-3-fluoro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-4-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-6-fluoro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-6-methyl-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide;

5-[1-(5-amino-4-chloro-2-pyridyl)-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide; and 5-[1-[5-(2-aminoethylamino)-2-pyridyl]-3-(trifluoromethyl)pyrazol-4-yl]-N-[3-chloro-4-[4-(1,1-dimethylpiperidin-1-ium-4-carbonyl)piperazine-1-carbonyl]phenyl]-1-methyl-imidazole-2-carboxamide.

19. A pharmaceutical composition comprising a compound of claim 1, or a pharmaceutically acceptable s alt thereof, and a therapeutically inert carrier.

20. A method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, the method comprising administering a compound of claim 1, or a pharmaceutically acceptable salt thereof, to a mammal in need thereof.

* * * * *